(12) United States Patent
Liu et al.

(10) Patent No.: US 7,049,374 B2
(45) Date of Patent: May 23, 2006

(54) HETERODIAMONDOIDS

(75) Inventors: Shenggao Liu, Hercules, CA (US); Robert M. Carlson, Petaluma, CA (US); Jeremy E. Dahl, Palo Alto, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 38 days.

(21) Appl. No.: 10/622,130

(22) Filed: Jul. 16, 2003

(65) Prior Publication Data

US 2004/0059145 A1 Mar. 25, 2004

Related U.S. Application Data

(60) Provisional application No. 60/397,367, filed on Jul. 18, 2002.

(51) Int. Cl.
C08F 20/00 (2006.01)
(52) U.S. Cl. .................. 525/437; 525/538; 525/540; 525/535; 528/170; 546/61; 556/13; 556/64; 556/27
(58) Field of Classification Search ............ 546/61, 546/13; 556/64, 27; 528/170; 525/437, 525/538, 540, 535
See application file for complete search history.

(56) References Cited

U.S. PATENT DOCUMENTS

| | | | |
|---|---|---|---|
| 3,457,318 A | 7/1969 | Capaldi et al. |
| 3,832,332 A | 8/1974 | Thompson |
| 4,880,613 A | 11/1989 | Satoh et al. |
| 4,950,463 A | 8/1990 | Satoh et al. |
| 4,959,201 A | 9/1990 | Satoh et al. |
| 4,985,226 A | 1/1991 | Satoh et al. |
| 5,017,734 A | 5/1991 | Baum et al. |
| 5,019,660 A | 5/1991 | Chapman et al. |
| 5,382,684 A | 1/1995 | Moini et al. |
| 5,382,809 A | 1/1995 | Nishibayashi et al. |
| 5,414,189 A | 5/1995 | Chen et al. |
| 5,478,650 A | 12/1995 | Davanloo et al. |
| 5,632,812 A | 5/1997 | Hirabayashi |
| 5,656,828 A | 8/1997 | Zachai et al. |
| 5,792,256 A | 8/1998 | Kucherov et al. |
| 5,989,947 A | 11/1999 | Dilger et al. |
| 5,990,479 A | 11/1999 | Weiss et al. |
| 6,162,412 A | 12/2000 | Fujimori et al. |
| 6,207,392 B1 | 3/2001 | Weiss et al. |
| 6,235,851 B1 | 5/2001 | Ishii et al. |
| 6,274,837 B1 | 8/2001 | Windischmann et al. |
| 6,306,610 B1 | 10/2001 | Bawendi et al. |
| 6,309,701 B1 | 10/2001 | Barbera-Guillem |
| 6,322,901 B1 | 11/2001 | Bawendi et al. |
| 6,326,144 B1 | 12/2001 | Bawendi et al. |
| 6,340,393 B1 | 1/2002 | Yoshida |
| 6,377,340 B1 | 4/2002 | Anthony et al. |
| 6,423,551 B1 | 7/2002 | Weiss et al. |
| 6,548,171 B1 | 4/2003 | Barbera-Guillem et al. |
| 6,576,155 B1 | 6/2003 | Barbera-Guillem |

FOREIGN PATENT DOCUMENTS

| | | |
|---|---|---|
| DE | 2545292 | 4/1979 |
| WO | 95/06019 A1 | 3/1995 |
| WO | US02/00505 | 1/2002 |
| WO | 02/057021 A2 | 7/2002 |
| WO | 02/058139 A2 | 7/2002 |
| WO | 03/050066 A1 | 6/2003 |

OTHER PUBLICATIONS

Fritz, G., et al., "Silicon-Carbon Compounds with a Carborundum Structure". Abstract, *Angew, Chem, Internat. Edit.* 9(6) (1970).
Fritz, G., et al., "Uber die Isolierung Hoherer Carbosilane aus der Pyrolyse des Tetramethylsilans", *Z. anorg. allg. Chem*, 512 pps. 103-125 (1984).
Marchand, A.P., "Diamondoid Hydrocarbons—Delving into Nature's Bounty", *Science* 299, 52-52 (2003).
Mochizuki, Y, et al., "Polarizability of Silicon Clusters", *Chemical Physics Letters* 336, 451-456 (2001).
ISR for PCT/US03/22483
Beveratos, A, et al., "Single Photo Quantum Cyrpotography", *arXov quant-ph/0206136* 1 (2002).
Jones, R., et al., "Theory of Aggregation of Nitrogen in Diamond", *Properties, Growth and Applications of Diamond* edited by Nazare et al., Ch. A5.1, pp127-129 (2001).
Kiflawi, I, et al., "Aggregates of Nitrogen in Diamond", *Properties, Growth and Applications of Diamond* edited by Nazare et al., Ch. A5.2, pp 130-133 (2001).
Kiflawi, I., et al., "The Nitrogen Interstitial in Diamond", *Properties, Growth and Applications of Diamond* edited by Nazare et al., Ch. A5.3, pp 134-135 (2001).
Kuhn, S., et al., "Diamond Colour Centres as a Nanoscopic Light Source for Scanning Near-Field Optical Microscopy", *Journal of Microscopy* 202(1):2-6 (2001).

(Continued)

Primary Examiner—Taofiq Solola
Assistant Examiner—Robert Shiao
(74) Attorney, Agent, or Firm—Buchanan Ingersoll PC

(57) ABSTRACT

This invention is related to heteroatom containing diamondoids (i.e., "heterodiamondoids") which are compounds having a diamondoid nucleus in which one or more of the diamondoid nucleus carbons has been substitutionally replaced with a noncarbon atom. These heteroatom substituents impart desirable properties to the diamondoid. In addition, the heterodiamondoids are functionalized affording compounds carrying one or more functional groups covalently pendant therefrom. This invention is further related to polymerizable functionalized heterodiamondoids. In a preferred aspect of this invention the diamondoid nuclei are triamantane and higher diamondoid nuclei. In another preferred aspect, the heteroatoms are selected to give rise to diamondoid materials which can serve as n- and p-type materials in electronic devices can serve as optically active materials.

24 Claims, 51 Drawing Sheets

OTHER PUBLICATIONS

Lawson, S.C., et al., "the Effect of Transition Metals (TM) on the Aggregation Kinetics of Nitrogen in Diamond" *Properties, Growth and Applications of Diamond* edited by Nazare et al., Ch. A6.2, pp 172-173 (2001).

Raty, J.Y., et al., "Quantum Confinement and Fullerenelike Surface Reconstructions in Nanodiamonds", *Physical Review Letters* 90(3):037401.1-037401.4 (2003).

Zarda, P., "Single Photo Source ", http://scotty.quantum.physik.uni-muenchen.de/exp/sps/sum.html, on-line documents, 11 pages (2001).

U.S. Appl. No. 10/046,486, filed Jan. 16, 2002.

Balaban et al., Systematic Classification and Nomenclature of Diamond Hydrocarbons -I, *Tetrahedron* 34:3599-3606 (1978).

Baugman, G.I., "Dibromination of Adamantane", (1964).

Becker et al, "A Short Synthese of 1-azaadamantan-4-one and the 4r and 4s Isomers of 4-Amino-1-azaadamantane", *Synthesis* 11:1080-1082 (1992).

Bingham, R.C. et al., Chapter 18 of "Chemistry of Adamantanes", *Springer-Verlag* (1971).

Bishop, R., et al., "Detection of Non-Conjugative Interactions in Rigid Cyclic Molecules by Using Carbon-13 N.M.R. Shift Values", *Aust. J. Chem.* 40:249-255 (1987).

Black, R.M. et al., "Adamantane Chemistry. Part 3. Abnormal Hypoiodite Reactions of 2-Substituted Adamantan-2-ols; Synthetic Routes to 4-Oxahomo-and 2-Oxa-adamantanes, and 7-Substituted-bicyclo[3.3.1]nona-3-ols", *J. Chem. Soc. Perkins Trans*, I 410-418 (1980).

Blaney et al, "Chemistry of Diamantane, Part II. Synthesis of 3,5-disubstituted Derivatives", *Synthetic Communications* 3(6):435-439 (1973).

Boudjouk et al, "Synthesis and Reactivity of 1-Silaadamantyl Systems", *Journal of Organometallic Chemistry* 2:336-343 (1983).

Boudjouk et al, "The Reaction of Magnesium with cis-1,3,5-Trsi(bromomethyl)cyclohexane. Evidence For a Soluble Trigrignard", *Journal of Organometallic Chemistry* 281:C21-C23 (1985).

Bubnov et al, "A Novel Method of Synthesis of 1-azaadamantane from 1-boraadamantane", *Journal of Organometallic Chemistry* 412:1-8 (1991).

Cao, G.Z., "Nitrogen and Phosphorus Doping in CVD Diamond", *Diamond*, edited by M.H. Nazare and A.J. Neves, INSPEC pp. 345-347 (2001).

Chakrabarti et al., "Chemistry of Adamantane. Part II. Synthesis of 1-Adamantyloxyalkylamines", *Tetrahedron Letters* 60:6249-6252 (1968).

"Computation Concepts" *Chem 3D Molecular Modeling and Analysis User's Guide*, Chapter 9, pp. 123-144.

Courtney, T., Johnston, D.E. McKervey, M.A. and Rooney, J.J., "The Chemistry of Diamantanes. Part 1. synthesis and Some Functionalisation Reactions", *J. Chem. Soc. Perkin I* 2691-2696 (1972).

Eguchi et al, "A Novel Route to the 2-Aza-adamantyl System via Photochemical Ring Contraction of Epoxy 4-Azahomoadamantanes", *Journal of Organometallic Chemistry, Commun.*, 1147-1148 (1984).

Fernandez, M.J., et al., "NMR Study of 1-Azatricyclo[3.3.1$^{3-7}$]decane Derivatives", *J. Heterocyclic Chem.* 26:307-312 (1989).

Fernandez, M.J., et al., "Synthesis, Structural and Conformational Study of 4-α-(or β)-p-Chlorobenzoyloxy-1-azaadamantane Hydrochloride", *J. Heterocyclic Chem.* 26:349-353 (1989).

Fleming, I., et al., "A New Oxindole Synthesis", *J. Chem. Soc. Perkin Trans.* 1:617-626 (1991).

Fort, Jr., et al., "Stereochemistry of Hydride Reductions of 4,8-Dihalo-2-thiaadamantanes and Related Thiabicyclo[3.3.1]nonanes", *J. Org. Chem.*52:2396-2399 (1987).

Fox, M.A., et al., "Transmission of Electronic Effects by Icosahedral Carboranes; Skeletal Carbon-13 Cehmical Shifts and Ultraviolet-Visible Spectra of Substituted aryl-p-carboranes (1,12-dicarba-*closo*-dodecaboranes)", *J. Chem. Soc., Dalton Trans.* 401-411 (1998).

Gagneux et al, "1-Substituted 2-Heteroadamantanes", *Tetrahedron Letters* 17: 1365-1368 (1969).

Gerzon, et al., "The Adamantyl Group in Medicinal Agents, 1. Hypoglycemic N-Arylsulfonyl-N-adamantylureas", *Journal of Medicinal Chemistry* 6(6):760-763 (1963).

Hass, et al., Adamantyoxycarbonyl, a New Blocking Group. Preparation of 1-Adamantyl Chloroformate , *Journal of the American Chemical Society* 88(9):1988-1992 (1966).

Hahn, J.M. et al., "Strongly Enhanced Stereoselectivity in the Reduction of of 5-Substituted Adamantanones by Substitution of $C_5$ by Positive Nitrogen", *J. Am. Chem. Soc.* 114:1916-1917 (1992).

Hawley, "Condensed Chemical Dictionary", 14th ed., John Wiley & Sons, Inc., 2001.

Henkel et al, "Neighboring Group Effects in the β-halo Amines. Synthesis and Solvolytic Reactivity of the anti-4-Substituted 2-Azaadamantyl System", *Journal of Organometallic Chemistry* 46:4953-4959 (1981).

Jawdosiuk, M., et al., "Photolysis and Thermolysis of 3-Azidonoradamantane. "Anti-Bredt" Imines, 2-aza-adamant-1-ene, and 4-Azaprotoadamant-3-ene", *J. Chem Soc. Perkin Trans* 1:2583-2585 (1984).

Johnston, C., et al., "Boron Doping and Characterisation of Diamond", *Diamond*, edited by M.H. Nazare and A.J. Neves, INSPEC pp. 337-344 (2001).

Kalish, R., et al., "Doping of Diamond Using Ion Implantation", *Diamond*, edited by M.H. Nazare and A.J. Neves, INSPEC pp 321-330 (2001).

Krasutsky, P.A., et al., "A New One-Step Method for Oxaadamantane Synthesis", *Tetrahedron Letters* 37(32):5673-5674 (1996).

Krasutsky, P.A., et al., "Observation of a Stable Carbocation in a Consecutive Criegee Rearrangement with Trifluoroperacetic Acid", *J. Org. Chem.* 65:3926-3933 (2000).

Krishnamurthy et al, "Heteroadamantanes. 2. Synthesis of 3-Heterodiamantanes", *Journal of Organometallic Chemistry*, 46(7):1389-1390 (1981).

Kurtsiefer, C., et al., "Stable Solid-State Source of single Photons", *Physical Review Letters* 85(2):290-293 (2000).

Lansbury, et al., "Some Reactions of α-Metalated Ethers", *The Journal of Organic Chemistry* 27(6):1933-1939 (1962).

Liaw, D.J, et al., "Synthesis and Characterization of New Polyamides and Polyimides Prepared from 2,2-bis[4-(4-aminophenoxy)phenyl]adamantane", *Macromol. Chem. Phys.* 200(6):1326-1332 (1999).

Lin, et al., "Natural Occurrence of Tetramantane ($C_{22}H_{28}$), Pentamantane ($C_{26}H_{32}$) and Hexamantane ($C_{30}H_{36}$) in a Deep Petroleum Reservoir", *Fuel* 74(10):1512-1521 (1995).

Lippert, E., et al., "Darstellung and UV-Spektren einiger Fluorenon-Derivate", *Angew. Chem.* 71:429-430 (1959).

Makarova, et al., "Psychotropic Activity of Some Aminoketones Belonging to the Adamantane Group" *Pharmaceutical Chemistry Journal* 34:6 (2000).

Marchand, A.P., "Polycyclic Cage Compounds: Reagents, Substrates, and Materials for the 21$^{st}$ Century", *Aldrichimica Acta* 28(4):95-104 (1995).

Marshall et al., "N-Arylsulfonyl-N-alkylureas", *Journal of Organic Chemistry* 23:927-929 (1958).

Marshall et al., "Further studies on N-Arylsulfonyl-N-alkylureas", *Journal of Medicinal Chemistry* 6:60-63 (1963).

McKervey, et al., "Synthetic Approaches to Large Diamondoid Hydrocarbons", *Tetrahedron* 36:9710992 (1980).

Meeuwissen et al, "Synthesis of 1-Phosphaadamantane", *Tetrahedron Letters*, 39(24):4225-4228 (1983).

Mikhailov, B.M., et al., "Organoboron Compounds", *J. Organometallic Chemistry* 250:23-31 (1983).

Moiseev, I.K., et al., "Reactions of Adamantanes in Electrophilic Media", *Russian Chem. Reviews* 68(12):1001-1020 (1999).

Mukherjee; A.K., et al., "On the Stereochemistry of the Oxidation of 5-Phenyl-2-thiaadamantane", *J. Org. Chem.* 58:7955-7957 (1993).

Nordlander et al., "Solvolysis of 1-Adamantylcarbinyl and 3-Homoadamantyl Derivatives. Mechanism of the Neopentyl Cation Rearrangement", *Journal of the American Chemical Society* 88:19 (1966).

Okoroanyanwu, U. et al., "Alicyclic Polymers for 193 nm Resist Applications: Lithographic Evaluation", *Chem. Mater.* 10:3329-3333 (1998).

Park, S., et al., "endo-Fullerene and Doped Diamond Nanocrystallite-Based Models of Qubits for Solid-State Quantum Computers", *J. Nanoscience and Nanotechnology* 1(1):75-81 (2001).

Pasini, D., et al., *Advanced Materials* 12:347-351 (2000).

Prins, J.F., "Large Dopants in Diamond", *Diamond*, edited by M.H. Nazare and A.J. Neves, INSPEC pp 331-336 (2001).

Radziszewski, J.G., et al., "2-Azaadamant-1-ene and 4-Azaprotoadamant-3-ene", *J. Am. Chem.* 106:7996-7998 (1984).

Ramdas, A.K., "A1.2 Modifications to $^{12}$C-diamond by the $^{13}$C-isotope: Raman, Brillouin and Infrared Spectroscopy of Phonons", *INSPEC*, Properties, Growth and Applications of Diamondoids (2001).

Ramdas, A.K., "A1.3 Electronic Excitations in Isotopically Controlled Diamonds: Infrared and Raman Spectroscopy of Acceptor-Bound Holes", *INSPEC*, Properties, Growth and Applications of Diamondoids (2001).

Reinhardt, "Biadamantane and some if its Derivatives", *Journal of Organic Chemistry* 27:3258-3261 (1962).

Risch, N., et al., "Triple (Grob) Gragmentation. Retro-Mannish Reactions of 1-Aza-Adamantane Derivatives", *Tetrahedron Letters* 32(35):4465-4468 (1991).

Risch, N., et al., "Unusual Reorganization Reactions of 3-Azabicycl[3.3.1]nonanes", *J. Am. Chem. Soc.* 113:9411-9412 (1991).

Roberts, P.J., et al., "anti-Tetramantane, a Large Diamondoid Fragment", *Acta. Cryst.* B33:2335-2337 (1977).

Sasaki, T. et al., "New Highly Strained Bridgehead Imines, 2-Azaadamant-1-ene and 4-Azaprotoadamant-3-ene", *Tetrahedron Letters* 23(47):4969-4972 (1982).

Sasaki, T., et al., "Synthesis and Acidolysis of 3-endo-Azidomethyl- and 3-endo-Azido-bicyclo[3.3.1]non-6-enes. A Novel Synthesis of 4-Azahomoadamant-4-enes", *J. Chem. Soc. Perkin Trans 1* 2529-2534 (1983).

Sasaki, T., et al., "Photolytic Generation of Anti-Bredt Imines from 1-Azidobicyclo[2.2.2]octane, 1-Azidobicyclo[3.3.1]nonane, and 3-Azidonoradamantane", *J. Org. Chem.* 48(22):4067-4072 (1983).

Saski, T., et al., "Synthesis of Adamantane Derivatives. 42. Novel Synthesis of 5-Methylene-4-azahomoadamantane Derivatives from 2-Methyl-2-hydroxyadamantane and Their Carbon-13 Nuclear Manetic Resonance Spectra", *J. Org. Chem.* 43(20):3810-3813 (1978).

Sasaki et al., "Synthesis of Adamantane Derivatives. II. Preparation of Some Derivatives from Adamantylacetic Acid", *Bulletin of the Chemical Society of Japan* 41(1):238-240 (1968).

Sasaki et al., "Substitution Reaction of 1-Bromoadamantane in Dimethyl Sulfoxide: Simple Synthesis of 1-Azidoadamantane", *Journal of the American Chemical Society* 92:24 (1970).

Sasaki et al, "Synthesis of Adamantane Derivatives. 39. Synthesis and Acidolysis of 2-Azidoadamantanes. A Facile Route to 4-Azahomoadamant-4-enes", *Heterocycles* 7(1):315-320 (1977).

Sasaki et al, "Synthesis of Adamantane Derivatives. 47. Photochemical Synthesis of 4-Azahomoadamant-4-enes and Further Studies on Their Reactivity in Some Cycloadditions", *Journal of Organometallic Chemistry* 44(21):3711-3712 (1979).

Sasaki, T., et al., "Synthesis of Adamantane Derivatives. XII. The Schmidt Reaction of Adamanatane-2-one", *J. Org. Chem.* 35(12):4109 (1970).

Stetter, et al., "Zur Kenntnis der Adamantan-carbonsaure-(1)", *Uber Verbidugen mit Urotropin-Struktur*, XVII, pp. 1161-1166 (1960).

Stetter, et al., "Ein Beitrag zur Frage der Reaktivitat von Bruckenkopf-Carboniumionen", *Uber Verbindungen mit Urotropin-Struktur XXVI, Chem. Ber.* 96:550-555 (1963).

Stetter, et al., "Neue Moglichkeiten der Direcktsubstitution am Adamantan", *Uber Verbindugen mit Urotropin-Struktur, XLII, Chem. Ber.* 102(10):3357-3363 (1969).

Stetter et al., "Uber Adamantan-phosphonsaure-(1)-dichlorid", *Uber Verbindungen mit Urotropin-Strukture XLIV, Chem. Ber.* 102(10):3364-3366 (1969).

Stetter, et al., "Herstellung von Derivaten des 1-Phenyl-adamantans", *Uber Verbindungen mit Urotropin-Strukture, XXXI, Chem. Ber.* 97(12):3488-3492 (1964).

Stetter, H., et al., Ringschlußreaktionen ausgehend von Bicyclo[3.3.1]nonandion-(3.7) *Uber Verbindungen mit Urotropin-Strukture, XXX* 3480-3487 (1964).

Suginome, H., et al., "The Replacement of the Carbonyl Group of Adamantanone by an Oxygen or sulfur Atom and the One-step Transformation of 2-Methyladamantan-2-ol into 2-Oxa-adamantane; An Efficient New Synthesis of 2-Oxa- and 2-Thiaadamantane", *Synthesis* 741-743 (1986).

Suginome et al, "Photoinduced Transformations. 73. Transformations of Five-(and Six-) Membered Cyclic Alcohols into Five-(and Six-) Membered Cyclic Ethers-A New Method of a Two-Step Transformation of Hydroxy Steroids into Oxasteroids", *Journal of Organometallic Chemistry* 49:3753-3762 (1984).

Udding et al, "A Ring-opening Reaction of and Some Cyclisations to the Adamantane System. A Quasi-favorsky Reaction of a β-bromoketone", *Tetrahedron Letters* 55:5719-5722 (1968).

Verhoeven, J.W.., "From Close contact to Long-Range Intramolecular Electron Transfer", *Intramolecular Electron Transfer*, John Wiley and Sons, pp 603-644 (1999).

von H.U. Daeniker, "206. 1-Hydrazinoadamantan", *Helvetica Chimica Acta* 50:2008-2010 (1967).

Yang, X. et al., "The Synthesis and Structural Characterization fo Carborane Oligomers Connected by Carbon-Carbon and Carbon-Boron Bonds Between Icosahedra", *Inorganica Chimica Acto* 240:371-378 (1995).

FIG. 1

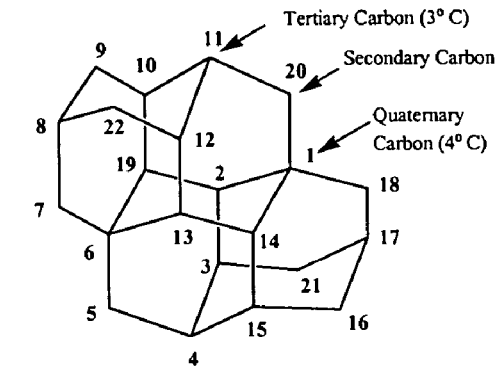

**[121] Tetramantane (*anti-*)**
4 non-equivalent tertiary carbons:

4, 11 (equivalent)
8, 17 (equivalent)
3, 10, 12, 15 (equivalent)
2, 13, 14, 19 (equivalent)

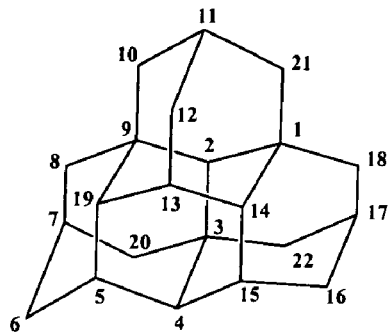

**[1[2]3] Tetramantane (*iso-*)**
4 non-equivalent tertiary carbons:

2
4, 14, 19 (equivalent)
5, 13, 15 (equivalent)
7, 11, 17 (equivalent)

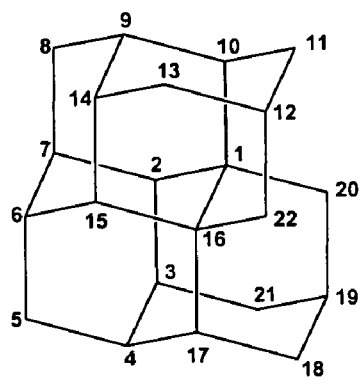

**[123]A Tetramantane (*skew-* A)**
6 non-equivalent tertiary carbons:

6, 7 (equivalent)
4, 9 (equivalent)
3, 14 (equivalent)
2, 15 (equivalent)
10, 17 (equivalent)
12, 19 (equivalent)

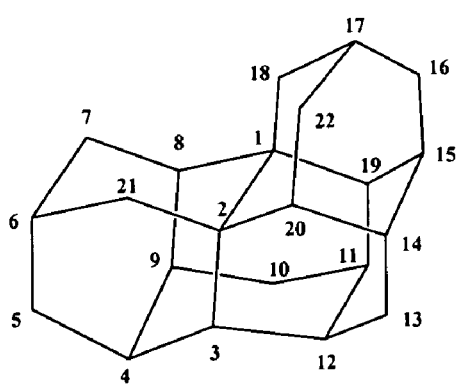

**[123]B Tetramantane (*skew-* B)**
6 non-equivalent tertiary carbons:

6, 17 (equivalent)
4, 15 (equivalent)
11, 12 (equivalent)
3, 19 (equivalent)
9, 14 (equivalent)
8, 20 (equivalent)

| X | | Heat of Formation (Kcal/mol) |
|---|---|---|
| *iso*-Tetramantane | | -52.75 |
| O | C-2 | -78.57 |
| S | C-2 | -35.22 |
| Se | C-2 | -31.26 |
| B | C-2 | -18.40 |
|   | C-3 | -9.32 |
| N | C-2 | -34.28 |
|   | C-3 | --26.94 |
| P | C-2 | -16.19 |
|   | C-3 | -15.85 |
| As | C-2 | -20.68 |
|   | C-3 | -18.63 |

Representative Ways of Generation of Heterodiamondoid Cations

Representative $S_N1$ Reactions of Heterodiamondoid Carbocations

Representative $S_E2$ Reactions of Heterodiamondoids

FIG. 24
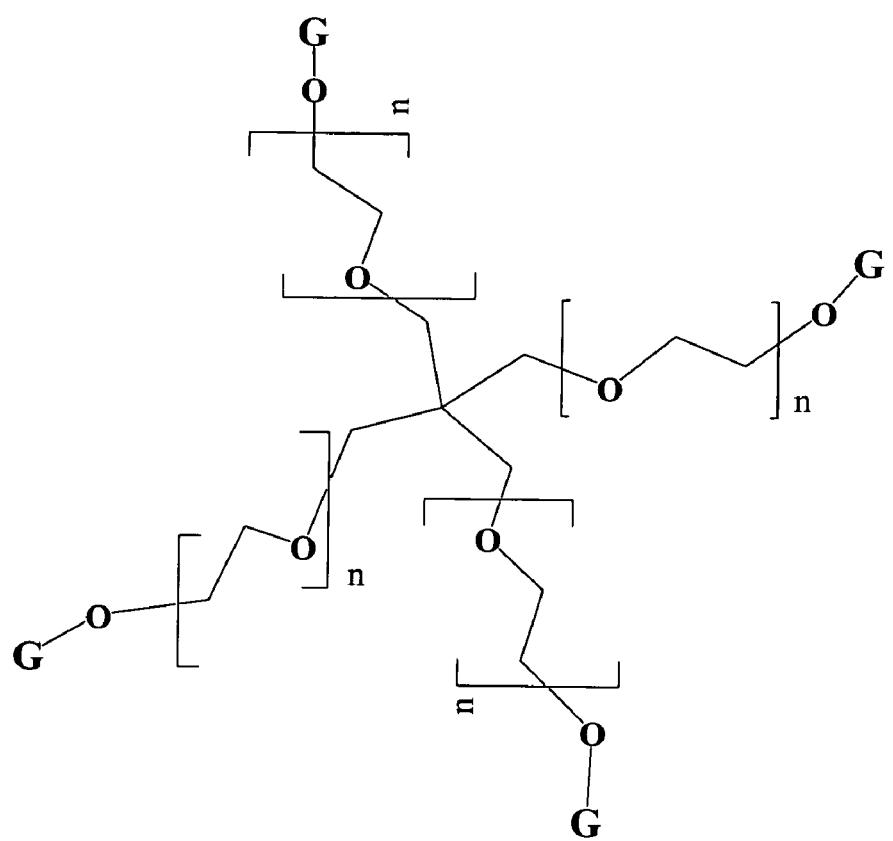
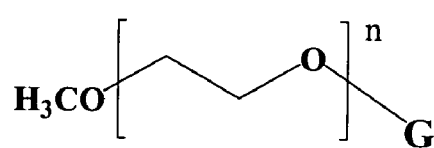 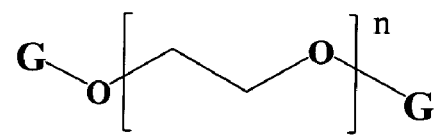

FIG. 30
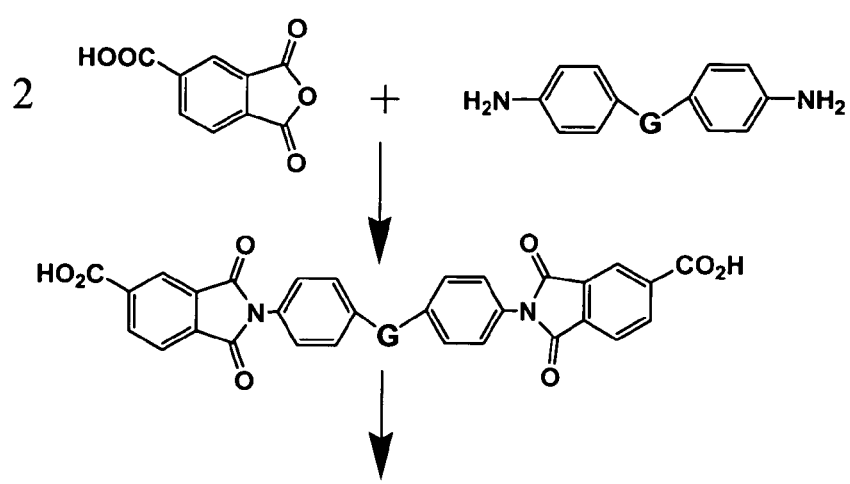
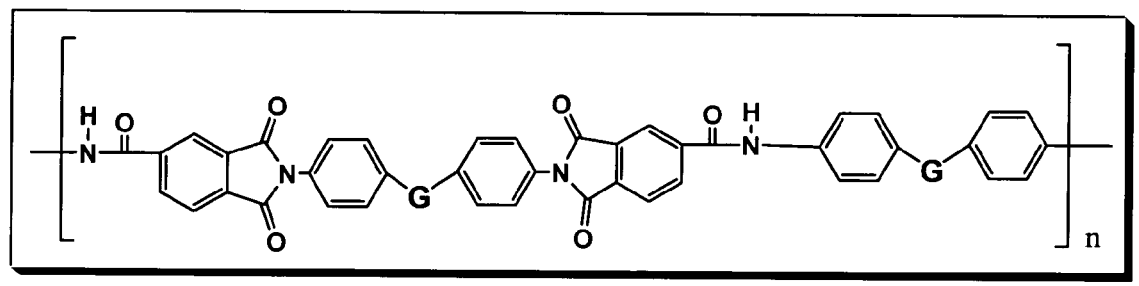

HETERODIAMONDOIDS

This application claims priority under 35 U.S.C. § 119 to U.S. Provisional Application No. 60/397,367 entitled Heterodiamondoids and filed on Jul. 18, 2002, the entire content of which is hereby incorporated by reference.

BACKGROUND OF THE INVENTION

1. Field of the Invention

This invention relates to heteroatom-containing diamondoids (i.e., "heterodiamondoids") which are compounds having a diamondoid nucleus in which one or more of the diamondoid nucleus carbons has been substitutionally replaced with a noncarbon such as a group IIIB, noncarbon group IVB, group VB or VIB atom. (Groups are based on the previous IUPAC Periodic Table groups as referenced in Hawley's *Condensed Chemical Dictionary*, 14$^{th}$ ed. John Wiley & Sons, Inc, 2001.) These heteroatom substituents impart desirable properties to the diamondoid. In addition, the heterodiamondoids can be functionalized affording compounds carrying one or more functionalization groups covalently pendant therefrom. Functionalized heterodiamondoids having polymerizable functional groups are able to form polymers containing heterodiamondoids.

In a preferred aspect the diamondoid nuclei are triamantane and higher diamondoid nuclei. In another preferred aspect, the heteroatoms are selected to give rise to diamondoid materials which can serve as n- and p-type materials in electronic devices.

2. Background Information

Diamondoids are cage-shaped hydrocarbon molecules possessing rigid structures which are tiny fragments of a diamond crystal lattice. Adamantane is the smallest member of the diamondoid series and consists of a single cage structure of the diamond crystal lattice. Diamantane contains two adamantane subunits face-fused to each other, triamantane three, tetramantane four, and so on. While there is only one isomeric form of adamantane, diamantane and triamantane, there are four different isomeric tetramantanes (i.e., four different shapes containing four adamantane subunits). Two of the isomeric tetramantanes are enantiomeric. The number of possible isomers increases rapidly with each higher member of the diamondoid series.

Adamantane, which is commercially available, has been functionalized. For instance, U.S. Pat. No. 3,832,332 describes a polyamide polymer formed from alkyladamantane diamine; U.S. Pat. No. 5,017,734 discusses the formation of thermally stable resins from ethynyl adamantane derivatives; and, U.S. Pat. No. 6,235,851 reports the synthesis and polymerization of a variety of adamantane derivatives.

The following references related to adamantane and derivatives formed from adamantane:

Capaldi, et al., Alkenyl Adamantanes, U.S. Pat. No. 3,457,318, issued Jul. 22, 1969

Thompson, Polyamide Polymer of Diamino Methyl Adamantane and Dicarboxylic Acid, U.S. Pat. No. 3,832,332, issued Aug. 27, 1974

Baum, et al., Ethynyl Adamantane Derivatives and Methods of Polymerization Thereof, U.S. Pat. No. 5,017,734, issued May 21, 1991

Ishii, et al., Polymerizable Adamantane Derivatives and Process for Producing Same, U.S. Pat. No. 6,235,851, issued May 22, 2001

McKervey, et al., *Synthetic Approaches to Large Diamondoid Hydrocarbons*, Tetrahedron 36, 971–992 (1980)

Lin, et al., *Natural Occurrence of Tetramantane* ($C_{22}H_{28}$), *Pentamantane* ($C_{26}H_{32}$) *and Hexamantane* ($C_{30}H_{36}$) *in a Deep Petroleum Reservoir*, Fuel 74:10, 1512–1521 (1995)

Chen, et al., Isolation of High Purity Diamondoid Fractions and Components, U.S. Pat. No. 5,414,189, issued May 9, 1995

Balaban et al., *Systematic Classification and Nomenclature of Diamond Hydrocarbons—I*, Tetrahedron 34, 3599–3606 (1978)

Gerzon et al., *The Adamantyl Group in Medicinal Agents, 1. Hypoglycemic N-Arylsulfonyl-N-adamantylureas*, Journal of Medicinal Chemistry 6 (6), 760–763 (November 1963)

Marshall et al., *Further Studies on N-Arylsulfonyl-N-alkylureas*, Journal of Medicinal Chemistry 6, 60–63 (January 1963)

Marshall et al., *N-Arylsulfonyl-N-alkylureas*, Journal of Organic Chemistry 23, 927–929 (June 1958)

Reinhardt, *Biadamantane and Some of its Derivatives*, Journal of Organic Chemistry 27, 3258–3261, (September 1962)

Sasaki et al., *Synthesis of Adamantane Derivatives. II. Preparation of Some Derivatives from Adamantylacetic Acid*, Bulletin of the Chemical Society of Japan 41:1, 238–240 (June 1968)

Stetter et al, *Ein Beitrag zur Frage der Reaktivitat von Bruckenkopf-Carboniumionen, Uber Verbindungen mit Urotropin-Struktur, XXVI*, Chem. Ber. 96 550–555, (1963)

Hass et al, *Adamantyloxycarbonyl, a New Blocking Group. Preparation of 1-Adamantyl Chloroformate*, Journal of the American Chemical Society 88:9, 1988–1992 (May 5, 1966)

Stetter et al, *Neue Moglichkeiten der Direktsubstitution am Adamantan, Uber Verbindungen mit Urotropin-Struktur, XLIII*, Chem. Ber. 102 (10), 3357–3363 (1969)

von H. U. Daeniker, 206. *1-Hydrazinoadamantan*, Helvetica Chimica Acta 50, 2008–2010 (1967)

Stetter et al, Uber *Adamantan-phosphonsaure-(1)-dichlorid, Uber Verbindungen mit Urotropin-Struktur, XLIV*, Chem. Ber. 102 (10), 3364–3366 (1969)

Lansbury et al, *Some Reactions of α-Metalated Ethers*, The Journal of Organic Chemistry 27:6, 1933–1939 (Jun. 12, 1962)

Stetter et al, *Herstellung von Derivaten des 1-Phenyladamantans, Uber Verbindungen mit Urotropin-Struktur, XXXI*, Chem. Ber. 97 (12), 3488–3492 (1964)

Nordlander et al, *Solvolysis of 1-Adamantylcarbinyl and 3-Homoadamantyl Derivatives. Mechanism of the Neopentyl Cation Rearrangement*, Journal of the American Chemical Society 88:19 (Oct. 5, 1966)

Sasaki et al, Substitution *Reaction of 1-Bromoadamantane in Dimethyl Sulfoxide: Simple Synthesis of 1-Azidoadamantane*, Journal of the American Chemical Society 92:24 (Dec. 2, 1970)

Chakrabarti et al, *Chemistry of Adamantane. Part II. Synthesis of 1-Adamantyloxyalkylamines*, Tetrahedron Letters 60, 6249–6252 (1968)

Stetter et al, *Derivate des 1-Amino-adamantans, Uber Verbindungen mit Urotropin-Struktur, XXIV*, Chem. Ber. 95, 2302–2304 (1962)

Stetter et al, *Zur Kenntnis der Adamantan-carbonsaure, Uber Verbindungen mit Urotropin-Struktur, XVII*, Chem. Ber. 93, 1161–1166 (1960)

Makarova et al, *Psychotropic Activity of Some Aminoketones Belonging to the Adamantane Group*, Pharmaceutical Chemistry Journal, 34:6 (2000)

As noted above, heterodiamondoids are those diamondoids in which at least one cage carbon atom is replaced by a heteroatom. The following references describe more details about heteroadamantanes and heterodiamantanes.

Meeuwissen et al, *Synthesis of 1-Phosphaadamantane*, Tetrahedron Letters, 39:24, 4225–4228 (1983)

Boudjouk et al, *The Reaction of Magnesium with cis-1,3,5-Trsi(bromomethyl)cyclohexane. Evidence For a Soluble Tri-grignard*, Journal of Organometallic Chemistry 281, C21–C23 (1985)

Boudjouk et al, *Synthesis and Reactivity of 1-Silaadamantyl Systems*, Journal of Organometallic Chemistry 2, 336–343 (1983).

Krishnamurthy et al, *Heteroadamantanes. 2. Synthesis of 3-Heterodiamantanes*, Journal of Organometallic Chemistry, 46:7, 1389–1390 (1981)

Udding et al, *A Ring-opening Reaction of and Some Cyclisations to the Adamantane System. A Quasi-favorsky Reaction of a β-bromoketone*, Tetrahedron Letters 55, 5719–5722 (1968)

Blaney et al, *Chemistry of Diamantane, Part II. Synthesis of 3,5-disubstituted Derivatives*, Synthetic Communications 3:6, 435–439 (1973)

Henkel et al, *Neighboring Group Effects in the β-halo Amines. Synthesis and Solvolytic Reactivity of the anti-4-Substituted 2-Azaadamantyl System*, Journal of Organometallic Chemistry 46, 4953–4959 (1981)

Becker et al, *A Short Synthese of 1-azaadamantan-4-one and the 4r and 4s Isomers of 4-Amino-1-azaadamantane*, Synthesis, (11), 1080–1082 (1992)

Eguchi et al, *A Novel Route to the 2-Aza-adamantyl System via Photochemical Ring Contraction of Epoxy 4-Azahomoadamantanes*, Journal of Organometallic Chemistry, Commun., 1147–1148 (1984)

Gagneux et al, *1-Substituted 2-Heteroadamantanes*, Tetrahedron Letters 17, 1365–1368 (1969)

Bubnov et al, *A Novel Method of Synthesis of 1-azaadamantane from 1-boraadamantane*, Journal of Organometallic Chemistry 412, 1–8 (1991).

Sasaki et al, *Synthesis of Adamantane Derivatives. 39. Synthesis and Acidolysis of 2-Azidoadamantanes. A Facile Route to 4-Azahomoadamant-4-enes*, Heterocycles 7:1 315–320 (1977)

Sasaki et al, *Synthesis of Adamantane Derivatives. 47. Photochemical Synthesis of 4-Azahomoadamant-4-enes and Further Studies on Their Reactivity in Some Cycloadditions*, Journal of Organometallic Chemistry, 44:21, 3711–3712 (1979)

German Patent No. DE 2,545,292 issued April, 1979

Suginome et al, *Photoinduced Transformations. 73. Transformations of Five-(and Six-) Membered Cyclic Alcohols into Five-(and Six-) Membered Cyclic Ethers—A New Method of a Two-Step Transformation of Hydroxy Steroids into Oxasteroids*, Journal of Organometallic Chemistry 49, 3753–3762, (1984)

Adamantane and substituted adamantane are the only readily available diamondoids. Diamantane and triamantane and substituted diamantanes have been studied, and only a single tetramantane has been synthesized. The remaining diamondoids were provided for the first time by the inventors Dahl and Carlson, and are described for example, in U.S. Patent Application Ser. No. 60/262,842 filed Jan. 19, 2001 and PCT US02/00505 filed Jan. 17, 2002.

SUMMARY OF THE INVENTION

The invention provides heterotriamantanes and hetero higher diamondoids. Heteroatoms are selected from atoms of group IIIB elements such as B or Al; noncarbon group IVB elements such as Si; group VB elements such as N, P or As, and particularly N or P; and group VIB elements such as O, S, or Se. It will be noted that the group VB elements are generally classed as electron-donating (hole-accepting) or "electropositive" atoms and the group IIIB elements are generally classed as electron-accepting (hole-donating) or "electronegative" atoms.

These heterodiamondoids of the invention are a triamantane or a higher diamondoid nucleus with 1 or more (for example 1 to 20 and especially 1 to 6) of its cage carbons replaced by a heteroatom. The heterodiamondoids can also be substituted with up to 6 alkyl groups per diamondoid unit.

This invention is further directed to functionalized heterodiamondoids. In this embodiment the heterotriamantanes and higher heterodiamondoids contain at least 1 and, preferably 1 to 6 functional group(s) covalently bonded to cage carbons, presented as Formula I:

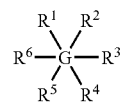

I wherein, G is a heterotriamantane or a higher heterodiamondoid nucleus with one or more heteroatoms as described; and, $R^1$, $R^2$, $R^3$, $R^4$, $R^5$ and $R^6$ are each independently selected from a group consisting of hydrogen and covalently bonded functional groups, provided that there is at least 1 functional group. More preferably, the functionalized heterodiamondoids contain either 1 or 2 functional groups and from 1 to 6 heteroatoms.

These heterodiamondoids and functionalized heterodiamondoids can exist as discrete individual molecules. They can also exist as crystalline aggregates. These crystalline structures can be pure heterodiamondoids or pure functionalized heterodiamondoids or can, intentionally or inadvertendly, be a mixture of more than one diamondoid with or without functionalization, with heterodiamondoid and/or functionalized heterodiamondoid.

Some of these functionalized heterodiamondoids can be prepared from heterodiamondoids in a single reaction step. These materials are referred to herein as "primary functionalized heterodiamondoids" and include, for example, heterodiamondoids of Formula I wherein the functionalizing groups are halogens (such as -bromos, and -chloros), -thios, -oxides, -hydroxyls, and -nitros, as well as other derivatives formed in one reaction from a heterotriamantane or a higher heterodiamondoid.

Others of these functionalized heterodiamondoids are materials prepared from a primary functionalized heterodiamondoids by one or more subsequent reaction steps. These materials are referred to herein as "secondary functionalized heterodiamondoids." It will be appreciated that in some cases one primary functionalized heterodiamondoid may be conveniently formed by conversion of another "primary" material. For example, a poly-bromo material can be formed either by single step bromination or by several repeated brominations. Similarly, a hydroxyl heterodiamondoid can be formed directly from a heterodiamondoid in one step or can be prepared by reaction of a bromo-heterodiamondoid, a diamondoid-oxide or the like. Notwithstanding this, to avoid confusion, the "primary" materials will not be included here in the representative secondary materials. They will, however, be depicted in various figures showing reactions for forming primary and secondary materials to depict both routes to them.

Representative "secondary functionalized heterodiamondoid" functional groups include haloalkyl, haloalkenyl, haloalkynyl, hydroxyalkyl, heteroaryl, alkylthio, alkoxy; aminoalkyl, aminoalkoxy, heterocycloalkoxy, cycloalkyloxy, aryloxy, and heteroaryloxy.

Other functional groups that can be present in the secondary functionalized heterodiamondoids are represented by the formula —C(O)Z wherein Z is hydrogen, alkyl, halo, haloalkyl, halothio, amino, monosubstituted amino, disubstituted amino, cycloalkyl, aryl, heteroaryl, heterocyclic; —CO$_2$Z wherein Z is as defined previously; —R$^7$COZ and —R$^7$CO$_2$Z wherein R$^7$ is alkenyl aminoalkenyl, or haloalkenyl and Z is as defined previously; —NH$_2$; —NHR', —NR'R", —N$^+$R'R"R'" wherein R', R", and R'" are independently alkyl, amino, thio, thioalkyl, heteroalkyl, aryl, or heteroaryl; —R$^8$NHCOR$^9$ wherein R$^8$ is —CH$_2$—, —OCH$_2$—, —NHCH$_2$—, —CH$_2$CH$_2$—, —OCH$_2$CH$_2$— and R$^9$ is alkyl, aryl, heteroaryl, aralkyl, or heteroaralkly; and —R$^{10}$CONHR$^{11}$— wherein R$^{10}$ is selected from —CH$_2$—, —OCH$_2$—, —NHCH$_2$—, —CH$_2$CH$_2$—, and —OCH$_2$CH$_2$—, and R$^{11}$ is selected from hydrogen, alkyl, aryl, heteroaryl, aralkyl, and heteroaralkyl.

In a further preferred embodiment, the functional group on the functionalized heterodiamondoid is —COOR$^{16}$ wherein R$^{16}$ is alkyl, aryl, or aralkyl; —COR$^7$, wherein R$^{17}$ is alkyl, aryl, or heteroalkyl; —NHNH$_2$; —R$^{18}$NHCOR$^{19}$ wherein R is absent or selected from alkylene, arylene, or aralkylene, R$^{19}$ is hydrogen, alkyl, —N$_2$, aryl, amino, or —NHR$^{20}$ wherein R$^{20}$ is hydrogen, —SO$_2$-aryl, —SO$_2$-alkyl, —SO$_2$-aralkyl or —CONHR$^{21}$ wherein R$^{21}$ is hydrogen, alkyl, aralkyl, or —CSNHR$^{21}$ wherein R$^{21}$ is as defined above; and —NR$^{22}$—(CH$_2$)$_n$—NR$^{23}$R$^{24}$, wherein R$^{22}$, R$^{23}$, R$^{24}$ are independantly selected from hydrogen, alkyl, and aryl, and n is from 1 to 20.

In an additional embodiment, the functional group on the functionalized heterodiamondoid may be independently selected from —N=C=S; —N=C=O; —R—N=C=O; —R—N=C=S; —N=S=O; R—N=S=O wherein R is alkyl; —PH$_2$; —POX$_2$ wherein X is halo; —PO(OH)$_2$; halo; —OSO$_3$H; —SO$_2$H; —SOX wherein X is halo; —SO$_2$R wherein R is alkyl; —SO$_2$OR wherein R is alkyl; —SONR$^{26}$R$^{27}$ wherein R$^{26}$ and R$^{27}$ are independently hydrogen or alkyl; —N$_3$; —OC(O)Cl; or —OC(O)SCl.

In further an additional embodiment, one or more of the functional groups on the functionalized heterodiamondoids may be of the formula:

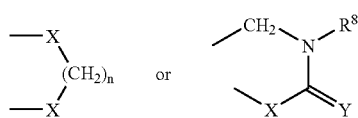

wherein n is 2 or 3; X is oxygen, sulfur, or carbonyl; Y is oxygen or sulfur; and R$^8$ is selected from the group consisting of hydrogen, alkyl, heteroalkyl, aryl, and heteroaryl.

In a further aspect, the functionalizing group may form a covalent bond to two or more of these heterodiamondoids and thus serve as a linking group or polymerizable group between the two or more heterodiamondoids. This provides functionalized heterodiamondoids of formula II:

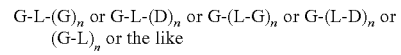

wherein D is a diamondoid nucleus, G is a heterotriamantane or a higher heterodiamondoid nucleus and L is a linking group and n is 1 or more such as 2 to 1000 and especially 2 to 500.

In this embodiment, the linking group L may be, for example, aryls, alkenyls, alkynyls, esters, amides, —N=C—N—;

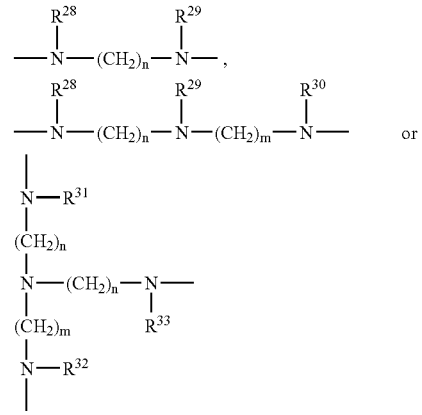

wherein R$^{28}$, R$^{29}$, R$^{30}$, R$^{31}$, R$^{32}$, R$^{33}$ are independently hydrogen or alkyl, and n and m are independently from 2 to 20;

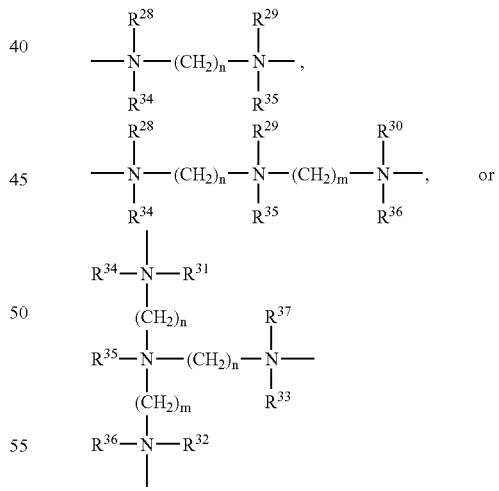

wherein R$^{28}$, R$^{29}$, R$^{30}$, R$^{31}$, R$^{32}$, and R$^{33}$ are hydrogen or alkyl; R$^{34}$, R$^{35}$, R$^{36}$, and R$^{37}$ are independently absent or hydrogen or alkyl with the proviso that at least one of R$^{34}$, R$^{35}$, R$^{36}$, and R$^{37}$ is present; and n and m are independently from 2 to 20 or the like.

In another aspect, the present invention relates to functionalized heterodiamondoids of formula III:

wherein G and G' are each independently a heterodiamondoid nucleus and R' and R" are substituents on the heterodiamondoid nucleus and are independently hydrogen or a functionalizing group. n and m are 1 or more such as 1 to 10 and preferably 1 to 6. More preferably the material contains either 1 or 2 functional groups. Preferably R' and R" are halo; cyano; aryl; arylalkoxy; aminoalkyl; or —COOR$^{40}$ wherein R$^{40}$ is hydrogen or alkyl.

The heterodiamondoids and functionalized heterodiamondoids of the present invention are useful in for instance, nanotechnology, drugs, drug carriers, pharmaceutical compositions, precursors for the synthesis of biologically active compounds, photoresist materials and/or photoresist compositions for far UV lithography, synthetic lubricants, heat resist materials and solvent-resistant resins, and so on. For example, these heterodiamondoid derivatives may have desirable lipophilic properties, which may improve the bioavailability of pharmaceutically active groups attached thereto. These heterodiamondoids and derivatives may also be useful as chemical intermediates for the synthesis of further functionalized heterodiamondoids to form a variety of useful materials. Such materials include composite matrix resins, structural adhesives and surface files that are used for aerospace structural applications. Furthermore, coating layers or molded products with excellent optical, electrical or electronic and mechanical properties are produced for use in optical fibers, photoresist compositions, conduction materials, paint compositions and printing inks. In addition, these heterodiamondoid derivative-containing materials will have high thermal stability making them suitable for use in environments requiring such stability including for example, devices such as semiconductors, coatings for refractory troughs or other high temperature applications.

In applications of particular importance, the heteroatoms introduced into the triamantane of higher diamondoid nucleus are electron-donating or electron-accepting. The semiconducting heterodiamondoids that result have utility in a variety of transistor and other electronic and microelectronic settings.

In addition, when the heteroatoms in the heterodiamondoids are electron-donating, and particularly nitrogen, this gives rise to the possibility that the donated electrons can be excited from the normal valence bond through a bond gap into a conductive bond. When the excited electrons decay back to their base state, particularly if a vacancy is adjacent to the electron-donating heteroatom, a photon can be emitted. This suggests that these hetrodiamondoids could have properties to provide molecular size and crystallite-sized flouresent species, lasing species and photodetecting species. (See Kurtsiefer, C, et al *Stable Solid-State Source of Single Photons, Physical Review Letters* 85, 2, 290–293 (2000).

BRIEF DESCRIPTION OF THE DRAWINGS

This invention will be further described with reference to the drawings in which:

FIG. 1 shows the numbering of four tetramantanes and points out representative secondary, tertiary and quaternary carbon atoms.

FIGS. 24–33 illustrate representative polymers containing heterodiamondoids and routes to prepare them.

DETAILED DESCRIPTION OF THE INVENTION

Figure 2:
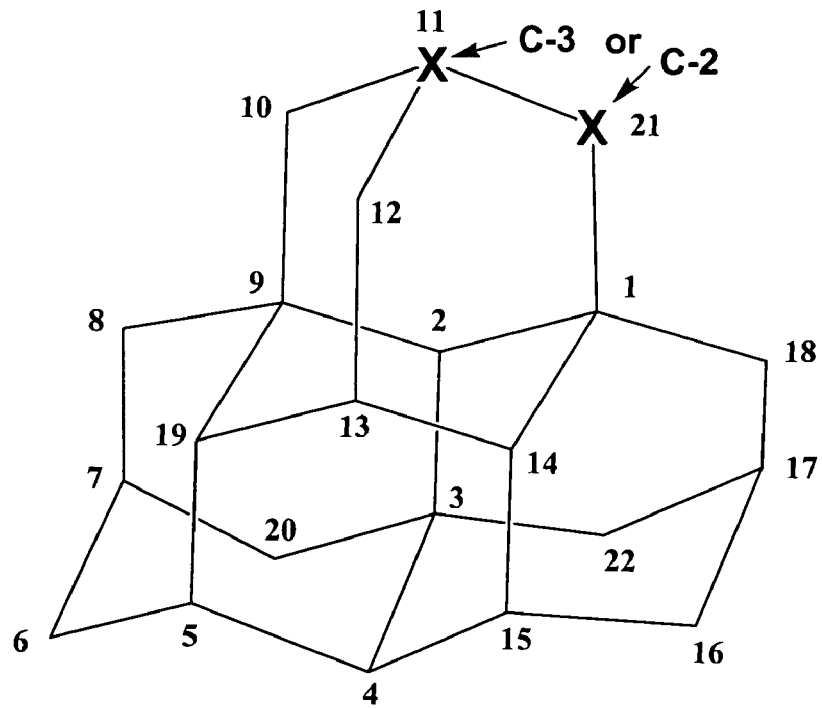
FIG. 2 presents exemplary computer modeling calculations that illustrate the feasibility of the synthesis of heterodiamondoids.

This detailed description is presented in the following subsections:
Definitions
Synthesis of Heterodiamondoids
Functionalization of Heterodiamondoids and Derivatives Therefrom
Heterodiamondoid-Containing Polymers Definitions As used herein, the following terms have the following meanings.

The term "diamondoid" is given a special meaning. It refers to substituted and unsubstituted caged compounds of the adamantane series beginning with triamantane and including, in addition, tetramantane, pentamantane, hexamantane, heptamantane, octamantane, nonamantane, decamantane, undecamantane and dodecamantane. A higher diamondoid is tetramantane or higher. Substituted diamondoids preferably comprise from 1 to 10 and more preferably 1 to 4 substituents independently selected from the group consisting of alkyl, including linear (i.e., straight chain) alkyl, branched alkyl or cycloalkyl groups.

The term "heteroatom" refers to an atom selected from IIIB, non-C IVB, VB and VIB elements in the Periodic Table of the Elements, e.g. B, Al, Si, N, P, As, O, S, etc.

The terms "heterodiamondoid" and "hetero diamondoid" refer to diamondoid (as specifically defined) in which at least one cage carbon atom is replaced by a heteroatom. Heterodiamondoids include heterotriamantane, heterotetramantane, heteropentamantane, heterohexamantane, heteroheptamantane, heterooctamantane, heterononamantane, heterodecamantane, heteroundecamantane, heteroundecamantane and heterododecamantane. Substituted heterodiamondoids preferably comprise from 1 to 10 and more preferably 1 to 4 substituents independently selected from the group consisting of alkyl, including linear (i.e., straight chain) alkyl, branched alkyl or cycloalkyl groups.

The terms "functionalized heterodiamondoid" and "derivatized heterodiamandoid" refer to a heterodiamondoid which has at least one covalently bonded functional group.

The term "alkyl" refers to a linear saturated monovalent hydrocarbon group having 1 to 40 carbon atoms, preferably 1 to 10 carbon atoms, more preferably 1 to 6 carbon atoms; or a branched saturated monovalent hydrocarbon group having 3 to 40 carbon atoms, preferably from 3 to 10 carbon atoms, and more preferably 3 to 6 carbon atoms. This term is exemplified by groups such as methyl, ethyl, n-propyl, iso-propyl, n-butyl, iso-butyl, n-hexyl, n-decyl, tetradecyl, and the like.

The term "functional group" refers to halos, hydroxyls, oxides, nitros, aminos, thios, sulfonyl halides, sulfonates, phosphines and the like, as well as such groups attached to hydrocarbyl materials such as alkyls, alkenyls, alkyaryls and aryls with or without substitution.

Synthesis of Heterodiamondoids

Prior to attempting an actual synthesis, it is often advantageous to utilize the methods of molecular modeling and computational chemistry in order to predict the properties of a desired molecule, and to facilitate the design of a synthetic pathway. These methods calculate the potential energy surface of a molecule, which takes into account the forces of interaction between the constituent atoms.

After optimizing the molecular structure and calculating the minimized energy, the heat of formation was calculated. The results of an exemplary calculation for the hetero-iso-tetramantane are provided in the table shown in FIG. 2. In FIG. 2, "X" represents a heteroatom that has been inserted into the diamond lattice substitutionally. The second column of the table denotes the position where the heteroatom replaces a host carbon atom, and these positons are either denoted "C-2" for secondary positions, or "C-3" for tertiary positions. Identification of secondary and tertiary positions is shown with four representative diamondoids in FIG. 1 and FIG. 2. The third column of the table are the heats of formation in kcal/mol.

The present calculations serve to demonstrate that the preparation of such compounds is synthetically feasible.

A similar set of calculations was made for the hetero-[121212121] decamantane, with the results shown in Table 1:

TABLE 1

| Heteroatom (X) | Position | Heat of formation (Kcal/mol) |
|---|---|---|
| C |  | −76.08 |
| O | C-2 | −103.45 |
| S | C-2 | −58.71 |
| Se | C-2 | −53.26 |
| B | C-2 | −42.40 |
|  | C-3 | −31.76 |
| N | C-2 | −56.91 |
|  | C-3 | −48.15 |
| P | C-2 | −28.44 |
|  | C-3 | −27.10 |
| As | C-2 | −43.59 |
|  | C-3 | −44.52 |

Similar to the example above, those calculations indicate that the synthesis of the heterodiamondoids are feasible.

A final example of a calculation is presented for hetero-[1212121212] undecamantane. For this particular isomer, the results of the calculations are shown in Table 2. In this example, the substitution is made at either the secondary C-2 atom at position 25, or the C-3 atom at position 26. The results of the calculation are shown in Table 2:

TABLE 2

| Heteroatom (X) | Position | Heat of formation (Kcal/mol) |
| --- | --- | --- |
| C |  | −79.81 |
| O | C-2 | 106.92 |
| S | C-2 | 61.95 |
| Se | C-2 | 56.82 |
| B | C-2 | −45.45 |
|  | C-3 | −35.85 |
| N | C-2 | −60.32 |
|  | C-3 | −52.45 |
| P | C-2 | −32.05 |
|  | C-3 | −29.80 |
| As | C-2 | −47.70 |
|  | C-3 | −47.96 |

Once again, the calculations indicate that the synthesis is feasible.

Thus, molecular modeling calculations have demonstrated that it is feasible to substitutionally position a boron, nitrogen, phosphorus, arsenic, oxygen, or sulfur heteroatom into the diamond lattice of a diamondoid.

Figure 3:
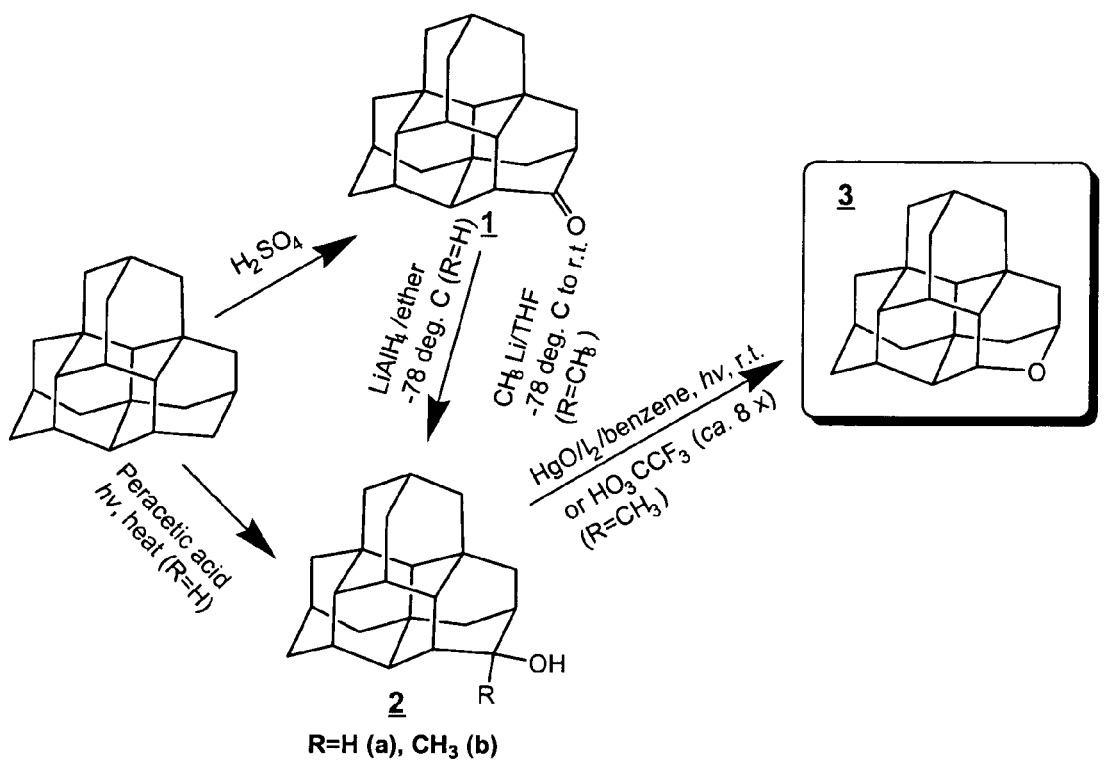
FIGS. 3–5 illustrate reaction routes for introducing an oxygen heteroatom into a diamondoid.
Figure 4:
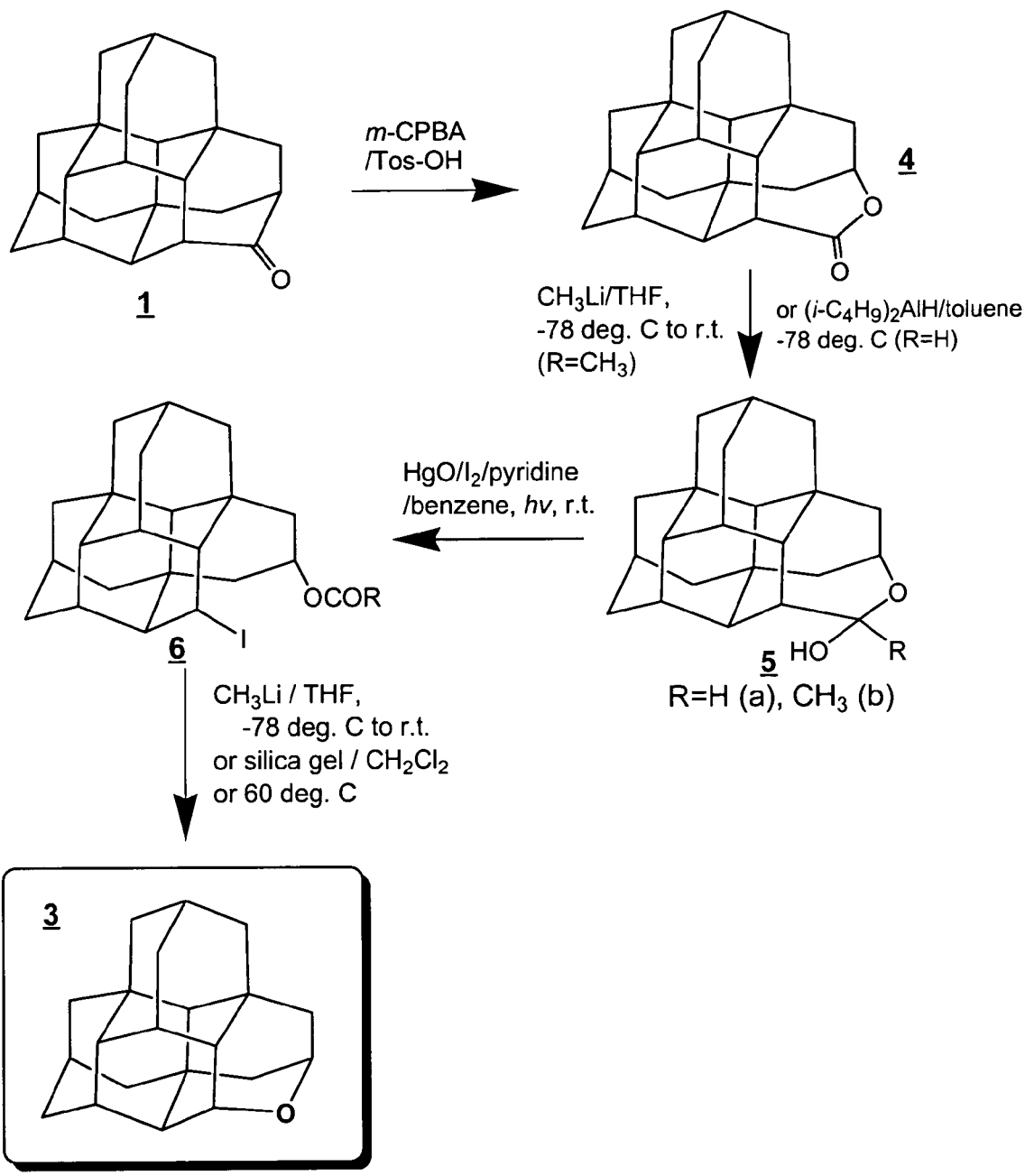
Figure 5:
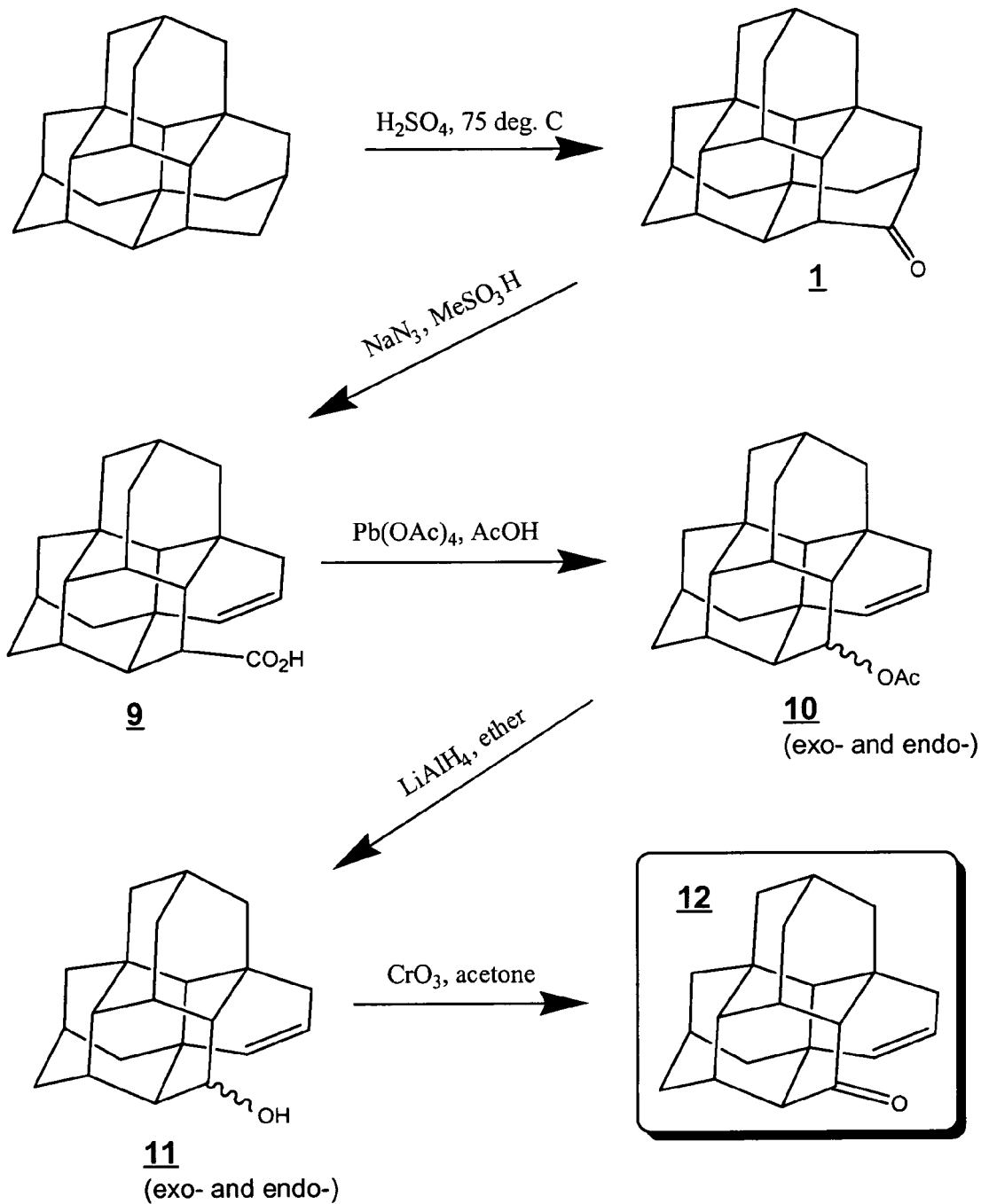
Figure 5:
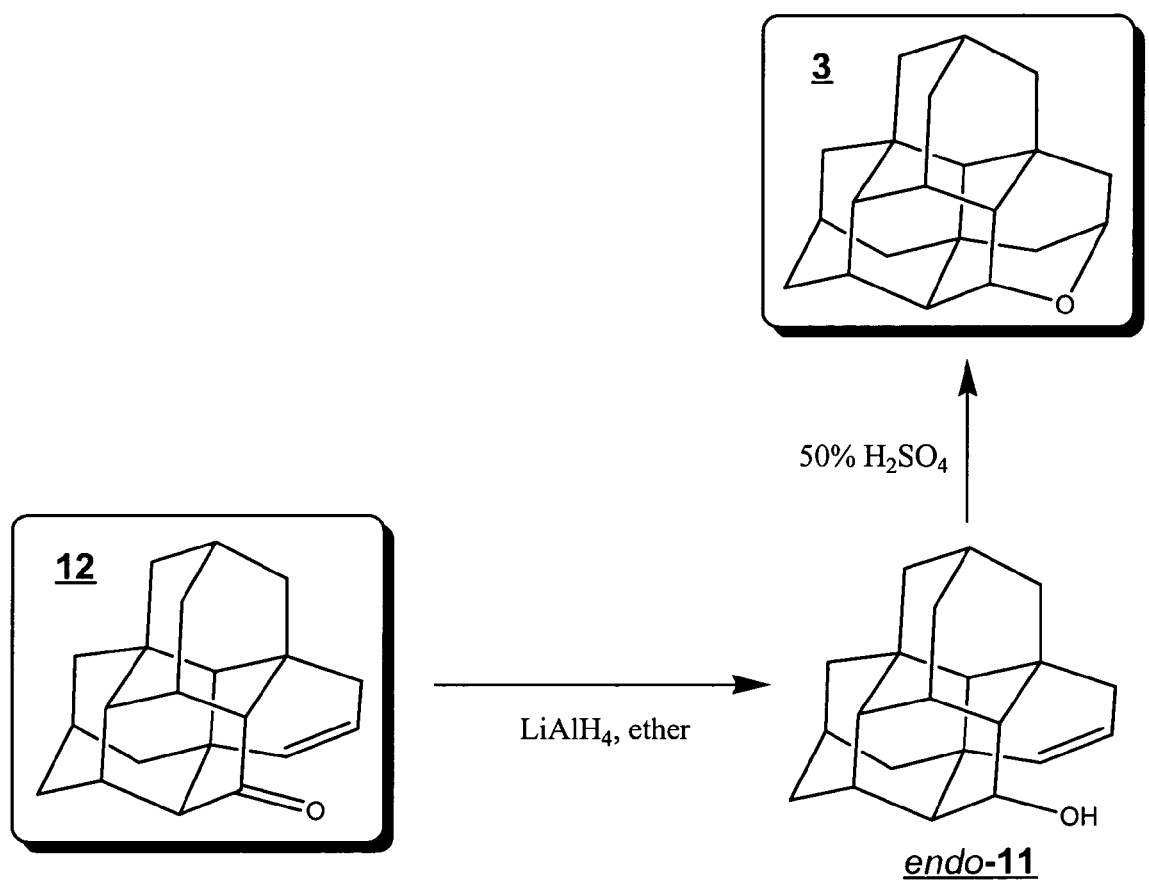
Figure 6:
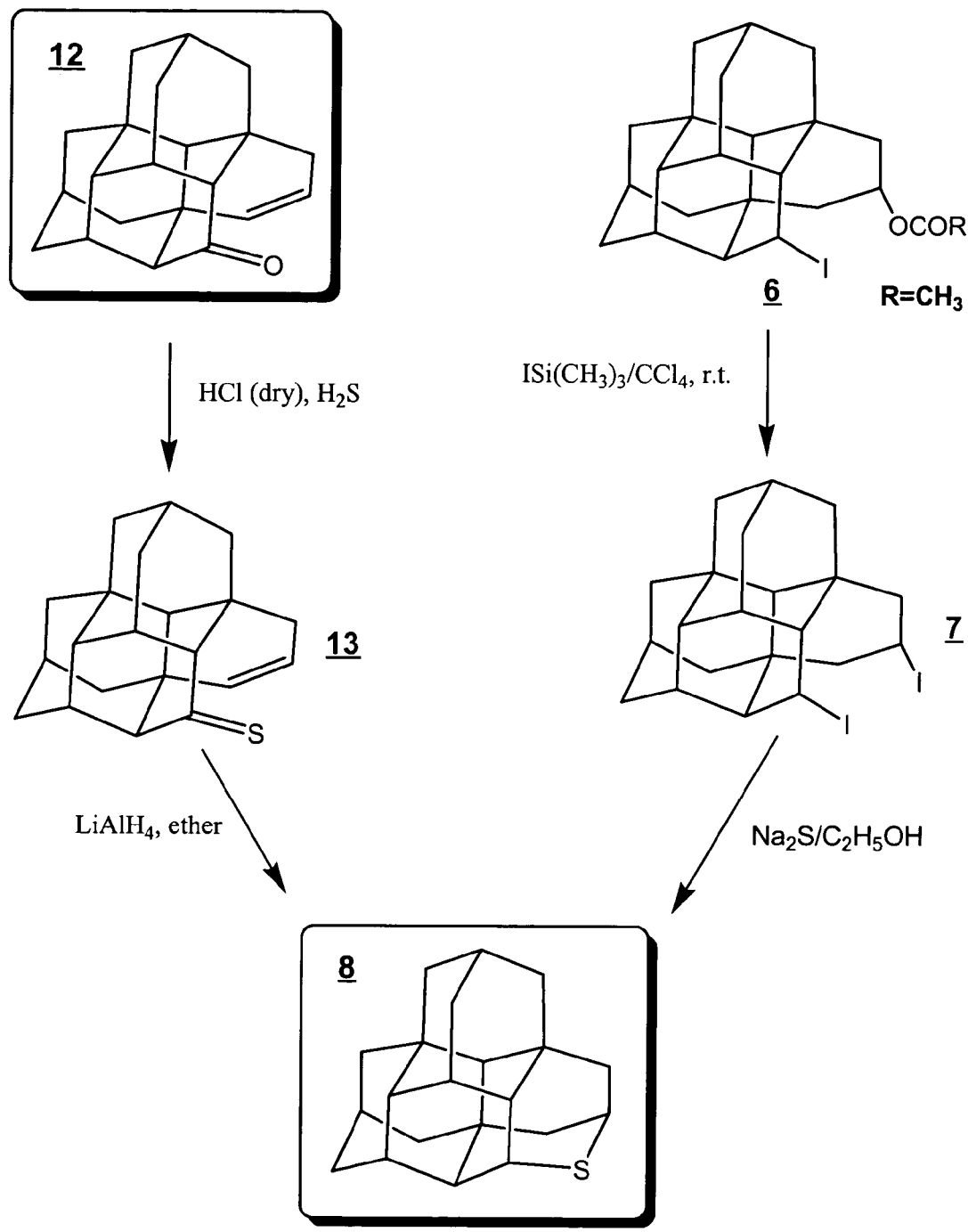
FIG. 6 illustrates routes for introducing a sulfur heteroatom into a diamondoid.
Figure 7:
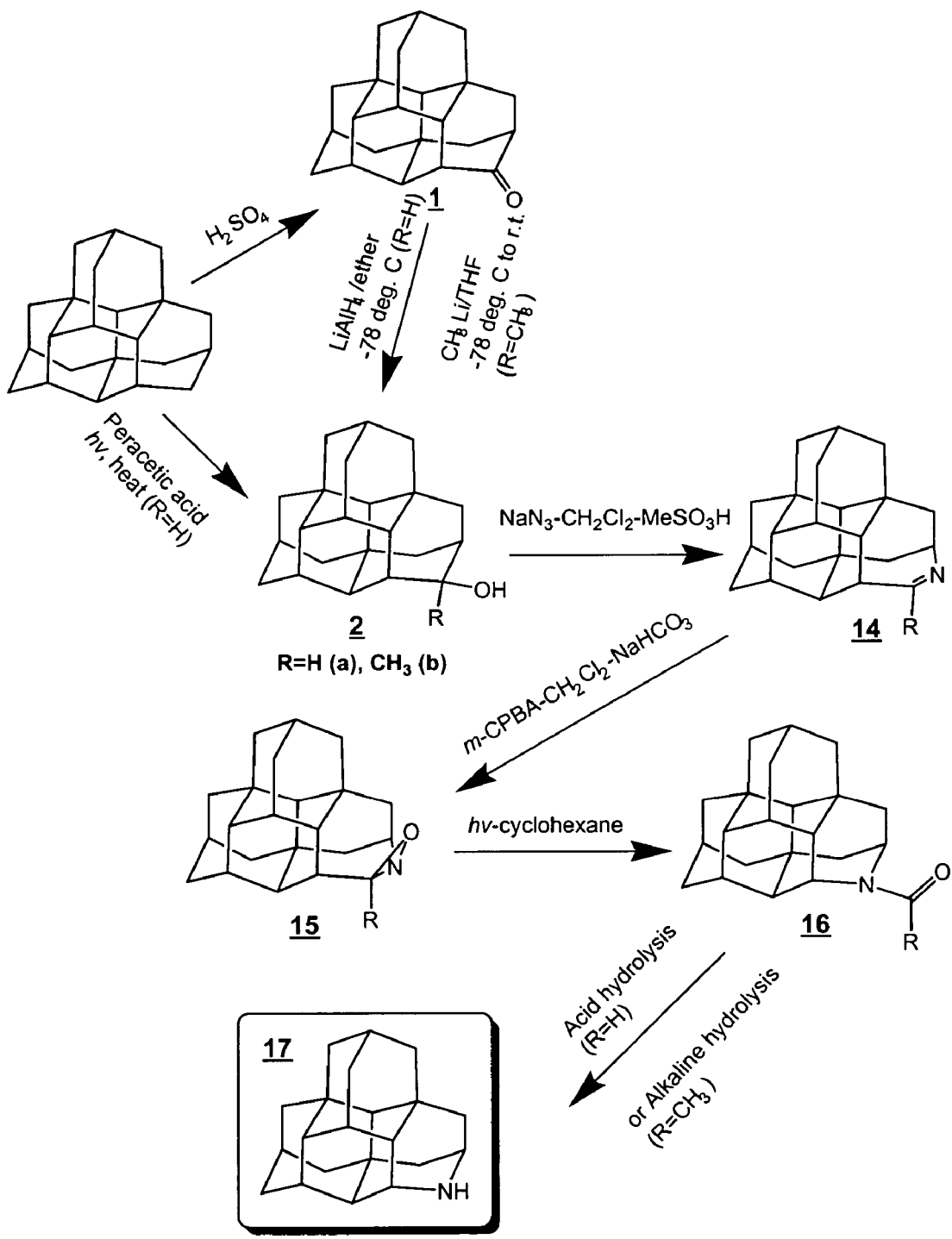
FIGS. 7–8 illustrate routes for introducing a nitrogen heteroatom into a diamondoid.
Figure 8:
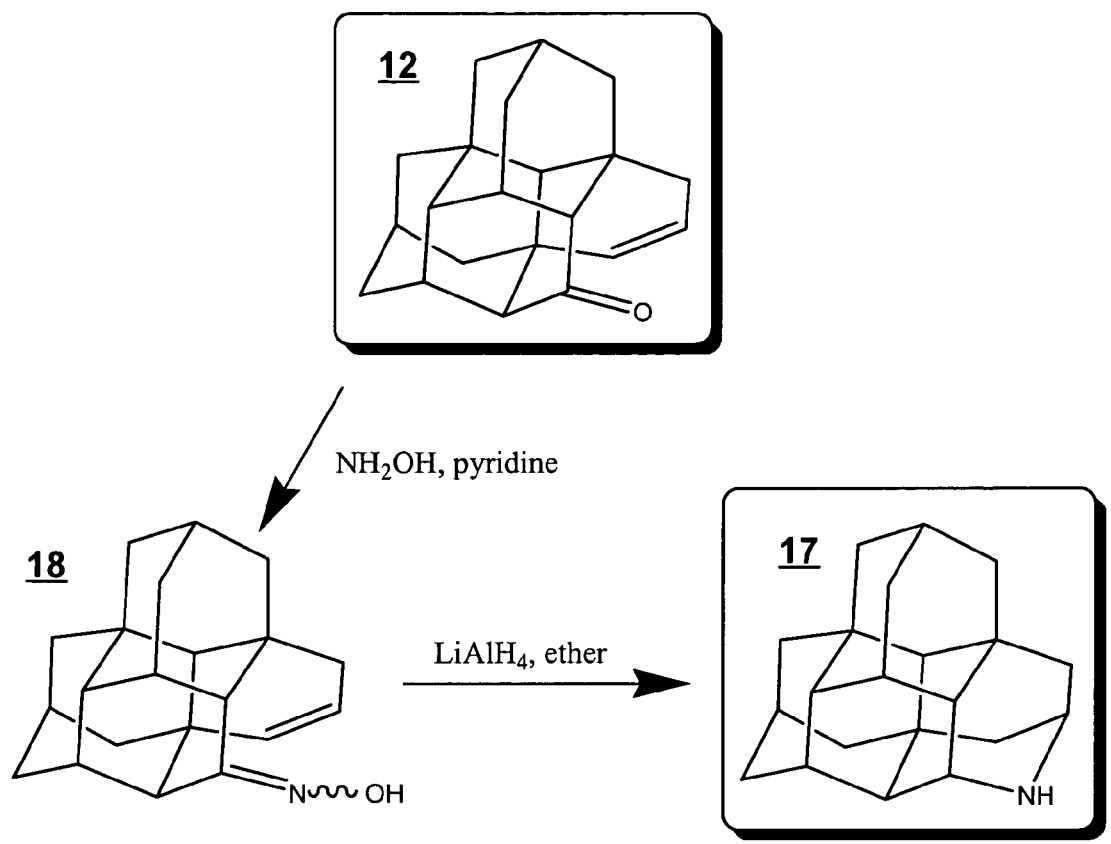
Figure 9:
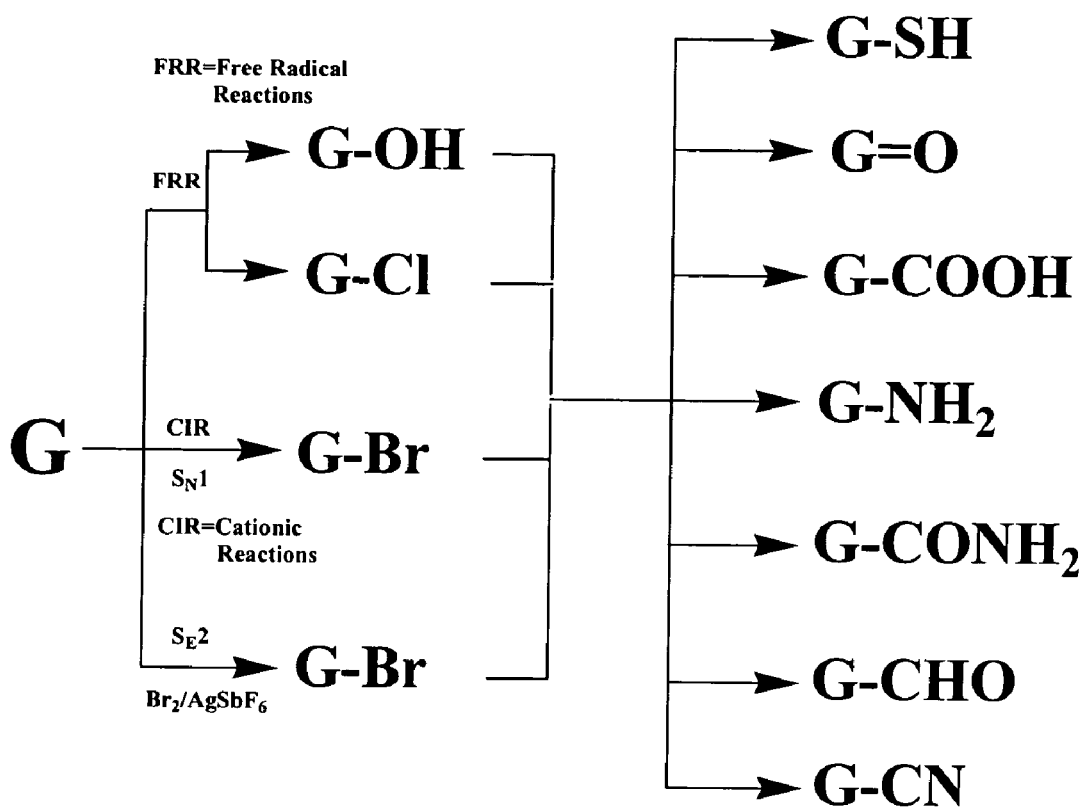
FIGS. 9–23 illustrate representative routes for functionalizing heterodiamondoids.
Figure 10:
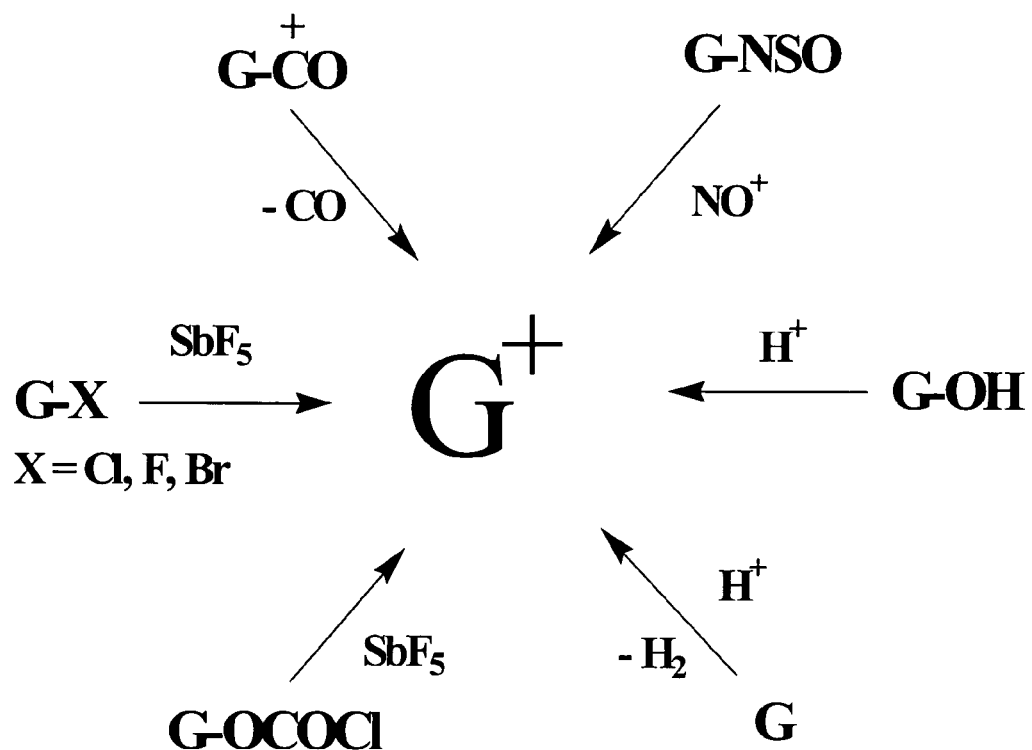
Figure 11:
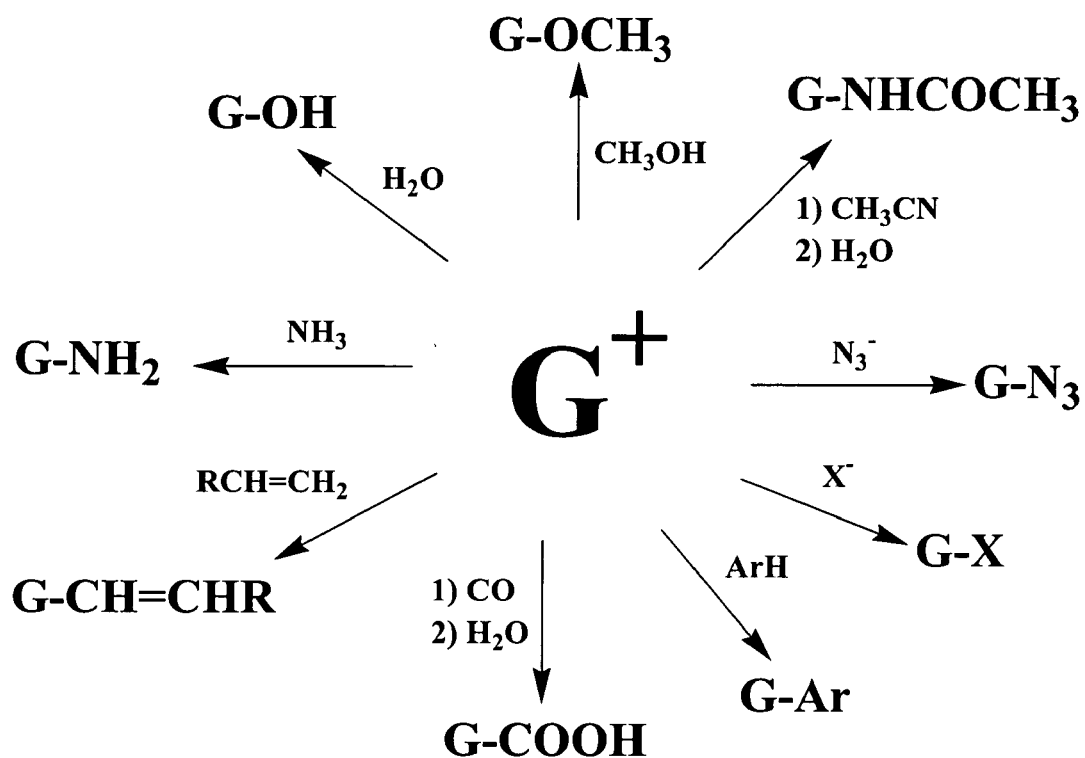
Figure 12:
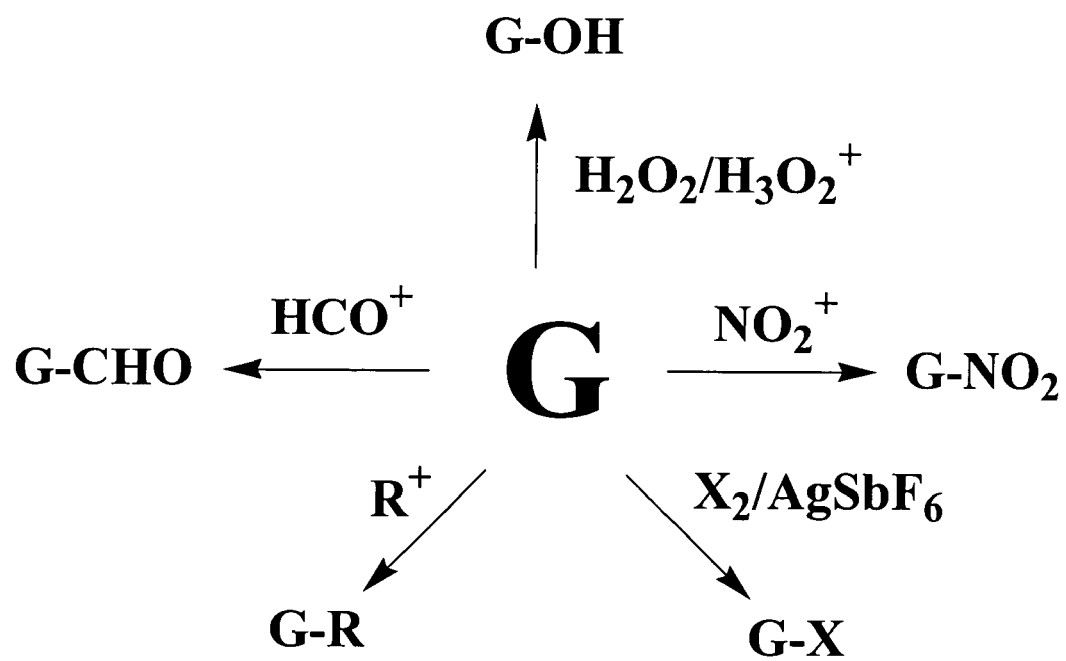

Starting from the diamondoids, there are several methodologies for the synthesis of heterodiamondoids such as oxa and thia diamondoids. For example, FIGS. 3–5 illustrate three different synthesis pathways to oxadiamondoids. FIG. 6 shows two different pathways to thiadiamondoids. For another example, FIGS. 7 and 8 show different ways to prepare azadiamondoids. It is understood that while in the FIGS. 3–8 only iso-tetramantane is shown as the starting diamondoid, triamantane and other higher diamondoids may also be used.

Nitrogen heterodiamondoids may be synthesized by the method of T. Sasaki et al., *Synthesis of adamantane derivatives. 39. Synthesis and acidolysis of 2-azidoadamantanes. A facile route to 4-azahomoadamant-4-enes*, Heterocycles Vol. 7, No. 1, p. 315 (1977). The procedure consists of a substitution of a hydroxyl group with an azide function via the formation of a carbocation, followed by acidolysis of the azide product.

Another synthetic pathway is provided by T. Sasaki et al., *Synthesis of Adamantane Derivatives. XI. The Schmidt Reaction of Adamantane-2-one*, J. Org. Chem. Vol. 35, No. 12, p. 4109 (1970).

Alternatively, a 1-hydroxy-2-azaadamantane may be synthesized from 1,3-dibromoadamantane, as reported by A. Gagneux et al. in *1-Substituted 2-heteroadamantanes*, Tetrahedron Letters No. 17, pp. 1365–1368 (1969). This is a multiple-step process, wherein first the di-bromo starting material is heated to a methyl ketone, which subsequently undergoes ozonization to a diketone. The diketone is heated with four equivalents of hydroxylamine to produce a 1:1 mixture of cis and trans-dioximes; this mixture is hydrogenated to the compound 1-amino-2-azaadamantane dihydrochloride. Finally, nitrous acid transforms the dihydrochloride to the hetero-adamantane 1-hydroxy-2-azadamantane.

Alternatively, a 2-azaadamantane compound may be synthesized from a bicyclo[3.3.1]nonane-3,7-dione, as reported by J. G. Henkel and W. C. Faith, in *Neighboring group effects in the β-halo amines. Synthesis and solvolytic reactivity of the anti-4-substituted 2-azaadamantyl system*, in J. Org. Chem. Vol. 46, No. 24, pp. 4953–4959 (1981). The dione may be converted by reductive amination (although the use of ammonium acetate and sodium cyanoborohydride produced better yields) to an intermediate, which may be converted to another intermediate using thionyl choloride. Dehalogenation of this second intermediate to 2-azaadamantane was accomplished in good yield using LiAlH$_4$ in DME.

A synthetic pathway that is related in principal to one useful in the present invention was reported by S. Eguchi et al. in *A novel route to the 2-aza-adamantyl system via photochemical ring contraction of epoxy 4-azahomoadamantanes*, J. Chem. Soc. Chem. Commun., p. 1147 (1984). In this approach, a 2-hydroxyadamantane is reacted with a NaN$_3$ based reagent system to form the azahomoadamantane, with is then oxidized by m-chloroperbenzoid acid (m-CPBA) to give an epoxy 4-azahomoadamantane. The epoxy is then irradiated in a photochemical ring contraction reaction to yield the N-acyl-2-aza-adamantane.

An exemplary reaction pathway for synthesizing a nitrogen-containing hetero iso-tetramantane is illustrated in FIG. 7. It will be known to those of ordinary skill in the art that the reaction conditions of the pathway depicted in FIG. 7 will be substantially different from those of Eguchi due to the differences in size, solubility, and reactivities of tetramantane in relation to adamantane. A second pathway available for synthesizing nitrogen-containing heterodiamondoids is illustrated in FIG. 8.

A phosphorus-containing heterodiamondoid may be synthesized by adapting the pathway outlined by J. J. Meeuwissen et. al in *Synthesis of 1-phosphaadamantane*, Tetrahedron Vol. 39, No. 24, pp. 4225–4228 (1983). It is contemplated that such a pathway may be able to synthesis heterodiamondoids that contain both nitrogen and phosphorus atoms substitutionally positioned in the diamondoid structure, with the advantages of having two different types of electron-donating heteroatoms in the same structure.

After preparing the heterodiamondoids, they may be functionalized with at least one functional group. Representative pathways are provided in the Examples. Additional disclosure of derivatization methods is provided below and in FIGS. 9–23.

Functionalization of Heterodiamondoids and the Derivatives Therefrom

Table 3 provides a representative list of heterodiamondoid derivatives.

TABLE 3

Representative Heterodiamondoid Derivatives

| HETERODIAMONDOID | FUNCTIONAL GROUP |
| --- | --- |
| hetero trimantane – hetero undecamantane | —F |
| hetero trimantane – hetero undecamantane | —Cl |
| hetero trimantane – hetero undecamantane | —Br |
| hetero trimantane – hetero undecamantane | —I |

TABLE 3-continued

Representative Heterodiamondoid Derivatives

| HETERODIAMONDOID | FUNCTIONAL GROUP |
|---|---|
| hetero trimantane – hetero undecamantane | —OH |
| hetero trimantane – hetero undecamantane | —CO$_2$H |
| hetero trimantane – hetero undecamantane | —CO$_2$CH$_2$CH$_3$ |
| hetero trimantane – hetero undecamantane | —COCl |
| hetero trimantane – hetero undecamantane | —SH |
| hetero trimantane – hetero undecamantane | —CHO |
| hetero trimantane – hetero undecamantane | —CH$_2$OH |
| hetero trimantane – hetero undecamantane | —NH$_2$ |
| hetero trimantane – hetero undecamantane | —NO$_2$ |
| hetero trimantane – hetero undecamantane | =O (keto) |
| hetero trimantane – hetero undecamantane | —CH=CH$_2$ |
| hetero trimantane – hetero undecamantane | —C≡CH |
| hetero trimantane – hetero undecamantane | —C$_6$H$_5$ |
| hetero trimantane – hetero undecamantane | —NHCOCH$_3$ |
| hetero trimantane – hetero undecamantane | —NHCHO |
| hetero trimantane – hetero undecamantane | —CH$_2$Br |
| hetero trimantane – hetero undecamantane | —CH=CHBr |
| hetero trimantane – hetero undecamantane | —C≡CBr |
| hetero trimantane – hetero undecamantane | —C$_6$H$_4$Br |
| hetero trimantane – hetero undecamantane | —CH$_2$Cl |
| hetero trimantane – hetero undecamantane | —CH=CHCl |
| hetero trimantane – hetero undecamantane | —C≡CCl |
| hetero trimantane – hetero undecamantane | —C$_6$H$_4$Cl |
| hetero trimantane – hetero undecamantane | —CH$_2$OH |
| hetero trimantane – hetero undecamantane | —C$_6$H$_4$OH |
| hetero trimantane – hetero undecamantane | —OCOCl |
| hetero trimantane – hetero undecamantane | —OCSCl |
| hetero trimantane – hetero undecamantane | —OCH$_3$ |
| hetero trimantane – hetero undecamantane | —OCH$_2$CH$_2$NH$_2$ |
| hetero trimantane – hetero undecamantane | —OCH$_2$C(CH$_3$)$_2$N(CH$_3$)$_2$ |
| hetero trimantane – hetero undecamantane | —O(CH$_2$)$_5$NH$_2$ |
| hetero trimantane – hetero undecamantane | —O(CH$_2$)$_5$NH$_2$HCl |
| hetero trimantane – hetero undecamantane | —OCH$_2$CH$_2$—N(pyrrolidinyl) |
| hetero trimantane – hetero undecamantane | —OCH$_2$CH$_2$—N(morpholinyl) |
| hetero trimantane – hetero undecamantane | —OCH$_2$CH$_2$NHC(O)CH$_3$ |
| hetero trimantane – hetero undecamantane | —C≡N |
| hetero trimantane – hetero undecamantane | —CH$_2$CO$_2$H |
| hetero trimantane – hetero undecamantane | —CH$_2$CO$_2$CH$_3$ |
| hetero trimantane – hetero undecamantane | —CF$_3$CO$_2$H |
| hetero trimantane – hetero undecamantane | —COCH$_3$ |
| hetero trimantane – hetero undecamantane | —N=C=S |
| hetero trimantane – hetero undecamantane | —N=C=O |
| hetero trimantane – hetero undecamantane | —N=S=O |
| hetero trimantane – hetero undecamantane | —PH$_2$ |
| hetero trimantane – hetero undecamantane | —POCl$_2$ |
| hetero trimantane – hetero undecamantane | —PO(OH)$_2$ |
| hetero trimantane – hetero undecamantane | —SO$_2$H |
| hetero trimantane – hetero undecamantane | —OSO$_3$H |
| hetero trimantane – hetero undecamantane | —SO$_2$CH$_3$ |
| hetero trimantane – hetero undecamantane | —SOCl |
| hetero trimantane – hetero undecamantane | —SO$_2$OCH$_3$ |
| hetero trimantane – hetero undecamantane | —SON(CH$_3$)$_2$ |
| hetero trimantane – hetero undecamantane | —N$_3$ |
| hetero trimantane – hetero undecamantane | (oxazolidinone ring) |

TABLE 3-continued

Representative Heterodiamondoid Derivatives

| HETERODIAMONDOID | FUNCTIONAL GROUP |
|---|---|
| hetero trimantane – hetero undecamantane | [N(H)-C(=S)-O ring structure] |
| hetero trimantane – hetero undecamantane | [N(CH₃)-C(=O)-O ring structure] |
| hetero trimantane – hetero undecamantane | [N(CH₃)-C(=S)-O ring structure] |

Heterodiamondoid-Containing Polymers

Polymerization of polymerizable heterodiamondoid derivatives to form heterodiamondoid-containing polymers is similar to what we have already disclosed in U.S. patent application Ser. No. 10/046,486 filed on Jan. 16, 2002 entitled "polymerizable higher diamondoid derivatives", which is hereby incorporated herein by reference. FIGS. 24–33 present some exemplary heterodiamondoid-containing polymers and the polymerization reactions which provide them.

EXAMPLES

Example 1 describes a most universal route for isolating higher diamondoids components which can be applied to all feedstocks used herein. This process uses HPLC as its final isolation step.

Example 2 describes methods that could be used to prepare a oxadiamondoid from a diamondoid-containing feedstock.

Example 3 describes methods that could be used to prepare a azadiamondoid from a diamondoid-containing feedstock.

Examples 4–10 describe methods that could be used to prepare heterodiamondoids (e.g. oxa-, thia-, aza-diamondoids, etc.) from diamondoids.

Examples 11–46 describe methods that could be used to prepare heterodiamondoid derivatives.

Examples 47–64 describe methods that could be used to prepare heterodiamondoid-containing polymers.

Example 1

This Example has seven steps.
Step 1. Feedstock selection
Step 2. GCMC assay development
Step 3. Feedstock atmospheric distillation
Step 4. Vacuum fractionation of atmospheric distillation residue
Step 5. Pyrolysis of isolated fractions
Step 6. Removal of aromatic and polar nondiamondoid components
Step 7. Multi-column HPLC isolation of higher diamondoids
  a) First column of first selectivity to provide fractions enriched in specific higher diamondoids.
  b) Second column of different selectivity to provide isolated higher diamondoids.

This example is written in terms of isolating several hexamantanes but the other higher diamondoids can be isolated using it, as well.

Step 1—Feedstock Selection

Suitable starting materials were obtained. These materials included a gas condensate, Feedstock A, and a gas condensate containing petroleum components, Feedstock B. Although other condensates, petroleums, or refinery cuts and products could have been used, these two materials were chosen due to their high diamondoid concentration, approximately 0.3 weight percent higher diamondoids, as determined by GC and GC/MS. Both feedstocks were light colored and had API gravities between 19 and 20° API.

Step 2—GC/MS Assay Development

Feedstock A was analyzed using gas chromatography/mass spectrometry to confirm the presence of target higher diamondoids and to provide gas chromatographic retention times for these target materials. This information is used to track individual higher diamondoids through subsequent isolation procedures.

Step 3—Feedstock Atmospheric Distillation

A sample of Feedstock B was distilled into a number of fractions based on boiling points to separate the lower boiling point components (nondiamondoids and lower diamondoids) and for further concentration and enrichment of particular higher diamondoids in various fractions.

Step 4—Fractionation of Atmospheric Distillation Residue by Vacuum Distillation

The Feedstock B atmospheric residium from Step 3 (comprising 2–4 weight percent of the original feedstock) was distilled into fractions containing higher diamondoids.

Step 5—Pyrolysis of Isolated Fractions

A high-temperature reactor was used to pyrolyze and degrade a portion of the nondiamondoid components in various distillation fractions obtained in Step 4 thereby enriching the diamondoids in the residue. The pyrolysis process was conducted at 450° C. for 19.5 hours.

Step 6—Removal of Aromatic and Polar Nondiamondoid Components

The pyrolysate produced in Step 5 was passed through a silica-gel gravity chromatography column (using cyclohexane elution solvent) to remove polar compounds and asphaltenes.

Step 7—Multi-column HPLC Isolation of Higher Diamondoids

An excellent method for isolating high-purity higher diamondoids uses two or more HPLC columns of different selectivities in succession.

The first HPLC system consisted of two Whatman M20 10/50 ODS columns operated in series using acetone as mobile phase at 5.00 mL/min. A series of HPLC fractions were taken.

Further purification of this HPLC fraction was achieved using a Hypercarb stationary phase HPLC column having a different selectivity in the separation of various hexamantanes than the ODS column discussed above.

Example 2

Oxatetramantanes from a Feedstock Containing Tetramantanes (FIG. 3)

A fraction as described in Example 1 containing all of the tetramantanes including some alkyltetramantanes and hydrocarbon impurities was obtained.

A solution of 200 mg of the above feedstock containing tetramantanes in 6.1 g of methylene chloride was mixed with 4.22 g of a solution of 1.03 g (13.5 mmol) of peracetic acid in ethyl acetate. While being stirred vigorously, the solution was irradiated with a 100-watt high intensity UV light. Gas evolution was evident from the start. The temperature was maintained at 40–45° C. for an about 21-hour irradiation period. Then the solution was concentrated to near dryness, treated twice in succession with 10-mL portions of toluene and reevaporated to dryness followed by $CH_2Cl_2$ extraction (15 mL×2). The combined organic extract was then dried over $Na_2SO_4$. Solvent was evaporated to almost dryness to yield a product which was subjected to GC/MS characterization showing the presence of a mixture hydroxylated tetramantanes as shown in FIG. 3. The chromatograms and mass spectra illustrating the presence of hydroxylated tetramantanes are provided as FIGS. 35–38.

Figure 39:
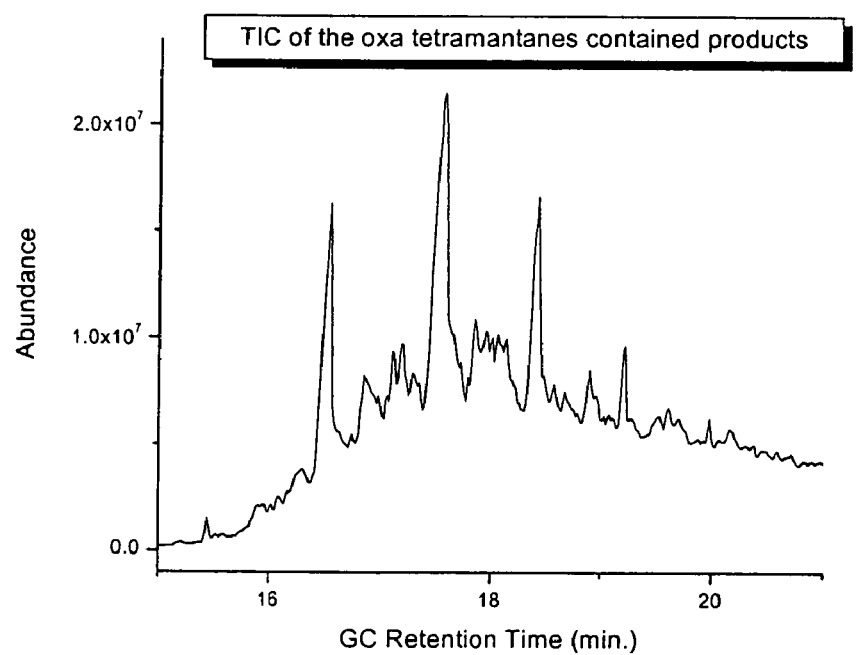
FIG. 39 shows the total ion chromatogram (TIC) of the oxa tetramantane-containing reaction mixture also produced in Example 2.
Figure 40:
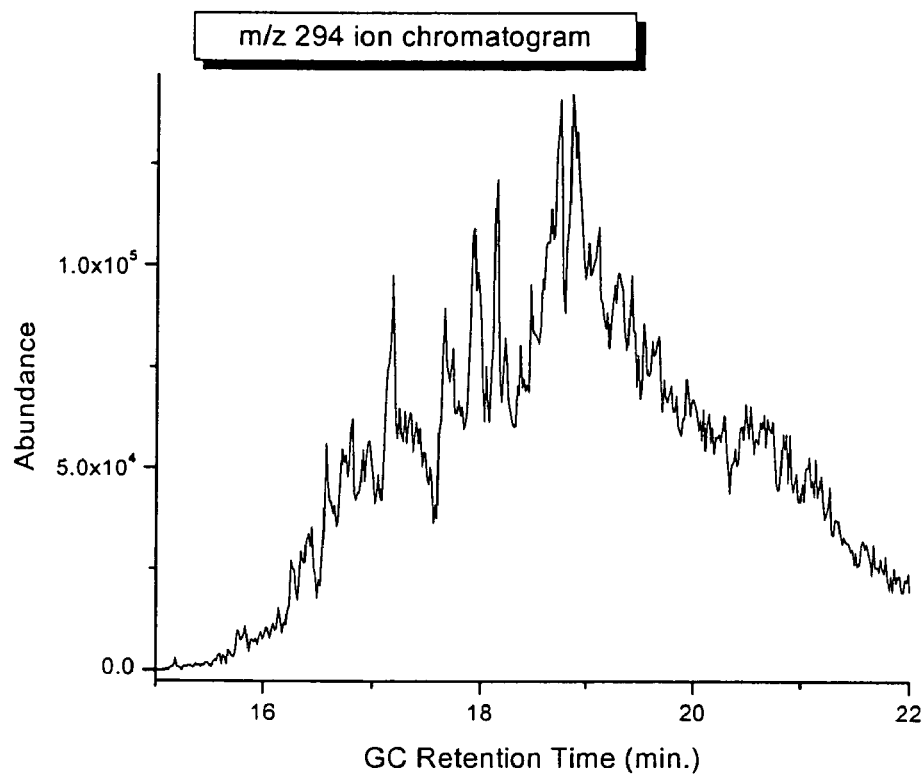
FIG. 40 is the m/z 294 ion chromatogram showing the presence of oxa tetramantanes in the TIC of the reaction product of Example 2.
Figure 41:
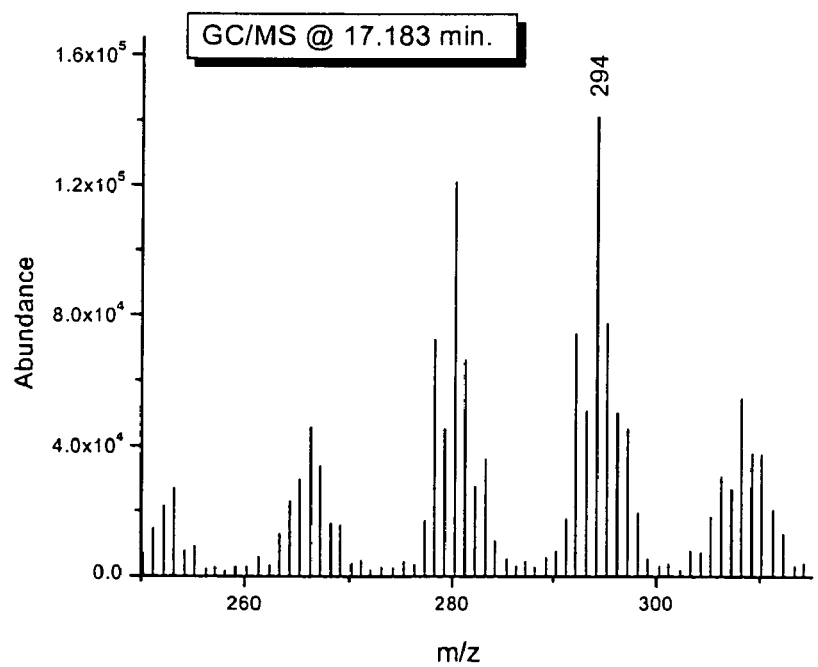
FIG. 41 is the mass spectrum of an oxa tetramantane with GC/MS retention time of 17.183 minutes from FIG. 40.
Figure 42:
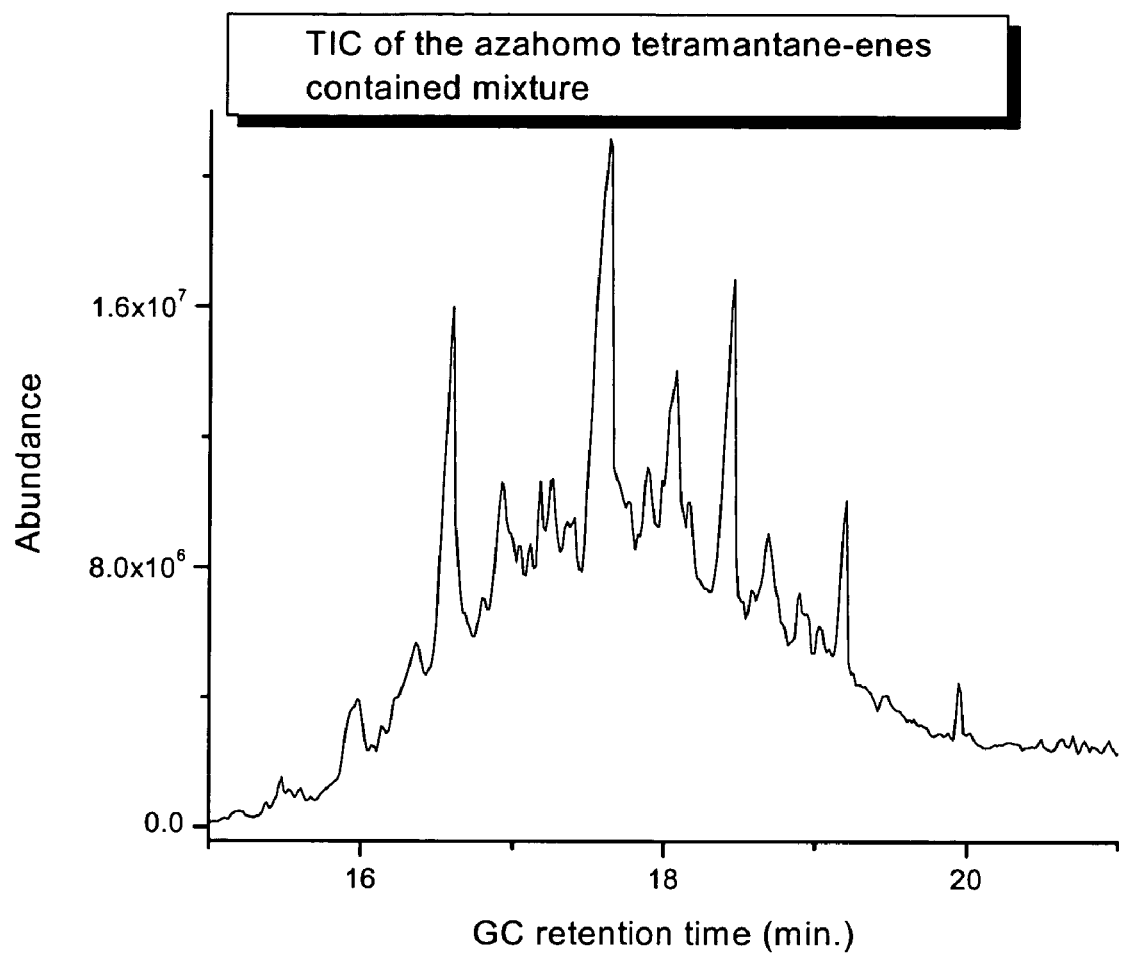
FIG. 42 shows the total ion chromatogram (TIC) of the azahomo tetramantane-ene-containing reaction mixture of Example 3.
Figure 43:
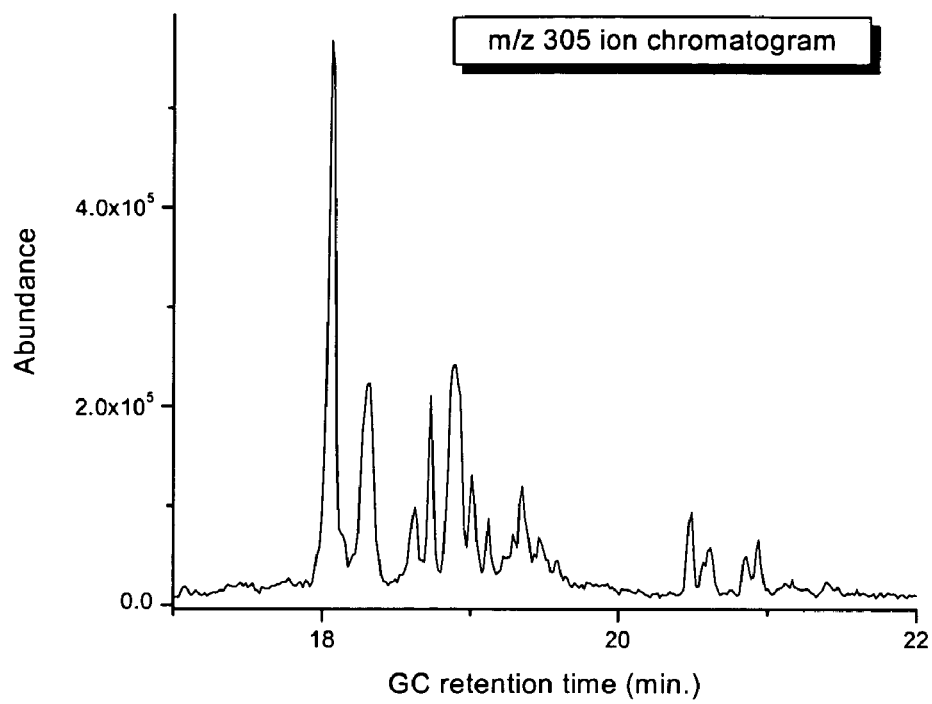
FIG. 43 is the m/z 305 ion chromatogram showing the presence of azahomo tetramantane-enes in the TIC of the reaction mixture of Example 3.
Figure 44:
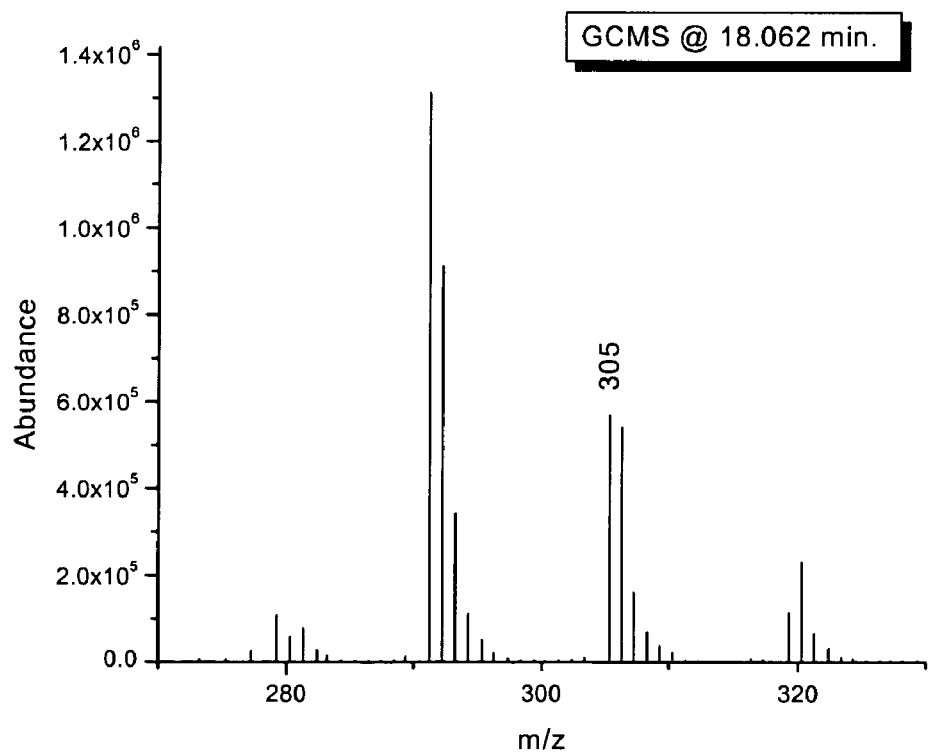
FIG. 44 is the mass spectrum of an azahomo tetramantane-ene with GC/MS retention time of 18.062 minutes from FIG. 43.
Figure 45:
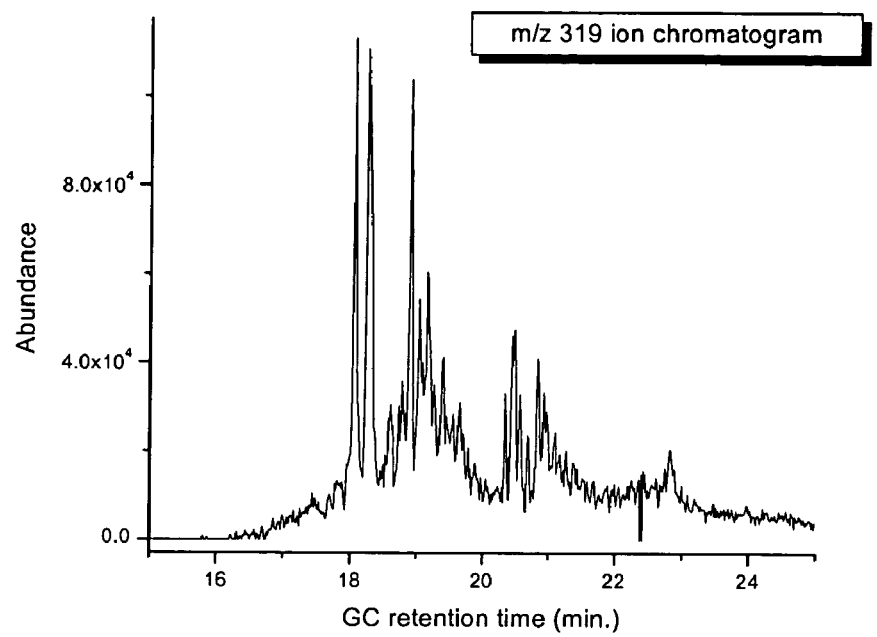
FIG. 45 is the m/z 319 ion chromatogram showing the presence of azahomo methyltetramantane-enes in the TIC of the reaction product.
Figure 46:
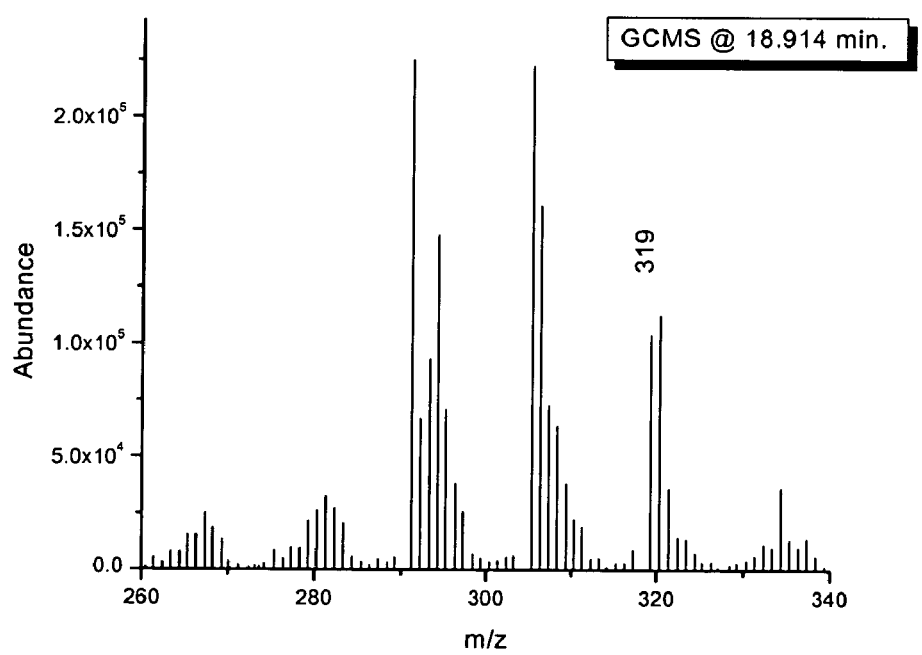
FIG. 46 is the mass spectrum of an azahomo methyltetramantane-ene with GC/MS retention time of 18.914 minutes from FIG. 45.
Figure 47:
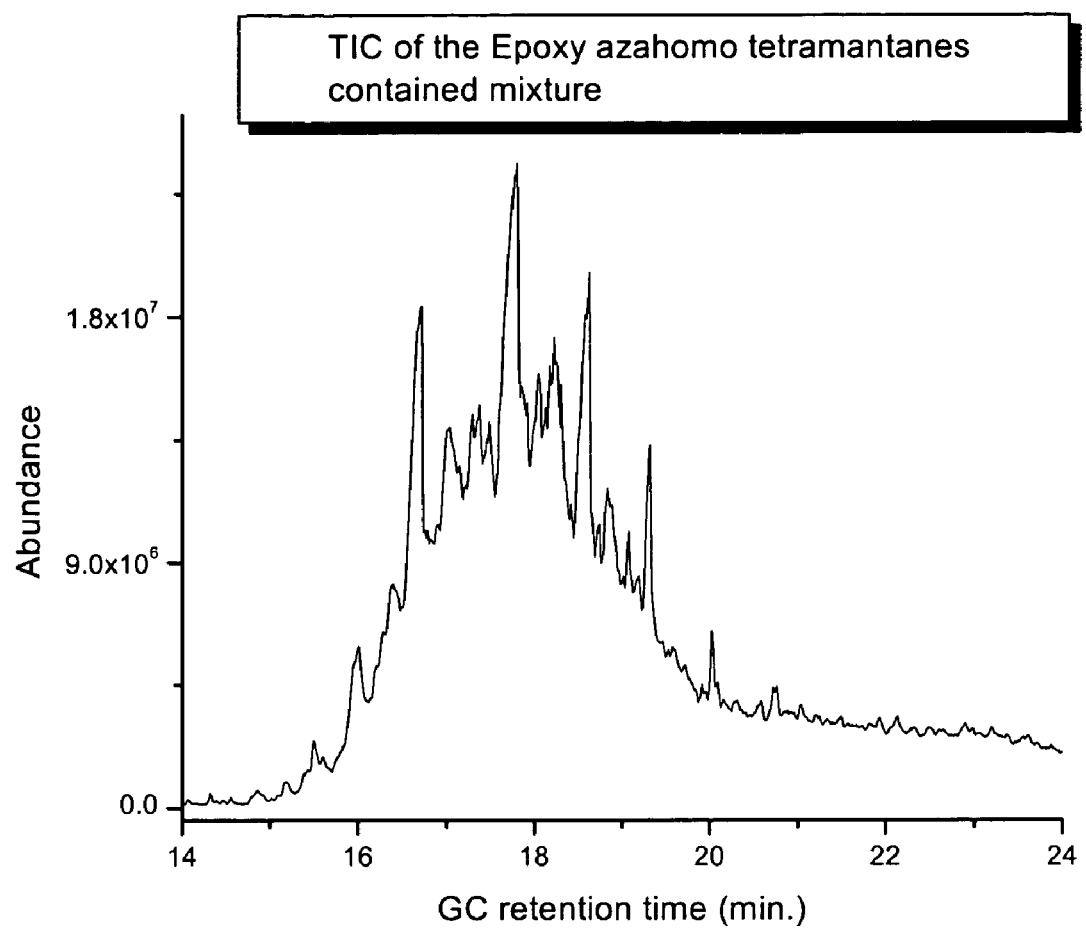
FIG. 47 shows the total ion chromatogram (TIC) of the epoxy azahomo tetramantane-containing reaction mixture produced in Example 3.
Figure 48:
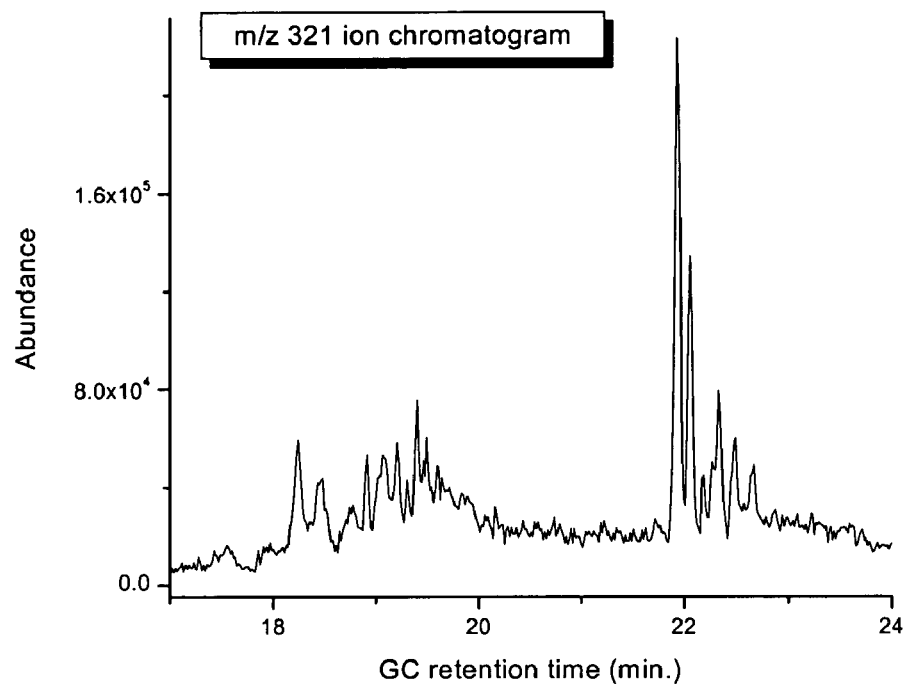
FIG. 48 is the m/z 321 ion chromatogram showing the presence of epoxy azahomo tetramantanes in the TIC of the reaction product of Example 3.
Figure 49:
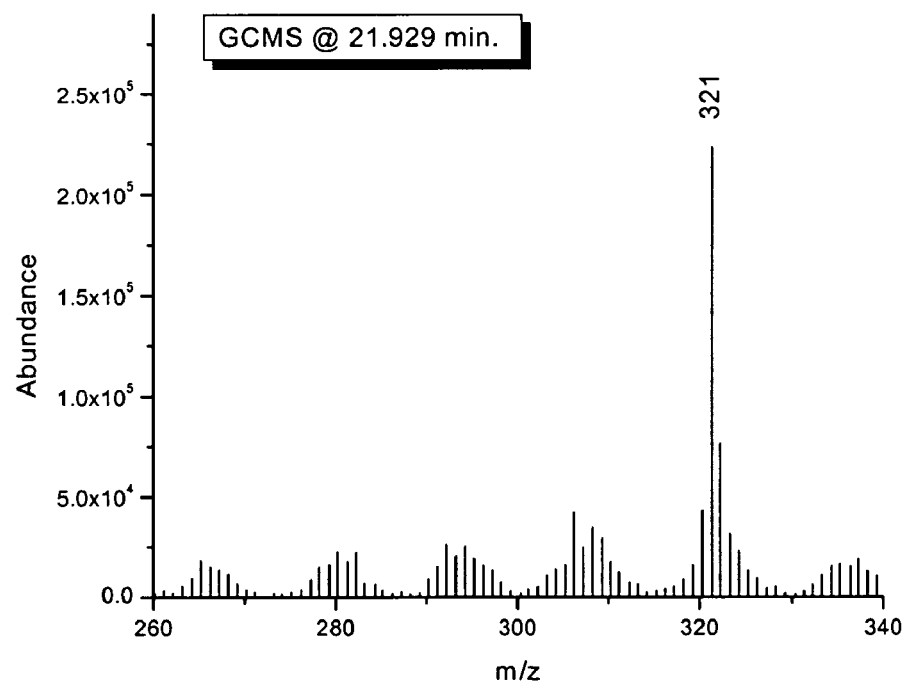
FIG. 49 is the mass spectra of an epoxy azahomo tetramantane with GC/MS retention times of 21.929 from FIG. 48.
Figure 50:
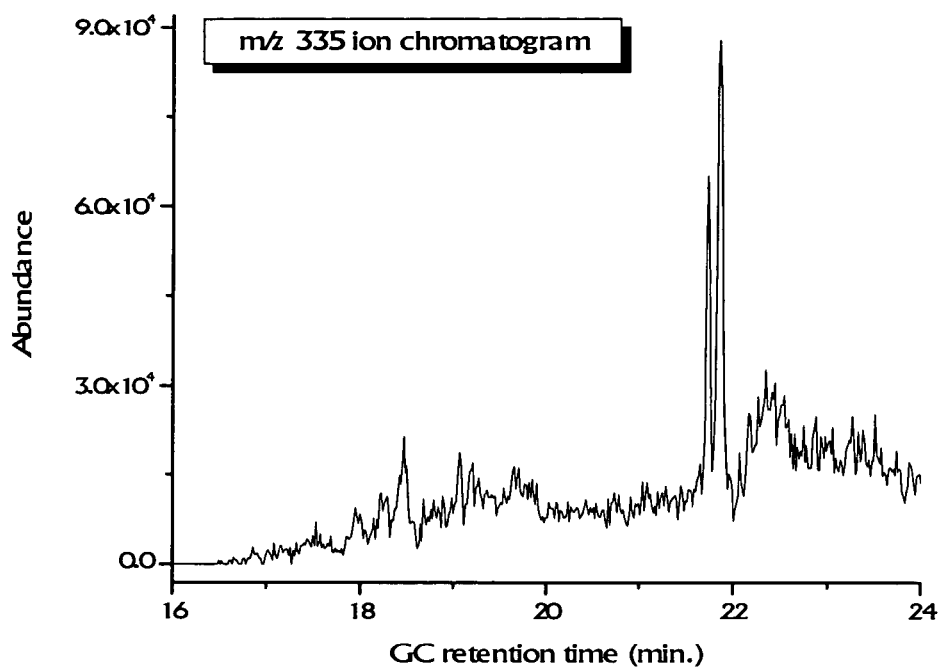
FIG. 50 is the m/z 335 ion chromatogram showing the presence of epoxy azahomo methyltetramantanes in the TIC of a reaction product of Example 3.
Figure 51:
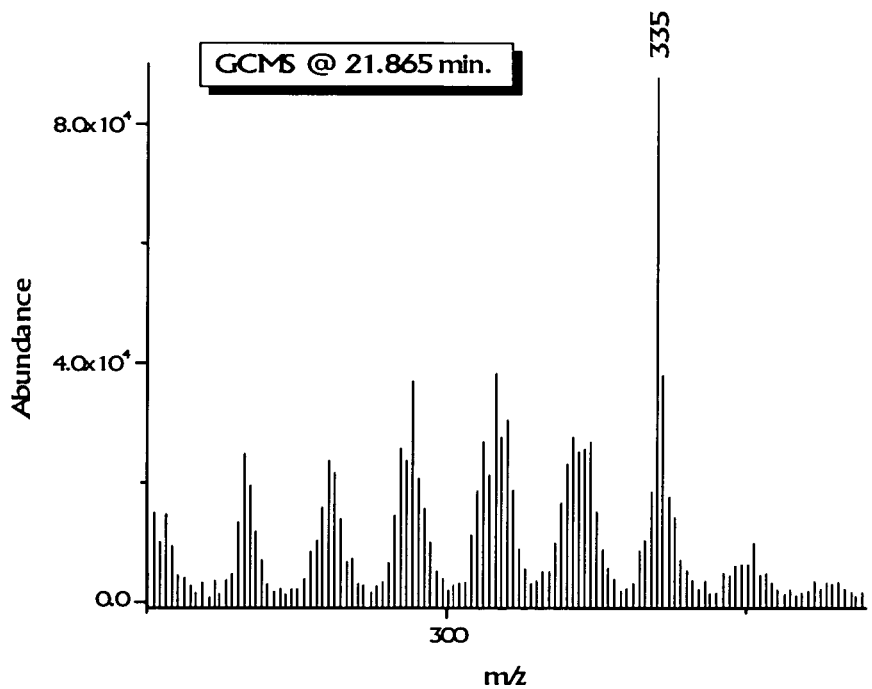
FIG. 51 is the mass spectrum of an epoxy azahomo methyltetramantane with GC/MS retention time of 21.865 minutes from FIG. 50.
Figure 52:
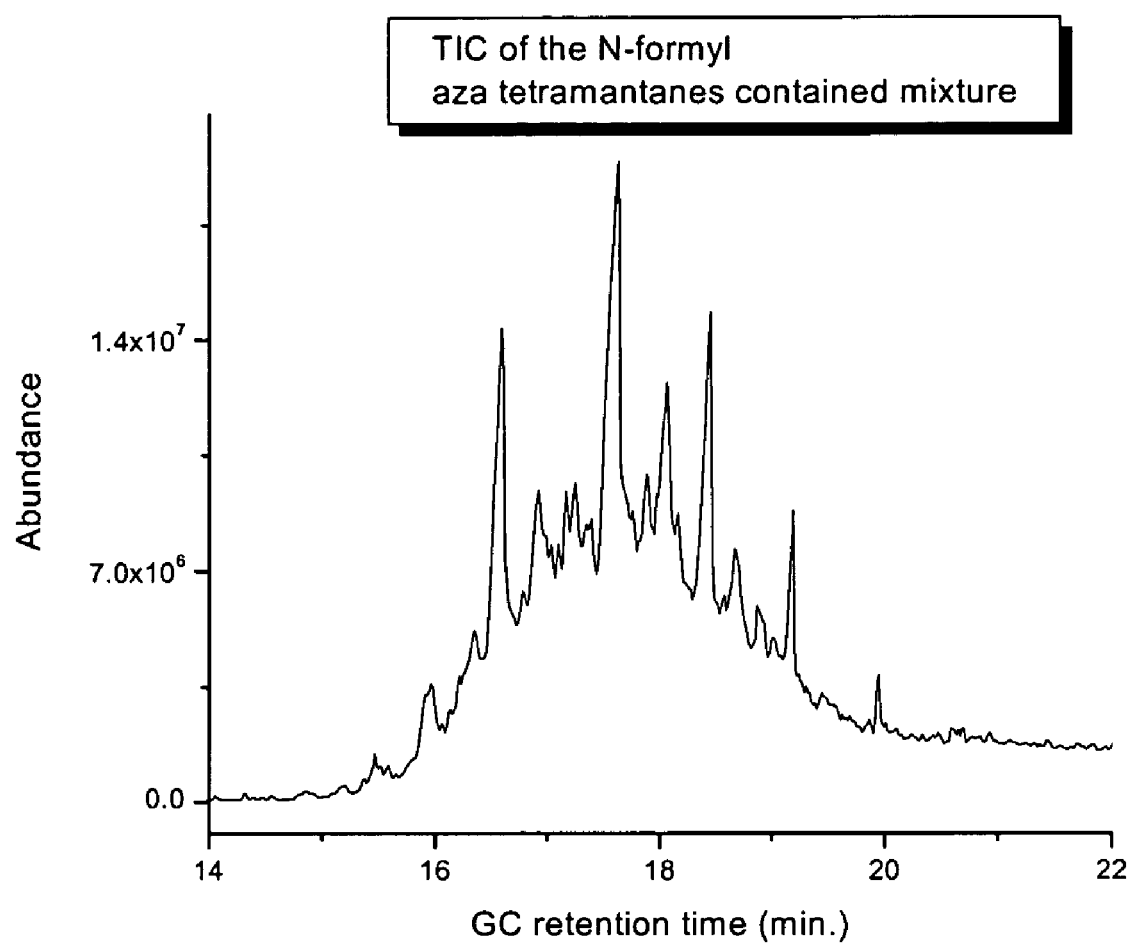
FIG. 52 shows the total ion chromatogram (TIC) of the N-formyl aza tetramantane-containing reaction mixture of Example 3.
Figure 53:
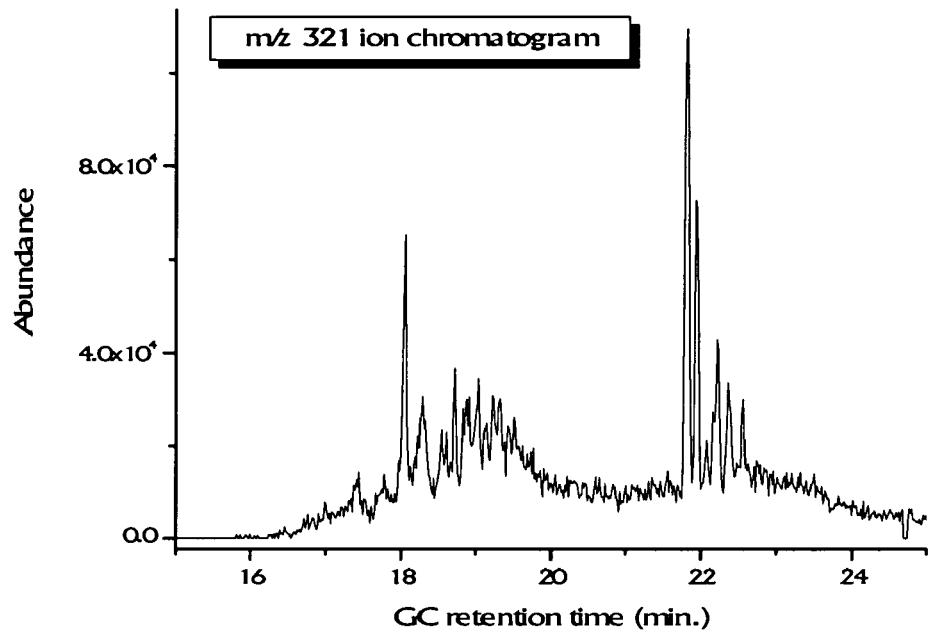
FIG. 53 is the m/z 321 ion chromatogram showing the presence of N-formyl aza tetramantanes in the TIC of the reaction product of Example 3.
Figure 54:
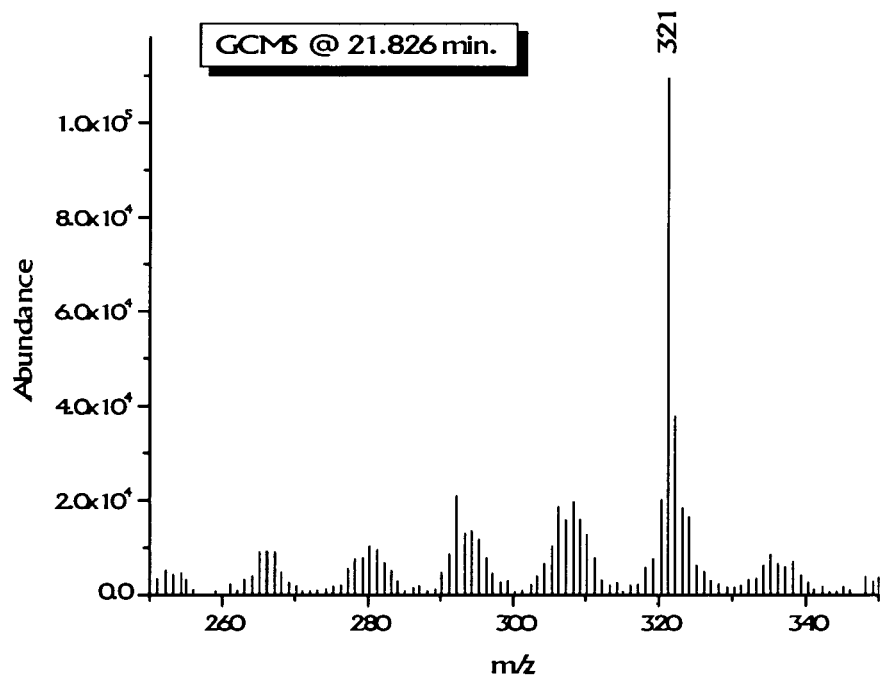
FIG. 54 is the mass spectrum of a N-formyl aza tetramantanes with GC/MS retention time of 21.826 minutes from FIG. 53.
Figure 55:
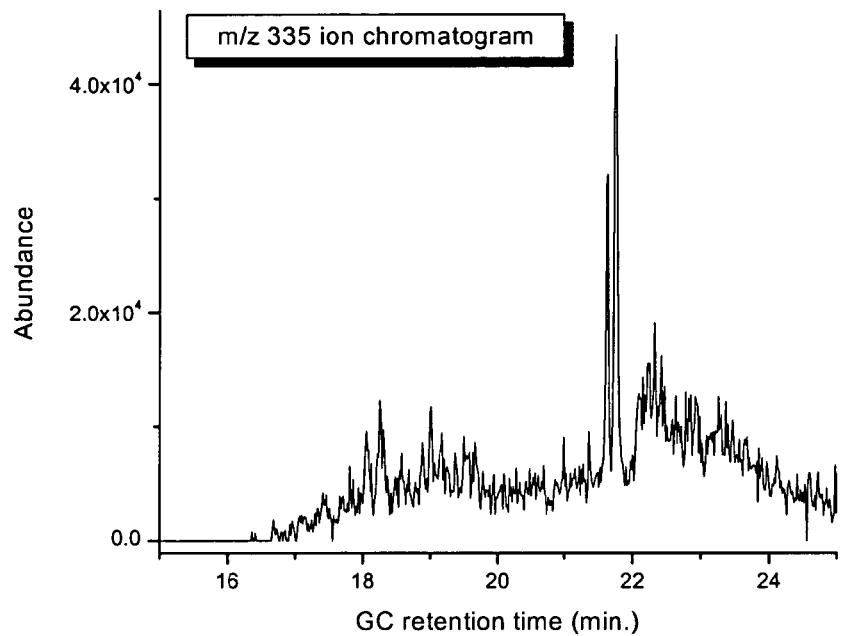
FIG. 55 is the m/z 335 ion chromatogram showing the presence of the N-formyl aza methyltetramantanes in the TIC of a reaction product of Example 3.
Figure 56:
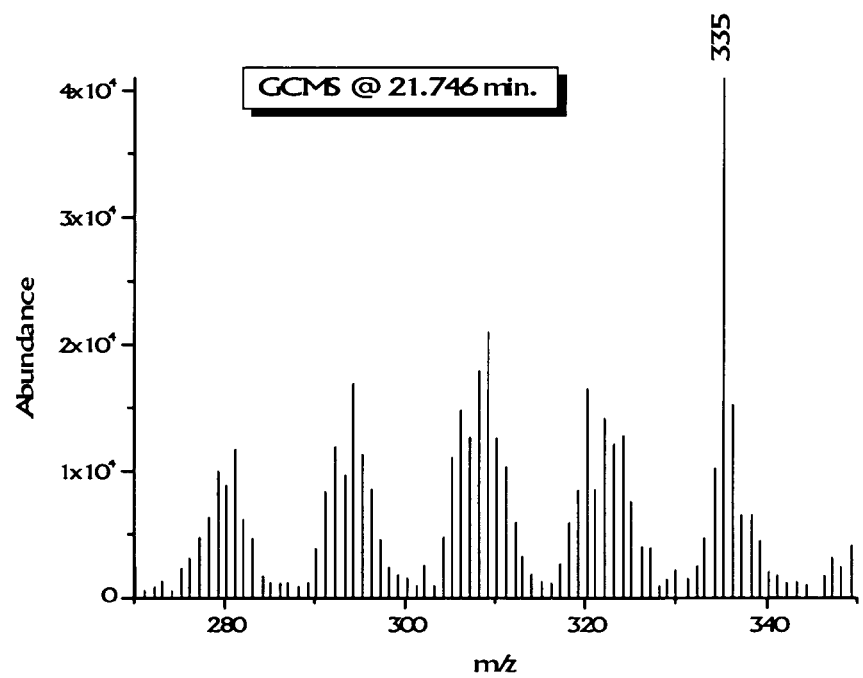
FIG. 56 is the mass spectrum of a N-formyl aza methyltetramantane with GC/MS retention time of 21.746 minutes from FIG. 55.
Figure 57:
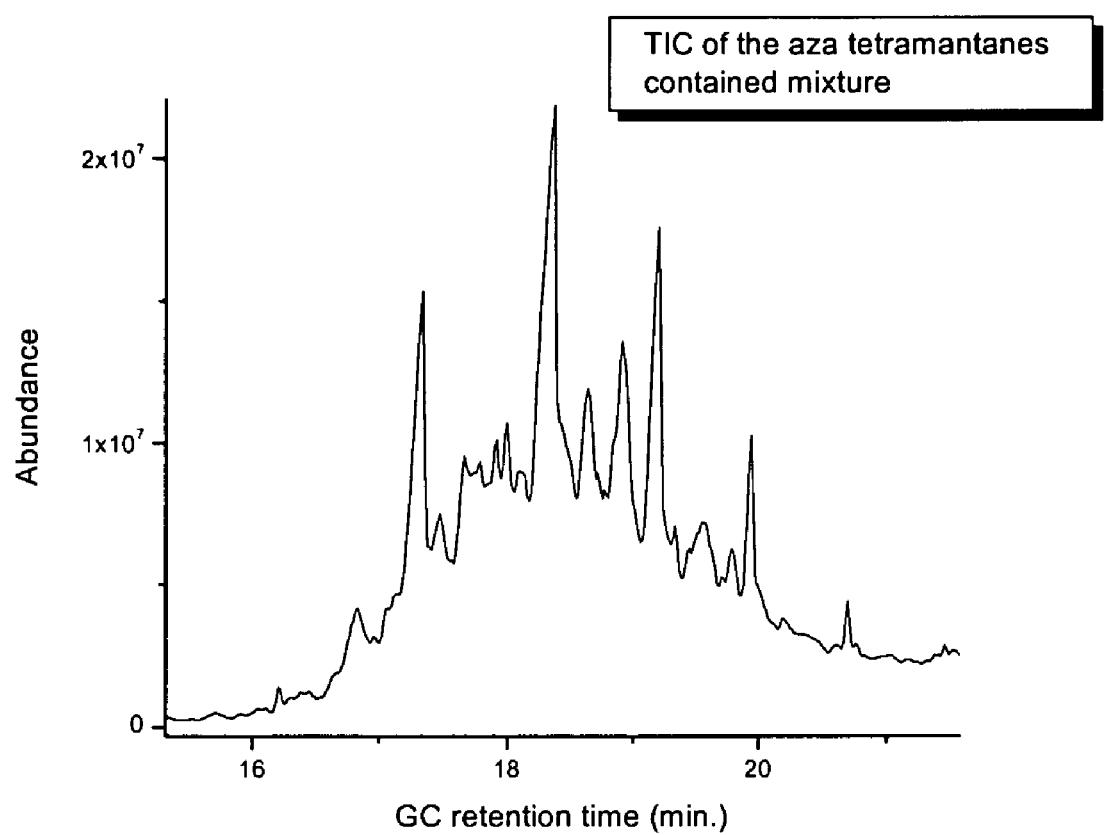
FIG. 57 shows the total ion chromatogram (TIC) of the aza tetramantane-containing reaction mixture produced in Example 3.
Figure 58:
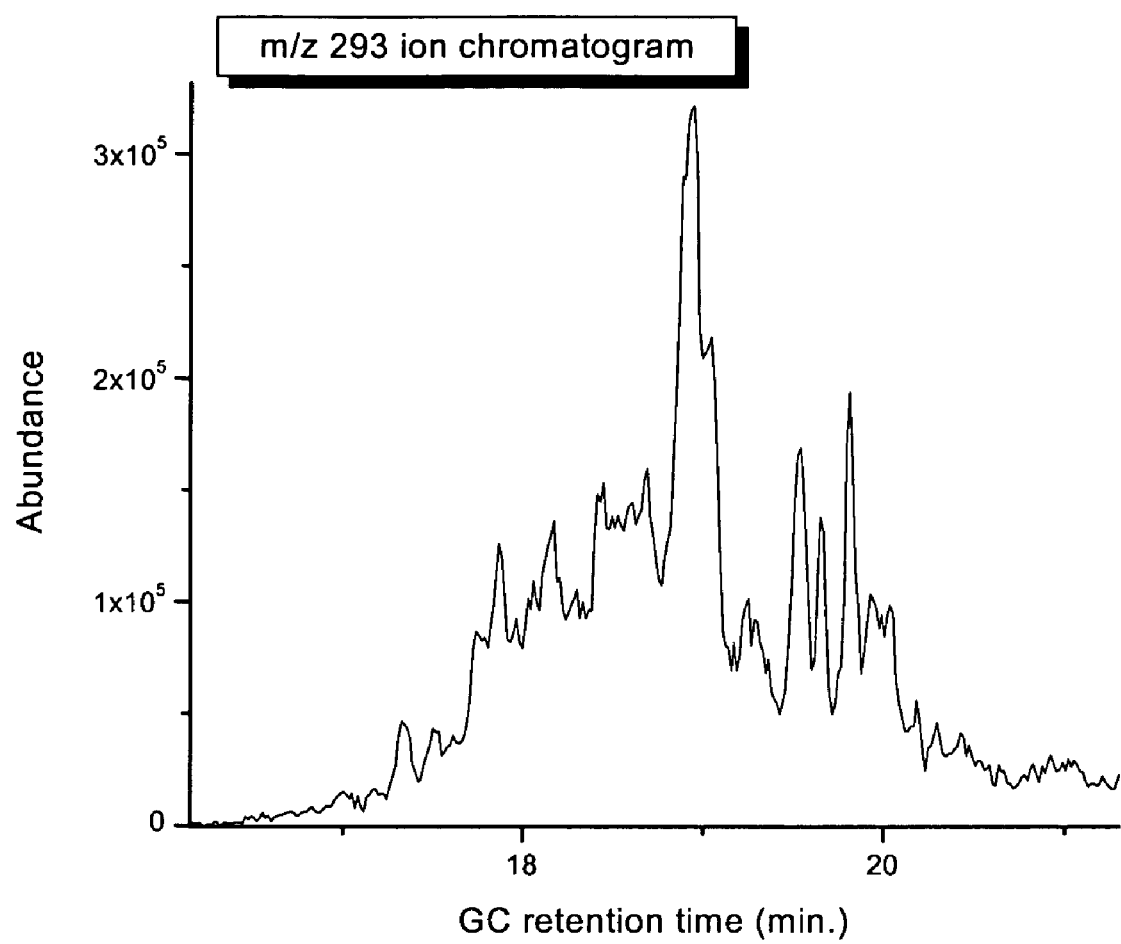
FIG. 58 is the m/z 293 ion chromatogram showing the presence of the aza tetramantanes in the TIC of the reaction product shown in Example 3.
Figure 59:
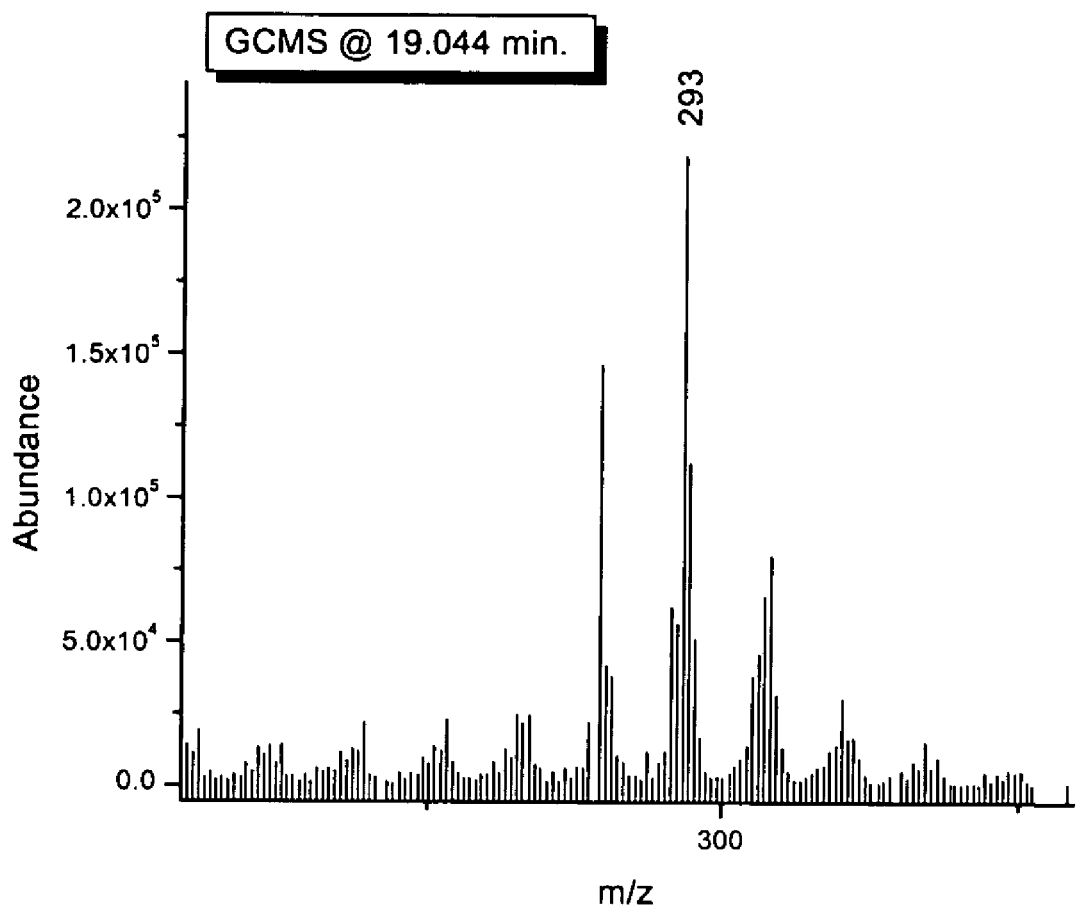
FIG. 59 is the mass spectrum of an aza tetramantane with GC/MS retention time of 19.044 minutes.
Figure 60:
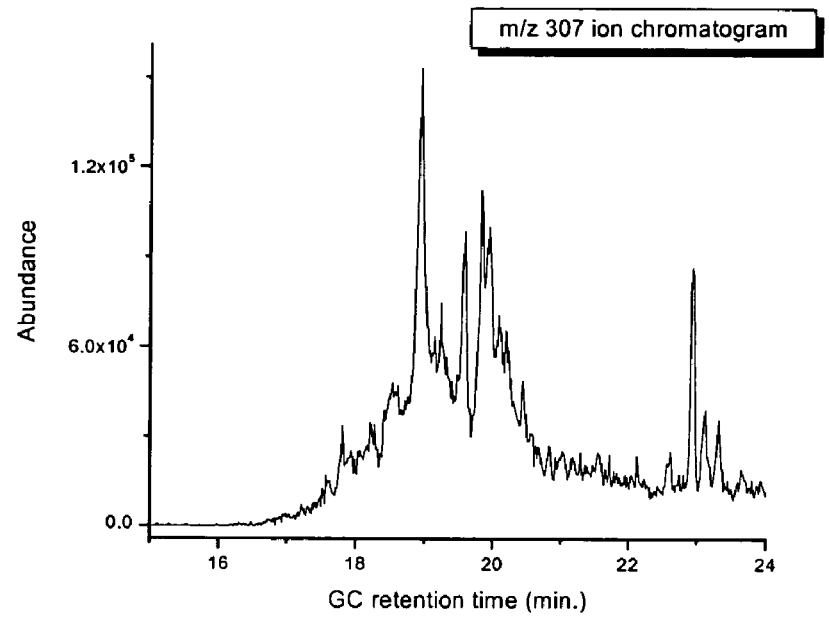
FIG. 60 is the m/z 307 ion chromatogram showing the presence of the aza methyltetramantanes in the TIC of a reaction product of Example 3.
Figure 61:
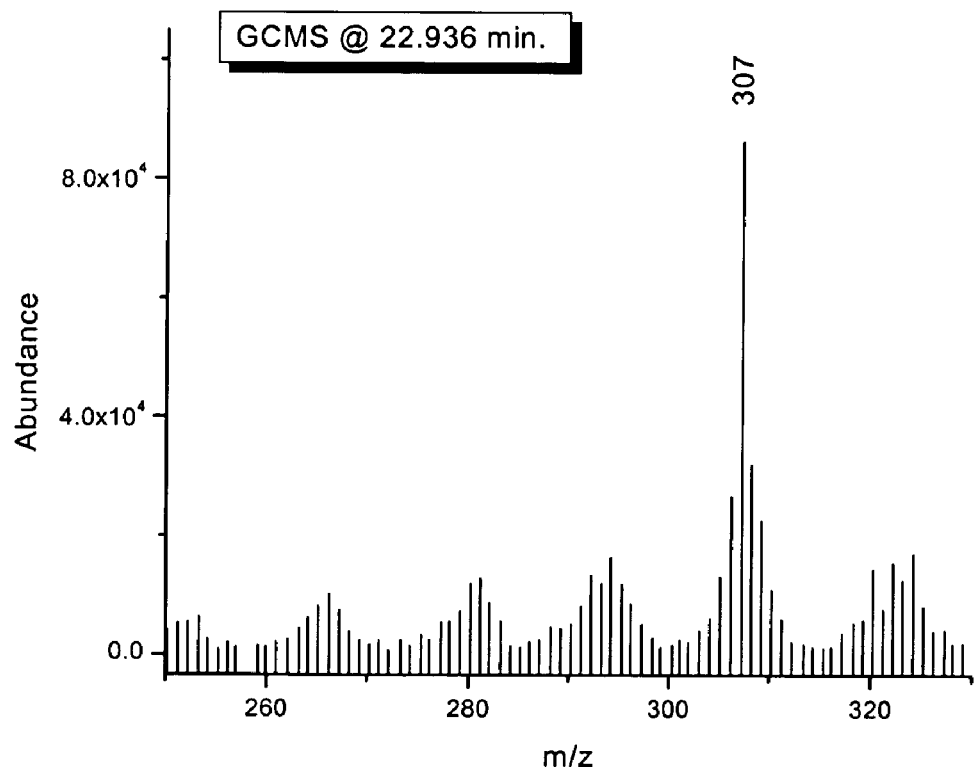
FIG. 61 is the mass spectrum of an aza methyltetramantane with GC/MS retention time of 22.936 minutes.
Figure 62:
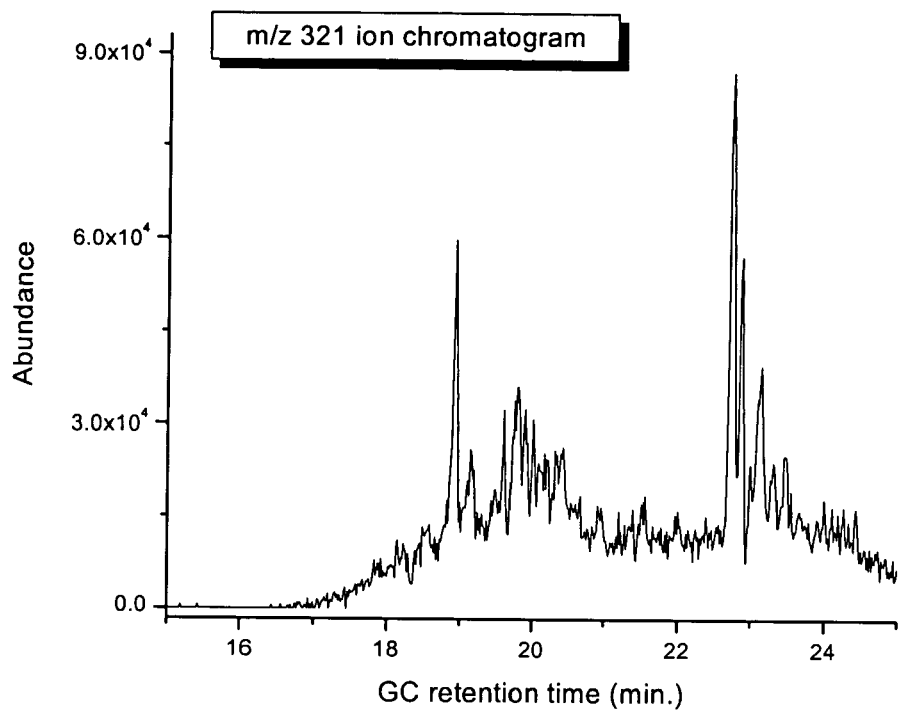
FIG. 62 is the m/z 321 ion chromatogram showing the presence of the aza dimethyltetramantanes in the TIC of a reaction product of Example 3.
Figure 63:
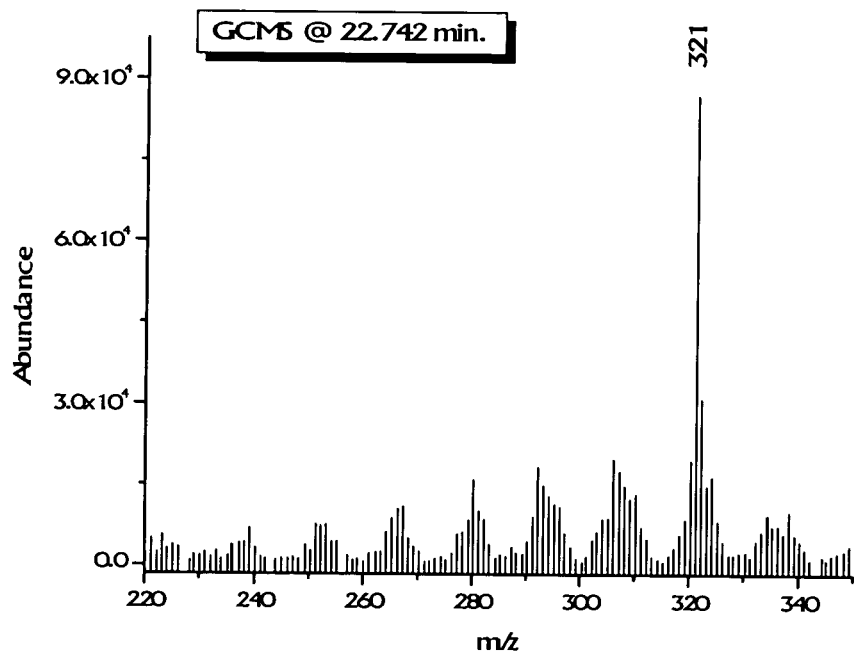
FIG. 63 is the mass spectrum of an aza dimethyltetramantane with GC/MS retention time of 22.742 minutes from FIG. 62.

To a portion of the hydroxylated tetramantanes in dry benzene (10 mL) was added mercury(II) oxide (100 mg) and iodine (170 mg). After the addition, the reaction mixture was irradiated for about 7 h in an atmosphere of nitrogen by the procedure reported by Suginome et al. (*J. Org. Chem.*, 1984, 49, 3753). Work-up gave a product mixture which was subjected to GC/MS characterization showing the presence of the oxatetramantane product 3 of FIG. 3. The chromatogens and mass spectra are provided as FIGS. 39–41.

Example 3

Azatetramantanes from a Feedstock Containing a Mixture of Tetramantane Isomers

In the next step, an azahomo tetramantane-ene may be produced from the above hydroxylated tetramantanes, or from photooxidized tetramantanes. To a stirred and ice cooled mixture of 98% methanesulfonic acid (1.5 mL) and dichloromethane (3.5 ml) was added solid sodium azide (1.52 g, 8.0 mmol). To that mixture was added the hydroxylated tetramantanes (2) as prepared in Example 2 above. To this resulting mixture was added in small increments sodium azide (1.04 g, 16 mmol) over a period of about 0.5 h. Stirring was continued for about 8 h at 20–25° C., and then the mixture was poured into ice water (ca. 10 ml). The aqueous layer was separated, washed with $CH_2Cl_2$ (3 mL), basified with 50% aqueous KOH-ice, and extracted with $CH_2Cl_2$ (10 mL×4). The combined extracts were dried with $Na_2SO_4$, and the solvent was removed to afford a brownish oil product. The product was characterized by GC/MS to show the presence of azahomo tetramantane-ene isomers (14). The chromatograms and mass spectra showing the azahomo molecules are shown in FIGS. 42–46.

In the next step, an epoxy azahomo tetramantane was made from the azahomo tetramantane-enes. The above mixture was treated with m-CPBA (1.1 eq.) in $CH_2Cl_2$—$NaHCO_3$ at a temperature of about 20° C. for about 12 h, and the reaction mixture was then worked up with a $CH_2Cl_2$ extraction to afford a crude product that was characterized by GC/MS (FIGS. 47–51) to show the presence of epoxy azahomo tetramantane.

In the next step, a mixture of N-formyl aza tetramantanes was prepared from the epoxy azahomo tetramantane mixture by irradiating the epoxy aza tetramantane mixture in cyclohexane using a high intensity Hg lamp for about 0.5 hours. The reaction was carried out in an argon atmosphere. Generally speaking, a simpler reaction product was obtained if the reaction was allowed to proceed for only a short time; longer periods gave a complex mixture. The initial product was characterized by GC/MS (FIGS. 52–56) as a mixture of N-formyl aza tetramantanes.

In a final step, aza tetramantanes were prepared from the above described N-formyl aza tetramantanes by mixing the N-formyl aza tetramantanes with 10 mL of 15% hydrochloric acid. The resultant mixture was heated to a boil for about 24 hours. After cooling, the mixture was subjected to a typical workup to afford a product which was characterized by GC/MS (FIGS. 57–63) showing the presence of aza tetramantanes.

Example 4

Oxidation of Hydroxylated Compound 2 to Keto Compound 1

Photohydroxylated iso-tetramantane containing a mixture of C-2 and C-3 hydroxylated iso-tetramantanes dissolved in acetone is prepared as set out in Example 2. The oxygenated components go into the solution but not all of the unreacted iso-tetramantane. Chromic acid-sulfuric acid solution is added dropwise to the solution until an excess is present, and the reaction mixture is stirred overnight. The acetone solution is decanted from the precipitated chromic sulfate and the unreacted iso-tetramantane, and is dried with sodium sulfate. The unreacted iso-tetramantane is recovered by dissolving the chromium salts in water and filtering. Evaporation of the acetone solution affords a white solid. This crude solid is chromatographed on alumina with standard procedures eluting first with 1:1 (v/v) benzene/light petroleum ether followed by ethyl ether or a mixture of ethyl ether and methanol (95:5 v/v) to collect the unreacted iso-tetramantane and the keto compound 1 (FIG. 3), respectively. Further purification by recrystallization from cyclohexane affords a pure product 1.

Alternatively, iso-tetramantane is directly oxidized to keto compound 1 according to the procedures of McKervey et al. (*J. Chem. Soc., Perkin Trans.* 1, 1972, 2691).

Reduction of Keto Compound 1 to C-2 Hydroxylated iso-Tetramantane 2a

As shown in FIG. 3, the keto compound 1 is reduced with lithium aluminum hydride (a little excess) in ethyl ether at low temperatures to prepare C-2 hydroxylated iso-tetramantane 2a. After completion of the reaction, the reaction mixture is worked up by adding saturated $Na_2SO_4$ aqueous solution to decompose excess hydride at low temperature. Decantation from the precipitated salts gives a dry ether solution, which, when evaporated, affords a crude monohydroxylated iso-tetramantane substituted at the secondary carbon, i.e. C-2 tetramantan-ol which is purified by recrystallization from cyclohexane.

C-2 Methyl Hydroxyl Iso-Tetramantane 2b from Keto Compound 1

Alternatively, as shown in FIG. 3, to a stirred solution of keto compound 1 (2 mmol) in dry THF (20 mL) at −78° C. (dry ice/methanol) is added dropwise a 0.8 molar solution (2.8 mL, 2.24 mmol) of methyllithium in ether. Stirring is continued for about 2 h at −78° C. and for another about 1 h at room temperature. Then, saturated ammonium chloride solution (1 mL) is added, and the mixture extracted with ether (2×30 mL). The organic layer is dried with sodium sulfate and concentrated to give the product 2b which is subjected to further purification by either chromatography or recrystallization.

Oxa iso-Tetramantane 3 from C-2 Hydroxylated Iso-Tetramantane 2a

A solution of C-2 hydroxylated iso-tetramantane 2a (1.32 mmol) in dry benzene (60 mL) containing mercury(II) oxide (850 mg) and iodine (1.006 g) is irradiated for about 7 h in an atmosphere of nitrogen by the procedure reported by Suginome et al. (*J. Org. Chem.*, 1984, 49, 3753). Work-up as reported gives a product which is subjected to preparative TLC on silica gel benzene/ether to give the product 3, as well as some amount of lactone 4 and the starting material 2a.

Oxa iso-Tetramantane 3 from C-2 Methyl Hydroxylated iso-Tetramantane 2b

A solution of C-2 methyl hydroxyl iso-tetramantane 2b (0.6 mmol) in dry benzene (30 mL) containing mercury(II) oxide (392 mg) and iodine (459 mg) is irradiated for about 3 h in an atmosphere of nitrogen by the above procedure. Work-up of the solution gives a product which is subjected to preparative TLC on silica gel with benzene/ether to give the product 3.

Oxa iso-Tetramantane 3 from C-2 Methyl Hydroxyl iso-Tetramantane 2b

C-2 methyl hydroxyl iso-tetramantane 2b (6.02 mmol) is added to a solution of TFPAA (trifluoroperacetic acid) in TFAA (trifluoroacetic acid) (13 g, 48.5 mmol) at 0° C. After being stirred for about 15 min. at 0° C., the reaction mixture is allowed to warm to r.t., stirring for about 1 h, and then poured into a solution of 15% NaOH (50 mL) with ice. The mixture is extracted with $CH_2Cl_2$ (3×15 mL). The combined extract is then washed with water and 5% aqueous $Na_2SO_3$. The organic layer is dried over $Na_2SO_4$ and the solvent evaporated. The residue is separated on a silica column eluting with a mixture of hexane-ether to afford the preduct oxa iso-tetramantane 3.

Example 5

Preparation of Lactone 4

Lactone 4 of FIG. 4 is prepared according to the general procedure of [Udding et al., *Tetrahedron Lett.*, 1968, 5719].

Preparation of Compound 5a from Compound 4

To a solution of lactone 4 (4.5 mmol) in dry toluene (80 mL) at −78° C. (cooled by dry ice/methanol) is added dropwise diisobutylaluminium hydride (20% in hexane, 5 mL) over a period of 20 min. The solution is stirred for 2 h at −78° C. and then poured into ice water. After removal of the precipitates, the solution is washed with water (1×50 mL) and dried with sodium sulfate. The solvent is evaporated to give the crude lactol 5a, which is recrystallized from hexane for further purification.

Preparation of Compound 5b from Compound 4

To a stirred solution of lactone 4 (2 mmol) in dry tetrahydrofuran (THF) (20 mL) at −78° C. (dry ice/methanol) is added dropwise a 0.8 molar solution (2.8 mL, 2.24 mmol) of methyllithium in ether. Stirring is continued for about 2 h at −78° C. and for about 1 h at room temperature. Then, saturated ammonium chloride solution (1 mL) is added, and the mixture extracted with ether (2×30 mL). The organic layer is dried with sodium sulfate and concentrated to give the crystalline product 5b which is recrystallized from petroleum ether for further purification.

Preparation of Compound 6a by Irradiation of 5a

To a solution of lactol 5a (1.2 mmol) in dry benzene (60 mL) containing pyridine (0.5 mL) is added mercury(II) oxide (520 mg) and iodine (610 mg). The solution is placed in a Pyrex vessel, flushed with nitrogen, and irradiated by a 100-W high-pressure mercury arc. The irradiation is discontinued after about 2 h. The solution is then washed with aqueous 5% sodium thiosulfate solution (30 mL), water (50 mL), and saturated sodium chloride solution (50 mL) and is dried with sodium sulfate. The solvent is evaporated to give the crude product 6a. Preparative TLC of this product with benzene affords two fractions A and B in the order of decreasing mobility. Fraction A is product 6a while fraction B is lactone 4.

Preparation of Compound 6b from 5b

To a solution of lactol 5b (1.2 mmol) in dry benzene (55 mL) containing pyridine (1 mL) are added mercury(II) oxide (477 mg) and iodine (588 mg). The solution is photolyzed as in the case of lactol 5a to give a crude product. The product is subjected to preparative TLC with benzene to give product 6b.

Example 6

Fragmentation of Keto Compound 1 to Unsaturated Carboxylic Acid 9 of FIG. 5

Fragmentation of iso-tetramantone 1 as prepared above to the unsaturated carboxylic acid 9 by an abnormal Schmidt reaction likewise follows McKervey et al. (*Synth. Commun.*, 1973, 3, 435) and is analogous to the behavior reported for adamantane and diamantane (Sasaki et al., *J. Org. Chem.*, 1970, 35, 4109; Fort, Jr. et al., *J. Org. Chem.*, 1981, 46(7), 1388).

Preparation of Compound 10 (Exo- and Endo-) from Acid 9

To 4.6 mmol of the carboxylic acid 9 are added 12 mL of glacial acetic acid and 3.67 g (4.48 mmol) of anhydrous sodium acetate. The mixture is stirred and heated to about 70° C. Lead(IV) acetate (3.0 g, 6.0 mmol, 90% pure, 4% acetic acid) is added in three portions over 30 min. Stirring is continued for 45 min at 70° C. The mixture is then cooled down to room temperature and diluted with 20 mL of water. The resulting suspension is stirred with 20 mL of ether, and a few drops of hydrazine hydrate are added to the dissolve the precipitated lead dioxide. The ether layer then is separated, washed several times with water and once with saturated sodium bicarbonate, and dried over anhydrous sodium sulfate. Removal of the ether gives an oily material from which a mixture of the two isomers (exo- and endo-) of compound 10 is obtained. Further purification and separation of the stereochemical isomers (exo- and endo-) can be achieved by distillation under vacuum.

Preparation of Compound 11 (exo- or endo-) from Compound 10 (exo- or endo-)

To a solution of compound 10 (0.862 mmol) in 5 mL of anhydrous ether is added 0.13 g (3.4 mmol) of lithium aluminum hydride, and the mixture is refluxed with stirring for about 24 h. The excess lithium aluminum hydride is destroyed by addition of water dropwise, and the precipitated lithium and aluminum hydroxides are dissolved in excess 10% hydrochloric acid. The ether layer is separated, washed with water, dried over anhydrous sodium sulfate, and evaporated to give compound 11 (mixtures of exo-11 and endo-11 isomers if using mixtures of exo-10 and endo-10). Further purification can be achieved by recrystallization from methanol-water.

Preparation of Compound 12 from Compound 11 (exo- and endo-Mixture)

A solution of a mixture of the alcohols 11 (1.05 mmol) in 5 mL of acetone is stirred in an Erlenmeyer flask at 25° C. To this solution is added dropwise 8 N chromic acid until the orange color persists, the temperature being kept at 25° C. The orange solution is then stirred at 25° C. for about additional 3 h. Most of the acetone is removed, and 5 mL of water is added to the residue. The aqueous mixture is extracted twice with ether, and the combined extracts are washed with saturated sodium bicarbonate, dried over anhydrous sodium sulfate, and evaporated to give crude 12. Sublimation on a steam bath gives pure 12.

Preparation of Compound 12 from exo-11

A solution of exo-11 (1.05 mmol) in 5 mL of acetone is stirred in an Erlenmeyer flask at 25° C. To this solution is added dropwise 8 N chromic acid until the orange color persisted, the temperature being kept at 25° C. The orange solution is then stirred at 25° C. for about additional 3 h. Most of the acetone is removed, and 5 mL of water is added to the residue. The aqueous mixture is extracted twice with ether, and the combined extracts are washed with saturated sodium bicarbonate, dried over anhydrous sodium sulfate, and evaporated to give crude 12. Sublimation on a steam bath gives pure 12.

Preparation of Compound 12 from Acid 9

A solution of the carboxylic acid 9 (4.59 mmol) in 15 mL of dry THF is stirred under dry argon and cooled to 0° C. A solution of 1.5 g (13.76 mmol) of lithium diisopropylamide in 25 mL of dry THF under argon is added through a syringe to the solution of 9 at such a rate that the temperature does not rise above 10° C. The resulting solution of the dianion of 9 is stirred at 0° C. for about 3 h. It is then cooled to −78° C. with a dry ice-acetone bath, and dry oxygen is bubbled slowly through the solution for about 3 more. A mixture of about 10 mL of THF and 1 mL water is added to the reaction mixture, which is then allowed to warm to room temperature and is stirred overnight. The solution is concentrated to about 10 mL at water pump pressure, poured into excess 10% HCl, and extracted with ether. The ether layer is washed with 5% NaOH to remove unreacted 9, which is recovered by acidification of the basic wash. The ether layer is dried over anhydrous sulfate and stripped to yield crude 9. Sublimation on a steam bath at 3–5 torr gives pure product.

Preparation of endo-11 from Compound 12

To a solution of ketone 12 (0.9 mmol) in 5 mL of anhydrous ether is added 0.13 g (3.4 mmol) of lithium aluminum hydride, and the mixture is stirred and refluxed for about 24 h. The excess lithium aluminum hydride is destroyed by dropwise addition of water, and the precipitated lithium and aluminum hydroxides are dissolved in excess 10% HCl. The ether layer is separated and dried over anhydrous sodium sulfate. Removal of the solvent gives the crude but stereochemically pure endo-11, which is further purified by sublimation on a steam bath under water pump pressure.

Oxa iso-tetramantane 3 from endo-11

To endo-11 (1.58 mmol) is added 25 mL of 50% sulfuric acid, and the solution is stirred vigorously at room temperature for about 24 h. The reaction mixture is then poured onto 100 g ice and the mixture extracted twice with ether. The ether extract is dried over anhydrous sodium sulfate and evaporated. The crude product is purified by sublimation on a steam bath at water pump pressure.

Example 7

Oxa iso-Tetramantane 3 from 6a or 6b with Methyllithium as Shown in FIG. 4

To a stirred solution of compound 6a (0.19 mmol) in dry THF (5 mL), a 0.8 molar solution (0.52 mL, 0.424 mmol) of methyllithium in ether is added dropwise at −78° C. Stirring is continued for about 1 h at −78° C. and for about another 1 h at room temperature. Water (10 mL) is then added and the mixture is extracted with ether (2×20 mL). The organic layer is washed with water (20 mL) and saturated sodium chloride solution (20 mL) and is dried with sodium sulfate. The solvent is evaporated to give crystals. The product is further purified by preparative TLC on silica gel using mixtures of benzene and ether.

Oxa iso-Tetramantane 3 from 6a by Column Chromatography on Silica Gel

Compound 6a (0.09 mmol) in dichloromethane (1 mL) is adsorbed on a column of silica gel for about 24 h. Elution of the column with dichloromethane gives the product 3 and some starting compound 6a.

Oxa iso-Tetramantane 3 from 6a Thermally

Compound 6a (0.09 mmol) is heated at 60° C. for about 30 min., and then subjected to preparative TLC with benzene/ether to yield the product 3 and the starting material 6a.

Example 8

Preparation of Thia-iso-Tetramantane Starting from iso-Tetramantone 6b of FIG. 6.

Preparation of Compound 7 from 6b

Compound 6b is prepared as described in a previous example. To a solution of compound 6b (0.78 mmol) in dry carbon tetrachloride (4 mL) is added to iodotrimethylsilane (312 mg, 1.56 mmol) at room temperature and the mixture is stirred for about 4 h. Water (20 mL) is then added and the mixture is extracted with ether (2×30 mL). The organic extract is washed with 5% sodium thiasulfate (20 mL), water, and saturated sodium chloride solution (30 mL) and is dried with sodium sulfate. The solvent is evaporated to give the crystalline product 7, which decomposes upon heating above about 90° C.

Preparation of Thia iso-Tetramantane 8 from Compound 7

Compound 7 (1 mmol) is dissolved in ethanol (10 mL) by warming. Sodium sulfide ($Na_2S.9H_2O$, 950 mg, 3.96 mmol) is added and the mixture is refluxed for about 10 h. Then, water (30 mL) is added and the mixture is extracted with ether (2×30 mL). The organic extract is washed with water (40 mL) and with saturated sodium chloride solution (40 mL) and is dried with sodium sulfate. The solvent is evaporated to give crystalline thia iso-tetramantane 8 which is further purified by preparative TLC on silica gel (hexane/benzene).

Example 9

Preparation of Compound 13 from Compound 12 (FIG. 6)

Compound 12 is prepared as described in a previous example starting from iso-tetramantone 1. Hydrogen sulfide is passed continuously for 2 days through a solution of compound 12 (1.06 mmol) in 15 mL of absolute ethanol. The solution is kept acidic by passing hydrogen chloride during every other 12-h period. The reaction mixture is kept at 0° C. during the passage of the gases. The resulting orange solution is extracted with 50 mL of ether in portions. The ether extracts are washed twice with water, dried over anhydrous sodium sulfate, and stripped to yield an orange semisolid. No further purification is needed and the material is used directly in the following reaction.

Thia iso-Tetramantane 8 from Compound 13

The crude compound 13 is dissolved in 100 mL of anhydrous ether, and 500 mg (13.16 mmol) of lithium aluminum hydride is added. The mixture is stirred at reflux for about 2 days. Excess lithium aluminum hydride is destroyed with water, and the precipitated lithium and aluminum hydroxides are dissolved in excess 10% HCl. The layers are separated, and the aqueous phase is extracted with 50 mL of ether. The combined ether extracts are dried over anhydrous sodium sulfate and stripped. Sublimation of the residue on a steam bath at water pump pressure gives the product 8 contaminated with a small amount of endo-11. This mixture is chromatographed on neutral alumina. Elution with hexane gives pure 8; subsequent elution with ether gives endo-11. Further purification of 8 is by sublimation on a steam bath at water pump pressure.

Example 10

Preparation of Aza iso-Tetramantane from iso-Tetramantane (FIGS. 7 & 8)

In this example, an aza iso-tetramantane is prepared from a single tetramantane isomer, iso-tetramantane, as shown in FIGS. 7–8. As with the reactions using a mixture of tetramantanes shown in Example 2, this synthetic pathway begins with the photo-hydroxylation of iso-tetramantane using the method of Example 2 or chemical oxidation/reduction to the hydroxylated compound 2a shown in FIG. 7.

This photo-hydroxylated iso-tetramantane containing a mixture of C-2 and C-3 hydroxylated iso-tetramantanes is converted to keto compound 1 via the process set out in Example 4.

In the next step, the azahomo iso-tetramantane-ene 14 is prepared from the hydroxylated compound 2 using the general method set out in Example 3.

In the next step, an epoxy azahomo iso-tetramantane 15 is prepared also as shown in Example 3.

In the next step, N-acyl aza iso-tetramantane 16b is prepared from the epoxy azahomo iso-tetramantane 15b by irradiating the epoxy azahomo iso-tetramantane 15b in cyclohexane for about 0.5 hours with a UV lamp. The radiation passes through a quartz filter and the reaction is carried out under an argon atmosphere. Generally speaking, a single product is formed when the reaction is allowed to proceed for only a short time: longer periods gives a complex mixture of products. Products may be isolated by chromatographic techniques.

N-formyl aza iso-tetramantane 16a can be similarly prepared from the epoxy azahomo iso-tetramantane 15a.

In the next step, the aza iso-tetramantane 17 is prepared from N-acyl aza-isotetramantane 16b by heating the N-acyl aza iso-tetramantane 16b (5 mmol) to reflux for about 5 hours with a solution of 2 g powdered sodium hydroxide in 20 mL diethylene glycol. After cooling, the mixture is poured into 50 mL water and extracted with ethyl ether. The ether extract is dried with potassium hydroxide. The ether is distilled off to afford the product aza iso-tetramantane 17. The hydrochloride salt is generally prepared for analysis. Thus, dry hydrogen chloride is passed into the ether solution of the amine, whereby the salt separates out as a crystalline compound. The salt may be purified by dissolving it in ethanol, and precipitating with absolute ether. Typically, the solution is left undisturbed for several days to obtain complete crystallization.

Alternatively, the aza iso-tetramantane 17 may be prepared from the N-formyl aza iso-tetramantane 16a by mixing the N-formyl aza iso-tetramantane 16a (2.3 mmol) with 10 mL of 15% hydrochloric acid as shown in Example 3.

Example 11

Preparation of the Aza iso-Tetramantane 17 by Fragmentation of a Keto Compound 1 (FIG. 8)

To a solution of compound 12 (FIG. 5) (1.6 mmol) in a mixture of pyridine and 95% ethanol (1:1) is added 250 mg (3.6 mmol) of hydroxylamine hydrochloride, and the mixture is stirred at reflux for about 3 days. Most of the solvent is evaporated in a stream of air, and the residue is taken up in 25 mL of water. An ether extract of the aqueous solution is washed with 10% HCl to extract the oxime 18. Neutralization of the acid wash with 10% sodium hydroxide precipitates the oxime 18, which is filtered off and recrystallized from ethanol-water.

In a final step, the aza iso-tetramantane 17 is prepared from compound 18 by the dropwise addition of a solution of compound 18 (0.98 mmol) in 25 mL of anhydrous ether to a stirred suspension of 250 mg (6.58 mmol) of lithium aluminum hydride in 25 mL of anhydrous ether. The mixture is stirred at reflux for about 2 days. Excess lithium aluminum hydride is destroyed with water, and the precipitated lithium and aluminum hydroxides are dissolved in excess 25% sodium hydroxide. The resulting basic solution is extracted twice with ether, and the combined extracts are then washed with 10% HCl. Neutralization of the acidic wash with 10% sodium hydroxide precipitates product 6, which is extracted back into fresh ether. The ether solution is dried over anhydrous sodium sulfate and stripped. The crude product is purified by repeated sublimation on a steam bath under vacuum.

Example 12

Monobromination of Heterodiamondoids

Figure 13:
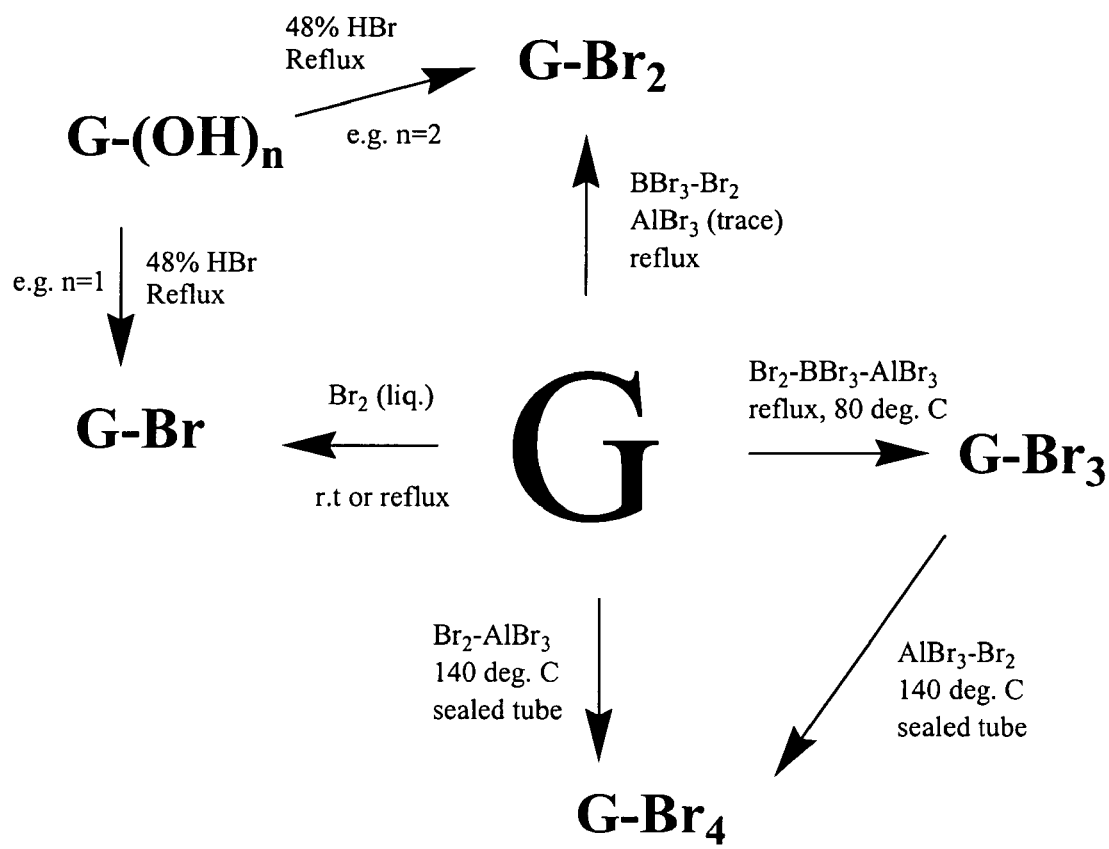
Figure 14:
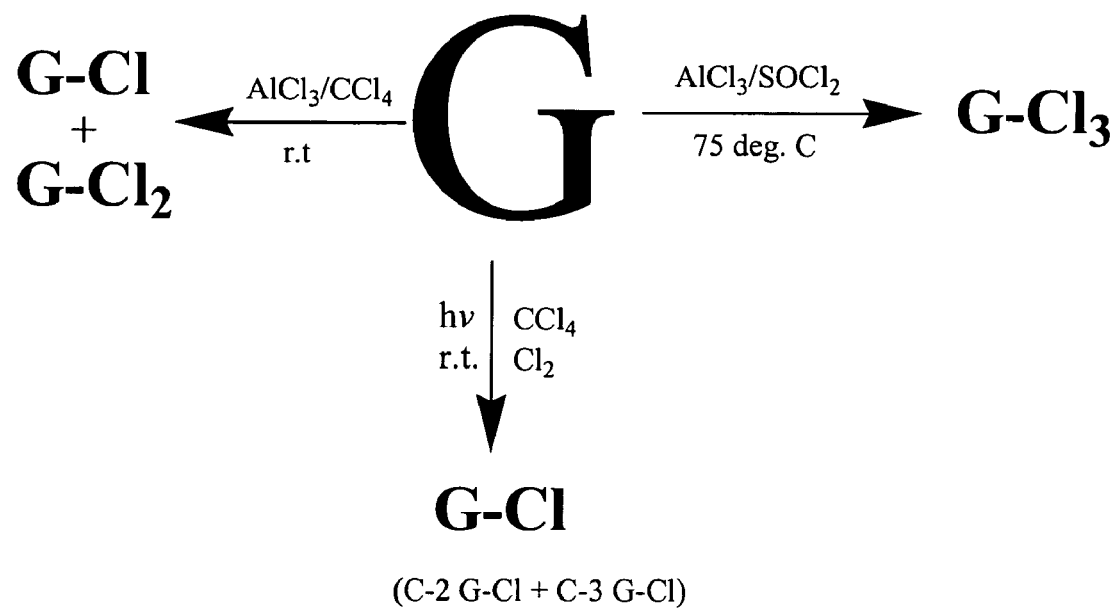

As shown in FIG. 13, a heterodiamondoid (7.4 mmol) is mixed with anhydrous bromine (74 mmol) in a 150 mL round bottom flask. While stirring, the mixture is heated in an oil bath for about 4.5 h, whereby the temperature is gradually raised from an initial 30° C. to 105° C. After cooling, the product monobrominated heterodiamondoid dissolved in excess bromine is taken up with 100 mL carbon tetrachloride and poured into 300 mL ice water. The excess bromine is then removed with sodium hydrogen sulfide while cooling with ice water. After the organic phase has been separated, the aqueous solution is extracted once more with carbon tetrachloride. The combined extracts are washed three times with water. After the organic phase has been dried with calcium chloride, the solvent is distilled off and the last residues are removed under vacuum. The residue is dissolved in a small amount of methanol and crystallized in a cold bath. Further purification of the crystals is carried out by sublimation under vacuum.

Example 13

Dibromination of Heterodiamondoids Without Catalysts

As shown in FIG. 13, a heterodiamondoid (37 mmol) is heated to 150° C. for about 22 h with anhydrous bromine (0.37 mol) in a pressure vessel. Usual work-up and recrystallization of the reaction product from methanol is performed as described above. The crystals are sublimated in vacuum. The sublimate is recrystallized several times from a very small amount of n-hexane affording a dibrominated derivative.

Example 14

Brominated Heterodiamondoids from Hydroxylated Compounds (FIG. 13)

A mixture of a suitable hydroxylated heterodiamondoid and excess 48% hydrobromic acid is heated to reflux for a few hours (which can be conveniently monitored by GC analysis), cooled, and extracted with ethyl ether. The extract is combined and washed with aqueous 5% sodium hydroxide and water, and dried. Evaporation and normal column chromatography on alumina eluting with light petroleum ether, hexane, or cyclohexane or their mixtures with ethyl ether affords the bromide with reasonable high yields.

Example 15

$G-CH_2CH_2—Br$ from $G-Br$

A solution of a suitable monobrominated heterodiamondoid G-Br (0.046 mole) in 15 mL n-hexane in a 150-mL three-necked flask equipped with a stirrer, a gas inlet tube and a gas discharge tube with a bubble counter is cooled to −20 to −25° C. in a cooling bath. While stirring one introduces 4.0 g powdered freshly pulverized aluminum bromide of high quality, and ethylene is conducted in such a way that the gas intake can be controlled with the bubble counter. The reaction starts with a slight darkening of the color and is completed after about 1 h. The reaction solution is decanted from the catalyst into a mixture of ether and water. The ether layer is separated off, and the aqueous phase is extracted once more with ether. The combined ether extracts are washed with water and dilute sodium carbonate aqueous solution. After they have been dried over calcium chloride, the solvent is distilled off. Recrystallizing from methanol affords the pure heterodiamondoid ethyl bromide $G-CH_2CH_2—Br$.

Example 16

G-CH=CH—Br from G-Br

Step 1: in a 150-mL two-necked flask with a stirrer and a drying tube, a mixture of 0.069 mole of a suitable monobromonated heterodiamondoid G-Br and 20 mL vinyl bromide is cooled to −65° C. in a cooling bath. While stirring, 4.5 g powdered aluminum bromide is added in portions and the mixture is stirred for an additional about 3 hours at the same temperature. Then the reaction mixture is poured into a mixture of 30 mL water and 30 mL ethyl ether. After vigorously stirring, the ether layer is separated and the aqueous layer is extracted once more with ether. The combined ether extracts are washed with water and dilute sodium carbonate solution. After it has been dried with calcium chloride and the solvent has been distilled off, the residue is distilled under vacuum.

Step 2: a solution of 0.7 g fine powdered potassium hydroxide and the above compound (0.012 mole) in 10 mL diethylene glycol is heated to 220° C. in the oil bath for 6 hours. After cooling down the mixture is diluted with 30 mL water and exacted with ethyl ether. The ether extract is washed twice with water and dried over calcium chloride. The residue left behind after the ether has been distilled off is sublimated in vacuum, and if necessary, the compound can be recrystallized from methanol.

G-C≡C—Br can also be formed from G-Br using this method and appropriate starting materials.

Example 17

G-$C_6H_4$—Br from G-Br 1.1 g sublimated iron(III) chloride and high pure $C_6H_5Br$ (excess) are placed in a 150-mL three-necked flask, which is equipped with a stirrer, a reflux condenser and a dropping funnel. While stirring and heating in the steam bath, a suitable monobrominated heterodiamondoid G-Br (0.018 mole) is slowly added to the above flask over about 30 minutes. The reaction mixture is heated for about an additional 3 hours until the production of hydrogen bromide drops off. The mixture is kept standing over night and poured onto a mixture of ice and hydrochloric acid. The organic phase is separated out and the aqueous solution is extracted twice with benzene. The combined benzene extracts are washed several times with water and dried with calcium chloride. The residue solidifies upon cooling and is completely free of the solvent in vacuum. Recrystallization from a small amount of methanol while cooling with $CO_2$/trichloroethylene and further sublimation under vacuum afford a pure product.

Example 18

Monochlorination of Heterodiamondoids

A solution of 0.074 mole of a heterodiamondoid and 10 mL (8.5 g, 0.092 mole) of tert-butyl chloride in 40 mL of anhydrous cyclohexane is prepared in a 0.1 L, three-necked, round-bottom flask fitted with a thermometer, a stirrer, and a gas exhaust tube leading to a bubbler submerged in water. The catalyst, aluminum chloride (total 0.46 g, 0.006 mole) is added in batches of 0.05 g at regular intervals over a period of about 8 hours. Progress of the reaction is followed conveniently by the rate of escaping isobutane gas. Upon completion of the reaction, 10 mL of 1.0 N hydrochloride acid solution is added with vigorous stirring, followed by 50 mL of ethyl ether. The organic layer is separated, washed with 10 mL of cold water and 10 mL of a 5% sodium bicarbonate solution, and dried over anhydrous calcium chloride. After removal of the solvents under reduced pressure, the crude product is obtained. GC analysis of this material reveals a composition of mainly monochlorinated heterodiamondoid with a small amount of unreacted heterodiamondoid. If necessary, recrystallization of a sample of this material from ethanol at −50° C. affords a pure monochlorinated heterodiamondoid.

Example 19

Monohydroxylation of Heterodiamondoids

A solution of 11.0 mmol of a heterodiamondoid in 18.7 g of methylene chloride is mixed with 4.22 g of a solution of 1.03 g (13.5 mmol) of peracetic acid in ethyl acetate. While being stirred vigorously, the solution is irradiated with a 100-watt UV light placed in an immersion well in the center of the solution. Gas evolution is evident from the start. The temperature is maintained at 40–45° C. for an about 21-hour irradiation period. At the end of this time, about 95% of the peracid had been consumed. The solution is concentrated to near dryness, treated twice in succession with 100-mL portions of toluene and reevaporated to dryness. Final drying in a desiccator affords a white solid. A portion of the above material is dissolved in a minimum amount of benzene-light petroleum ether. This solution is then subjected to chromatography on alumina in the usual manner eluting with firstly 1:1 benzene/light petroleum ether, followed by a mixture of methanol and ethyl ether to collect the unreacted heterodiamondoid, and the hydroxylated heterodiamondoid isomers, respectively. Further separation of the isomers can be achieved by using HPLC technique.

Example 20

Polyhydroxylation of Heterodiamondoids

Into a 4-neck flask immersed in a cooling bath and equiped with a low temperature condenser (−20° C.), and an air driven, well sealed mechanical stirrer, a solid addition funnel and a thermocouple, is added 0.037 mole of a heterodiamondoid, 150 mL methylene chloride, 200 mL double distilled water, 192 grams sodium bicarbonate and 300 mL t-butanol. The mixture is stirred and cooled to 0° C. and 200 grams 1,1,1-trifluoro-2-propanone (TFP) are added. The mixture is stirred and cooled down to −8° C. 200 grams oxone are added from the solid addition funnel over the course of 3 hours. The reaction mixture is stirred at 0° C. overnight (16 hours). The TFP is recovered by distillation (heating pot to 40° C. and condensing TFP in a receiver immersed in dry ice/acetone). The remainder mixture is filtered by suction and a clear solution is obtained. The solution is rotavapped to dryness, providing a mixture of polyhydroxylated heterodiamondoids that are purified by chromatography and/or recrystallization.

Example 21

Figure 15:
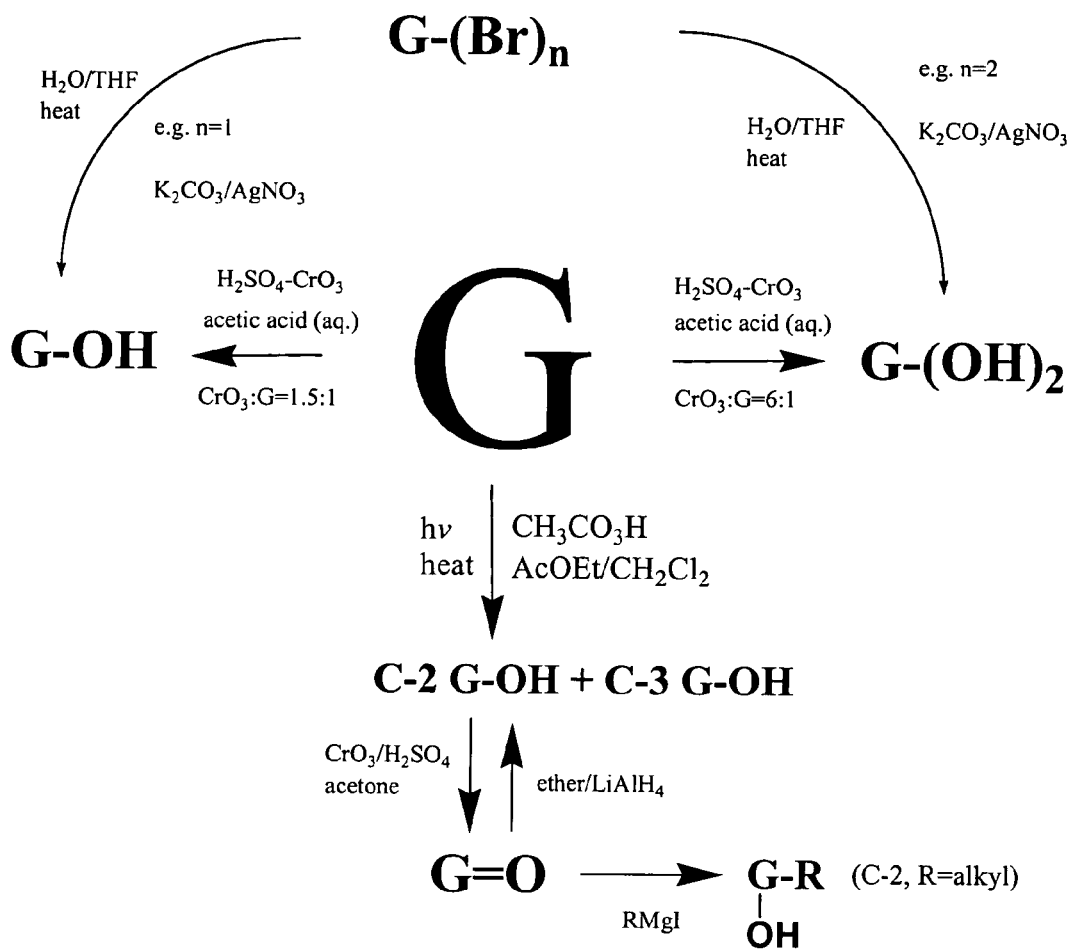
Figure 16:
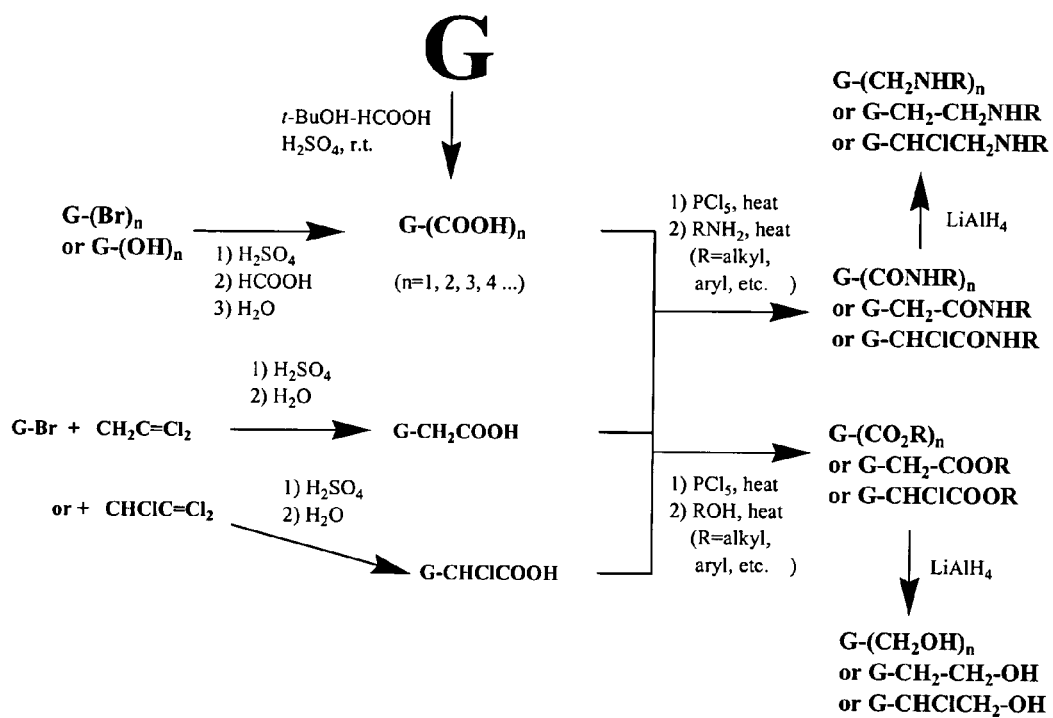
Figure 17:
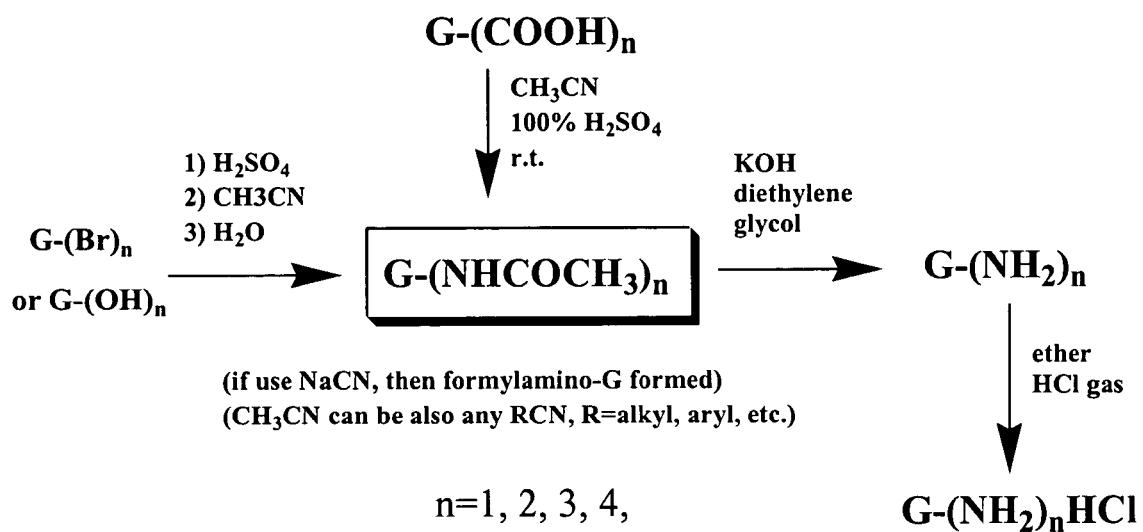
Figure 18:
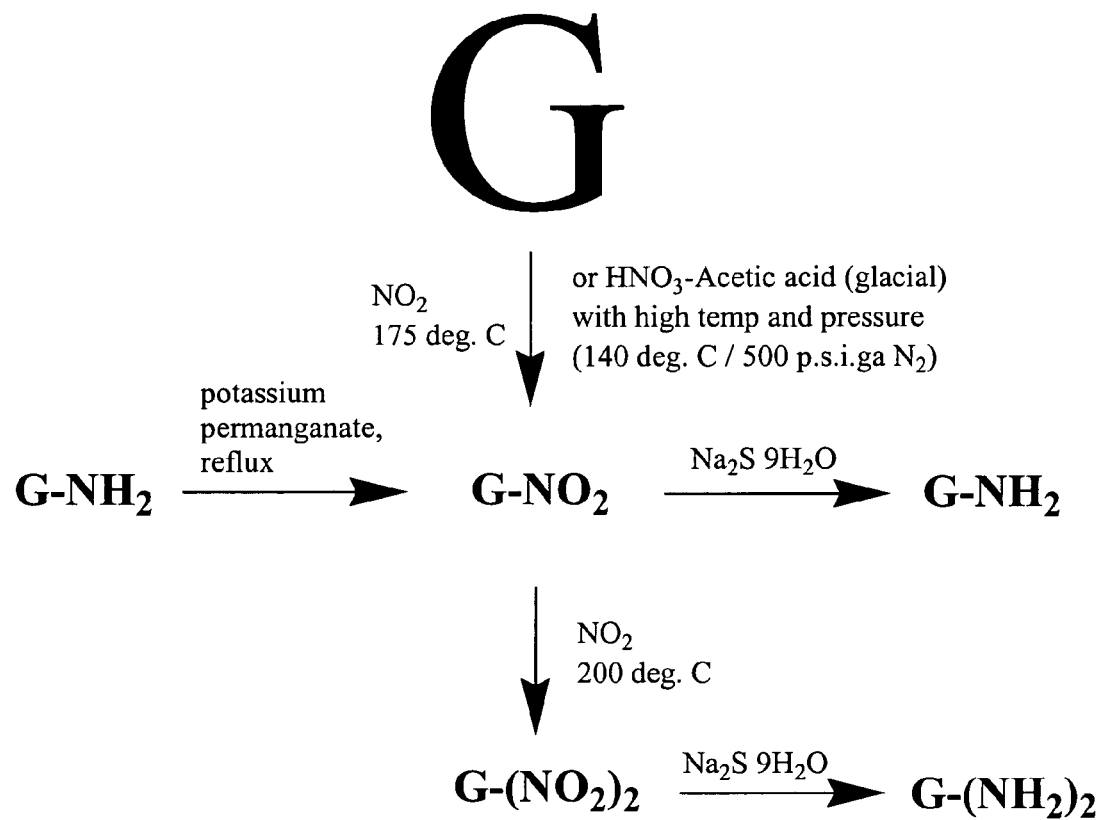
Figure 19:
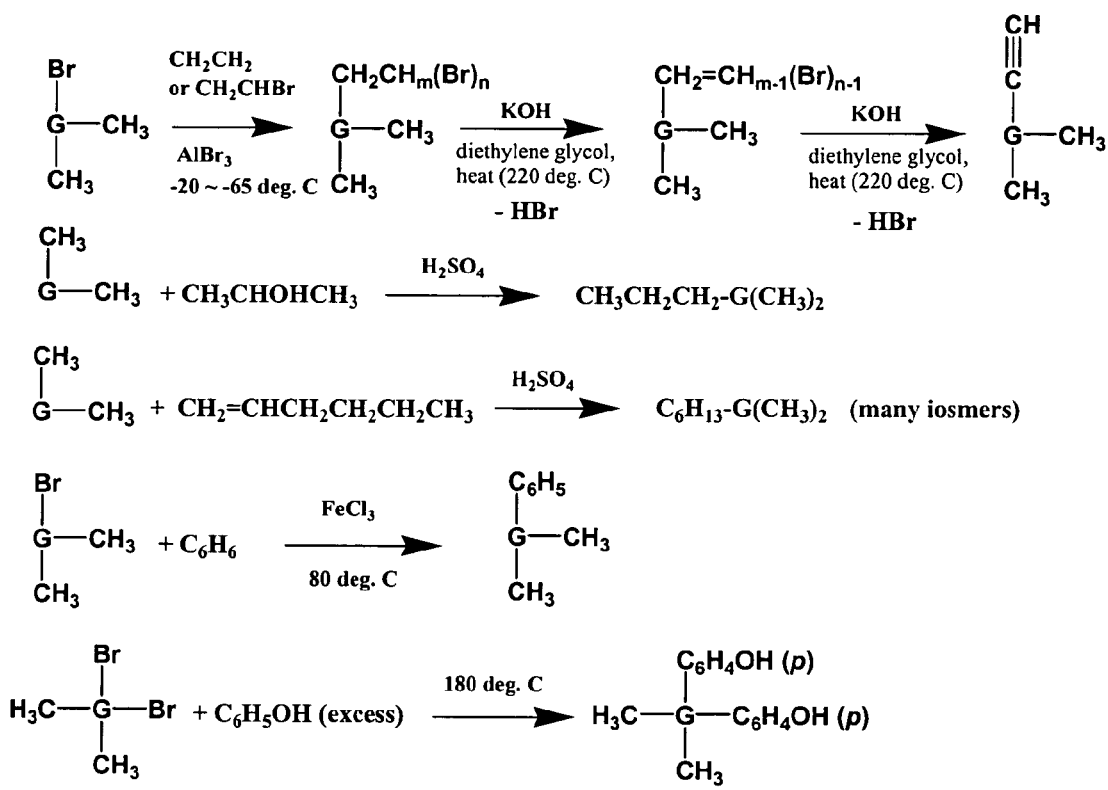
Figure 20:
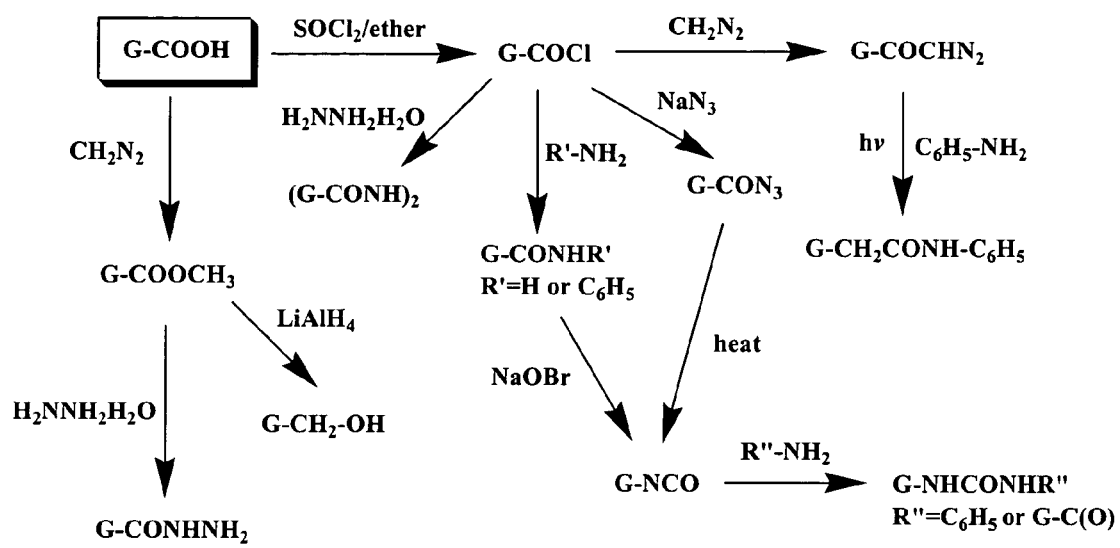

Monohydroxylated Heterodiamondoids from Monobrominated Compounds (FIG. 15)

A suitable monobrominated heterodiamondoid (0.066 mol) is heated to reflux for about 1 h in a round bottom flask, which is equipped with a stirrer and a reflux condenser, while stirring and adding 35 mL water, 3.5 mL tetrahydrofuran, 2.0 g potassium carbonate and 1.3 g silver nitrate. After cooling, the reaction product, which has crystallized out, is separated out and is extracted with tetrahydrofuran. The extract is diluted with water and the precipitate is suctioned off, dried and purified by sublimation under vacuum.

Example 22

G-$CH_2CH_2$—OH from G-$CH_2CH_2$Br (FIG. 15)

A suitable G-$CH_2CH_2$—Br (0.066 mol) is heated to reflux for about 1 h in a round bottom flask, which is equipped with a stirrer and a reflux condenser, while stirring and adding 35 mL water, 3.5 mL tetrahydrofuran, 2.0 g potassium carbonate and 1.3 g silver nitrate. After cooling, the reaction product is separated out and is extracted with chloroform. Evaporating the solvent affords the product after purification by column chromatography.

Example 23

C-2 G-OH from G=O (FIG. 15)

A suitable hetero diamondoidone G=O is reduced with lithium aluminum hydride (a little excess) in ethyl ether at low temperatures. After completion of the reaction, the reaction mixture is worked up by adding saturated $Na_2SO_4$ aqueous solution to decompose excess hydride at low temperature. Decantation from the precipitated salts gives a dry ether solution, which, when evaporated, affords a crude C-2 monohydroxylated heterodiamondoid substituted at the secondary carbon, i.e. C-2 G-OH. Further recrystallization from cyclohexane gives an analytically pure sample.

Example 24

Diesterified Heterodiamondoids from Dihydroxylated Compounds

To 2 mL of dioxane is added a dihydroxylated heterodiamondoid (1.0 mmol) and triethylamine (2.2 mmol) at a temperature of 50° C. The resultant mixture is added dropwise to a solution of acrylic acid chloride (2.2 mmol) in dioxane (2 mL). The mixture is maintained at 50° C. for about 1 hour. The product is analyzed by GC. When the analysis confirms the formation of the desired diacrylate, the compound is isolated using standard methods.

Example 25

Oxidation of Heterodiamondoids to Heterodiamondoidones

A solution of 11.0 mmol of a suitable heterodiamondoid in 18.7 g of methylene chloride is mixed with 4.22 g of a solution of 1.03 g (13.5 mmol) of peracetic acid in ethyl acetate. While being stirred vigorously, the solution is irradiated with a 100-watt UV light placed in an immersion well in the center of the solution. Gas evolution is evident from the start. The temperature is maintained at 40–45° C. for an about 21-hour irradiation period. At the end of this time, about 95% of the peracid had been consumed. The solution is concentrated to near dryness, treated twice in succession with 100-mL portions of toluene and reevaporated to dryness. Final drying in a desiccator affords a crude white solid.

The crude hydroxylated heterodiamondoid mixture is then partially dissolved in acetone. The oxygenated components go into the solution but not all of the unreacted heterodiamondoid. Chromic acid-sulfuric acid solution is added dropwise until an excess is present, and the reaction mixture is stirred overnight. The acetone solution is decanted from the precipitated chromic sulfate and the unreacted heterodiamondoid, and is dried with sodium sulfate. The unreacted heterodiamondoid is recovered by dissolving the chromium salts in water and filtering. Evaporation of the acetone solution affords a white solid. This crude solid is chromatographed on alumina with standard procedures eluting first with 1:1 (v/v) benzene/light petroleum ether followed by ethyl ether or a mixture of ethyl ether and methanol (95:5 v/v) to collect the unreacted heterodiamondoid and the heterodiamondoidone, respectively. Further purification by recrystallization from cyclohexane affords a pure heterodiamondoidone.

Example 26

2,2-Bis(4-hydroxyphenyl) Heterodiamondoids from Keto Compounds

A flask is charged with a mixture of a heterodiamondoidone (0.026 mole), phenol (16.4 g, 0.17 mole), and butanethiol (0.15 mL). Heat is applied and when the reaction mixture becomes liquid at about 58° C., anhydrous hydrogen chloride is introduced until the solution becomes saturated. Stirring is continued at about 60° C. for several hours, during which period a white solid begins to separate out from the reddish-orange reaction mixture. The solid obtained is filtered off, washed with dichloromethane and dried to afford the bisphenol heterodiamondoid product. It is purified by sublimation after recrystallization from toluene.

Example 27

2,2-Bis(4-aminophenyl) Heterodiamondoids from Keto Compounds

To a solution of a heterodiamondoidone (0.041 mole) in 15 mL of 35% HCl aqueous solution in a 100 mL autoclave equipped with a stirrer is added excess aniline (15.7 g, 0.17 mole) and the mixture is stirred at about 120° C. for about 20 hours. After cooling, the solution is made basic with NaOH aqueous solution to pH 10 and the oily layer is separated and distilled to remove the unreacted excess aniline. The residual crude product is recrystallized from benzene.

Example 28

2,2-Bis[4-(4-aminophenoxy)phenyl] Heterodiamondoids from Bisphenol Heterodiamondoids A mixture of a 2,2-bis(4-hydroxyphenyl) heterodiamondoid (0.01 mole), p-fluoronitrobenzene (3.1 g, 0.022 mole), potassium carbonate (3.31 g, 0.024 mole) and N,N,-dimethylacetamide (DMAc, 10 mL) is refluxed for about 8 hours. The mixture is then cooled and poured into a ethanol/water mixture (1:1 by volume). The crude product is crystallized from DMF to provide yellow needles of the 2,2-bis [4-(4-nitrophenoxy)phenyl] heterodiamondoid.

Hydrazine monohydrate (20 mL) is added dropwise to a mixture of the above product (0.002 mole), ethanol (60 mL), and a catalytic amount of 10% palladium on activated carbon (Pd/C, 0.05 g) at the boiling temperature. The reaction mixture is refluxed for about 24 hours, and the product 2,2-Bis[4-(4-aminophenoxy)phenyl] heterodiamondoid is precipitated during this period. The mixture is then added to enough ethanol to dissolve the product and filtered to remove Pd/C. After cooling, the precipitated crystals are isolated by filtration and recrystallized from 1,2-dichlorobenzene.

Example 29

Mononitration of Heterodiamondoids

A mixture of 0.05 mole of a heterodiamondoid and 50 mL of glacial acetic acid is charged to a stirred stainless 100 mL autoclave which is pressurized with nitrogen to a total pressure of 500 p.s.i.ga. After the mixture is then heated to 140° C., 9.0 g (0.1 mole) of concentrated nitric acid is introduced into the reaction zone by means of a feed pump at a rate of 1–2 mL per minute. When the acid feed is completed, the reaction temperature is maintained at 140° C. for 15 minutes, after which time the reaction mixture is cooled down to room temperature and diluted with an excess of water to precipitate the products. The filtered solids are slurried with a mixture of 10 mL of methanol, 15 mL of water, and 1.7 g of potassium hydroxide for 18 hours at room temperature. After dilution with water, the alkali-insoluble material is extracted by light petroleum ether. The petroleum ether extracts are washed by water and dried over anhydrous magnesium sulfate. Concentration of this solution affords a white solid. The aqueous alkali solution from which the alkali-insoluble material had been extracted is cooled to 0–3° C. and neutralized by the dropwise addition of an aqueous acetic acid-urea mixture to regenerate some more products. GC analysis shows that the alkali-insoluble sample is mainly mononitro heterodiamondoid.

Example 30

Monocarboxylation of Heterodiamondoids

A mixture of 29.6 g (0.4 mole) tert-butanol and 55 g (1.2 mole) 99% formic acid is added dropwise over about 3 hours to a mixture of 470 g 96% sulfuric acid and 0.1 mole heterodiamondoid dissolved in 100 mL cyclohexane while stirring vigorously at room temperature. After decomposing with ice, the acids are isolated and purified by recrystallization from methanol/water giving the monocarboxylated heterodiamondoid.

Example 31

G-CHClCOOH from G-Br

A mixture of a suitable monobrominated heterodiamondoid G-Br (0.012 mole) and 9.0 g trichloroethylene CHCl=CCl$_2$ is added dropwise in the course of about 4 hours into 24 mL 90% sulfuric acid at 103–106° C. while stirring. After the addition is completed, the mixture is stirred for about an additional 2 hours at the specified temperature, then cooled down and hydrolyzed with ground ice. The precipitated product can be freed from the neutral fraction by dissolution in dilute sodium hydroxide solution and extraction with ethyl ether. When acidified with dilute hydrochloric acid solution, the carboxylic acid precipitates out of the alkaline solution.

Example 32

G-NHCOCH$_3$ from G-Br

A suitable monobrominated heterodiamondoid G-Br (0.093 mole) is dissolved in 150 mL acetonitrile. While stirring, 30 mL concentrated sulfuric acid is slowly added to the above solution, whereby the mixture heats up. After it has been left standing for about 12 hours, the solution is poured into 500 mL ice water, whereby the monoacetamino heterodiamondoid separates out in high purity.

Example 33

G-NHCHO from G-COOH

Within 7 minutes 8.16 g (0.17 mole) sodium cyanide and a suitable monocarboxylated heterodiamondoid G-COOH (0.028 mole) are added to 100 mL 100% sulfuric acid while stirring vigorously. After ½ hour, decomposition is carried out by pouring the reaction mixture onto 250 g crushed ice which is then made basic by the addition of a sufficient amount of odium hydroxide solution and extracted five times with benzene/ether. The solvent is removed in vacuo from the combined extracts and the residue is recrystallized from benzene/hexane.

Example 34

G-CO$_2$CH$_2$CH$_3$ from G-COOH via G-COCl 0.017 mole of a suitable monocarboxylated heterodiamondoid G-COOH is mixed with 4.2 g PCl$_5$ in a 50-mL flask with a stirrer and a reflux condenser. The reaction starts after 30–60 seconds with liquefaction of the reaction mixture. The mixture is heated for an additional about 1 hour while stirring on the steam bath. The POCl$_3$ formed is distilled off under vacuum. The acid chloride left behind as a residue is cooled with ice water, and 6.0 mL absolute ethanol is added dropwise. The mixture is heated for an additional around 1 hour on the steam bath and then poured into 50 mL water after it has been cooled down. The ester is taken up with ethyl ether and then washed with potassium carbonate aqueous solution and water. After drying, fractionation is carried out over calcium chloride under vacuum.

Example 35

G-CH=CH$_2$ from G-Br

Step 1: a solution of a suitable monobrominated heterodiamondoid G-Br (0.046 mole) in 15 mL n-hexane in a 150-mL three-necked flask equipped with a stirrer, a gas inlet tube and a gas discharge tube with a bubble counter is cooled to −20 to −25° C. in a cooling bath. While stirring one introduces 4.0 g powdered freshly pulverized aluminum bromide of high quality, and ethylene is conducted in such a way that the gas intake can be controlled with the bubble counter. The reaction is completed after about 1 h. The reaction solution is decanted from the catalyst into a mixture of ether and water. The ether layer is separated off, and the aqueous phase is extracted once more with ether. The combined ether extracts are washed with water and dilute sodium carbonate aqueous solution. After they have been dried over calcium chloride, the ether is distilled off. The residue is separated by distillation under vacuum. Recrystallizing from methanol affords crystals of the heterodiamondoidyl ethyl bromide G-$CH_2CH_2$Br.

Step 2: a solution of 0.7 g fine powdered potassium hydroxide and the above heterodiamondoidyl ethyl bromide G-$CH_2CH_2$Br (0.012 mole) in 10 mL diethylene glycol is heated to 220° C. in the oil bath for 6 hours. After cooling down the mixture is diluted with 30 mL water and exacted with ethyl ether. The ether extract is washed twice with water and dried over calcium chloride. The residue left behind after the ether has been distilled off is sublimated in vacuum, and if necessary, the compound can be recrystallized from methanol.

Example 36

G-C≡CH from G-Br

Step 1: in a 150-mL two-necked flask with a stirrer and a drying tube, a mixture of 0.069 mole of a suitable monobromonated heterodiamondoid and 20 mL vinyl bromide is cooled to −65° C. in a cooling bath. While stirring, 4.5 g powdered aluminum bromide is added in portions and the mixture is stirred for an additional about 3 hours at the same temperature. Then the reaction mixture is poured into a mixture of 30 mL water and 30 mL ethyl ether. After vigorously stirring, the ether layer is separated and the aqueous layer is extracted once more with ether. The combined ether extracts are washed with water and dilute sodium carbonate solution. After it has been dried with calcium chloride and the solvent has been distilled off, the residue is distilled under vacuum.

Step 2: 15 g powdered potassium hydroxide in 30 mL diethylene glycol is heated to reflux with 0.046 mole of the above product for about 9 hours in the oil bath. Compound monoethynylated heterodiamondoid which is formed is then sublimated in the condenser and must be returned to the reaction mixture from time to time. At the end of the reaction time, the reaction mixture is distilled until no more solid particles go over. The distillate is extracted with ethyl ether and the ether phase is washed with water and dried over calcium chloride. A short time after the ether has been distilled off, the residue solidifies. It is sublimated under vacuum and, if necessary, recrystallized from methanol.

Example 37

G-O—$CH_2$—$C_6H_5$ from G-Br

To a solution of benzyl alcohol $C_6H_5$—$CH_2$—OH (0.28 mole) containing 0.03 mole of sodium benzylate is added 0.01 mole of G-Br and the resulting mixture heated for about 4 hours, during which a copious precipitate NaBr formed. After cooling, the reaction mixture is poured into water and the aqueous phase extracted with ethyl ether and the later dried over sodium sulfate, then evaporated. Most of the benzyl alcohol is removed by distillation, leaving ca. 4 mL of oil which is chromatographed over alumina. Elution with petroleum ether afford the product.

Example 38

Heterodiamondoidyl acetic acid, e.g. G-COOH is prepared as shown in Example 29. The corresponding acid chloride G-COCl is obtained by stirring a mixture of the acid and thioyl chloride diluted with petroleum ether at room temperature for about 50 hours. Treatment of the acid chloride G-COCl with an excess amount of ethereal diazomethane gives the heterodiamondoidyl acetyl diazomethane G-$COCHN_2$. Reactions of the acid chloride G-COCl with such amines as ammonia and aniline give the corresponding amides, in those cases G-$CONH_2$ and G-CONH$C_6H_5$ respectively.

Example 39

G-$CONH_2$ from G-COCl

Concentrated aqueous ammonia (11.0 mL) is, over a period of 30 min., stirred, drop by drop, into a stirred solution of G-COCl, prepared from 5.5 mmole of G-COOH, in 4.0 mL of dry THF under cooling with ice-water. The stirring is continued for about 6 hours, and then, the precipitates are filtered out. The addition of water to the filtrate gives the second crop. The combined precipitates are washed with water and dried to give the title compound.

Example 40

Hofmann Reaction of G-$CONH_2$

Into an ice-cooled bromine-alkali reagent, freshly prepared from 1.0 g of bromine, 1.0 g of sodium hydroxide, and 10 mL of water, 0.5 g of G-$CONH_2$ is added and stirred. The temperature is then solwly raised to about 80° C. over a 3.5 hour period and kept there for about 10 min. After cooling, the separated solids are filtered and washed with water. Recrystallization from chloroform-petroleum ether gives the pure product G-NHCONHC(O)-G.

Example 41

G-$N_3$ from G-Br

A mixture of G-Br (2 mmole) and sodium azide (1.3 g) in dry dimethyl sulfoxide (DMF, 20 mL) is heated with stirring at 100° C. for about two days. The mixture is poured onto ice-water to give precipitates which can be purified by recrystallization from aqueous methanol to give the pure product.

Example 42

G-OCOCl from G-OH

To a solution of liquid phosgene ($COCl_2$, 30 g) in anhydrous benzene (100 mL), a solution of G-OH (53 mmoles) and pyridine (7 g) in benzene (200 mL) is added dropwise and with stirring over a 1 hour period, while maintaining the reaction temperature at about 4° C. when solids precipitate, additional benzene is added.

The reaction mixture is filtered and the filtrate is poured into ice water and shaken in a separatory funnel. The organic layer is dried with sodium sulfate and concentrated to about one-fifth of its original volume under reduced pressure at room temperature, and the concentrated solution is stored in a freezer. The yield may be considered essentially quantitative for the purpose of synthetic use of the solution.

When a sample of the concentrate is evaporated to dryness at room temperature, the solid is obtained. Recrystallization from anhydrous petroleum ether at low temperature, e.g. −20° C., may give crystals of the product.

Example 43

G-OCONHNH$_2$ from G-OCOCl and H$_2$NNH$_2$

A solution of G-OCOCl (9.3 mmoles) in anhydrous benzene (150 mL) is added slowly to a stirred solution of anhydrous hydrazine (2.5 g) in t-butyl alcohol (20 mL). After stirring for about 2 hours, the solvent is removed in vacuo. The residue is dissolved in a mixture of ether (150 mL) and water (10 mL). The ether layer is washed with 35 mL portions of water, 5 mL of 1% sodium carbonate solution, and 5 mL of water, and dried. Anhydrous hexane (10 mL) is added and the solution is concentrated to about 10 mL. Cooling the solution at about −10° C. gives the product G-OCONHNH$_2$.

Example 44

Heterodiamondoidyloxycarbonyl Amino Acids from G-OCOCl and Amino Acids

A suitable amino acid (5 mmoles) is suspended in water (about 20 mL). The mixture is stirred and cooled in an ice bath. Sodium hydroxide (1N, 5 mL) is added whereupon the amino acid usually dissolved. To this mixture, 0.8 g sodium carbonate (7.5 mmoles) is added. From a solution of G-OCOCl, the solvent is removed in vacuo on a flash evaporator at a bath temperature of about 30° C. (the concentration of the chloroformate in the benzene solution is determined by removing the solvent from an aliquot in vacuo at about 30° C. and weighting the residue). To the residue which may be oily or semisolid, dry petroleum ether is added and removed in vacuo. This is repeated once more to remove traces of phosgene which may be left in the preparation of the chloroformate. The residue is dissolved in anhydrous dioxane (5 mL) and added in about four portions to the solution of the amino acid over a period of about 1 hour with continued stirring and cooling. If solid precipitates, ether is added (5 mL) after the first and last addition of the chloroformate. After the addition of the chloroformate, the container of the chloroformate is washed twice with a small amount of dioxane. After stirring in ice for about 2 hours, the solution is extracted three times with ether or ethyl acetate, and under stirring and cooling acidified with 85% phosphoric acid or 10% sulfuric acid to a pH of about 2. The precipitated product is extracted into the organic layer and the aqueous phase is extracted with two more portions of fresh organic solvent. The combined extracts are dried over sodium sulfate and the solvent is removed in vacuo. The residue is recrystallized from a suitable solvent, e.g. ether-petroleum ether, ethyl acetate or ethyl acetate-petroleum ether.

Example 45

Figure 21:
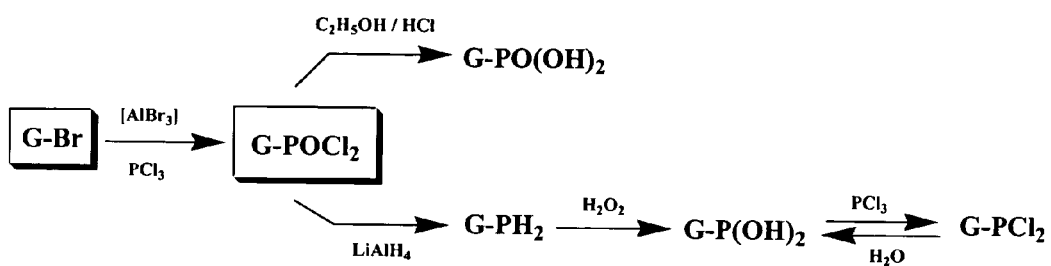

G-POCl$_2$ from G-Br (FIG. 21)

0.1 mole of G-Br, 40 g (0.15 mol) of AlBr$_3$ and 200 mL of PCl$_3$ are heated for about 5 hours under reflux while being stirred. After cooling down and filtration, the residue is washed with 100 mL of benzene, suspended in 300 mL of CCl$_4$ and decomposed carefully with water while cooling with ice. The organic phase is separated out, washed with water, dried over CaCl$_2$ and concentrated in vacuum. Separation and purification of the product G-POCl$_2$ can be conducted by distilling the residue and recrystallization from acetone. Please note that G-POCl$_2$ does not reaction with ethanol in pyridine or piperidine in benzene. Thus, 0.05 mole of G-POCl$_2$ together with 9.2 g (0.2 mole) ethanol and 7.9 g (0.1 mole) pyridine are heated under reflux for about 3 hours. Then the reaction mixture is poured onto ice while adding dilute hydrochloric acid. The product is filtered off and recrystallized from acetone affording the unreacted G-POCl$_2$. In addition, 0.05 mole of G-POCl$_2$ and 17 g (0.2 mole) of piperidine are dissolved in 200 mL absolute benzene, and then heated for about 48 hours under reflux while stirring. After filtration, the filtrate is concentrated to dryness affording the unreacted G-POCl$_2$.

20 mmoles of G-POCl$_2$ is heated for about 6 hours with 100 mL water under reflux. The aqueous solution is filtered after cooling, and the residue is recrystallized from glacial acetic acid affording the product G-PO(OH)$_2$.

Under nitrogen a solution of 0.1 mole of G-POCl$_2$ in 150 mL absolute ether is added dropwise over a period of about 2 hours to a suspension of 7 g LiAlH$_4$ in 400 mL absolute ether. After the addition, the mixture is stirred for an additional 1 hour under reflux. The excess LiAlH4 is destroyed by adding about 200 mL dilute hydrochloric acid. The organic phase is separated out, washed with water, dried over MgSO$_4$ and concentrated under nitrogen. The residue is fractionated under nitrogen in vacuum to give the product G-PH$_2$.

About 50 mmoles of G-PH$_2$ is heated carefully at approximately 50° C. with 50 mL of 30% hydrogen peroxide (H$_2$O$_2$) until the reaction starts. Then the reaction mixture is diluted to one and half with water, boiled briefly and filtered in hot. After cooling down it is possible to isolate some of the product G-P(OH)$_2$. The residue is extracted with CHCl$_3$ and then recrystallized from glacial acetic acid to give some additional amount of the product.

0.05 mole of G-P(OH)$_2$ is added in small portions to 75 mL of PCl$_3$ within 10 minutes. After the addition, the reaction mixture is stirred for an additional 5 minutes. The phosphoric acid produced is separated out and the residue is concentrated under vacuum and distilled to give the product G-PCl$_2$. Purification can be carried out by sublimating several times to give a pure sample for analysis.

0.01 mole of G-PCl$_2$ is stirred in 50 mL water intensively for about 10 hours at room temperature. Then the mixture is filtered and the residue is recrystallized several times from acetonitrile to yield the product G-P(OH)$_2$.

Example 46

Figure 22:
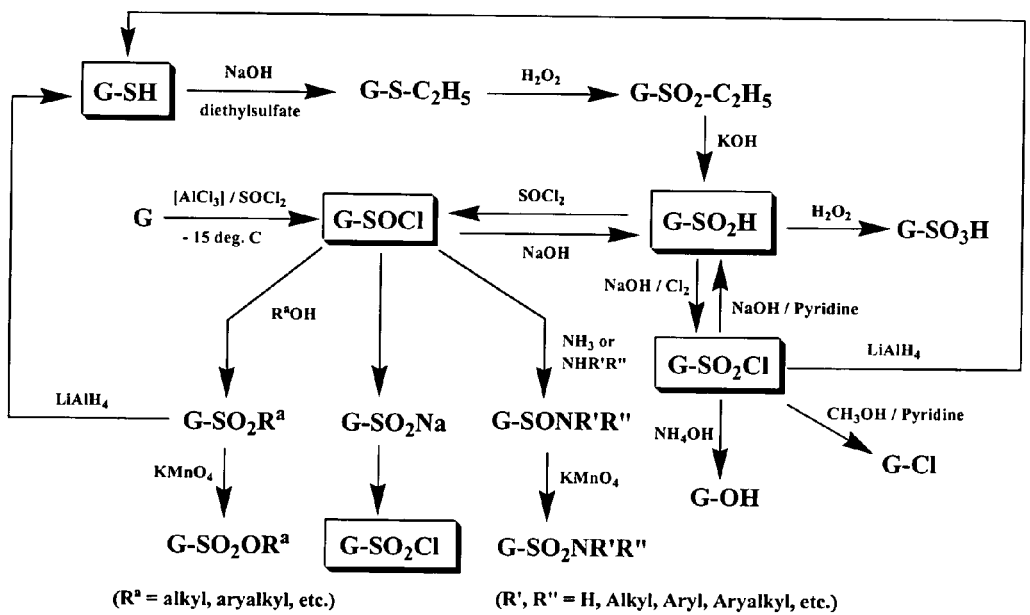
Figure 23:
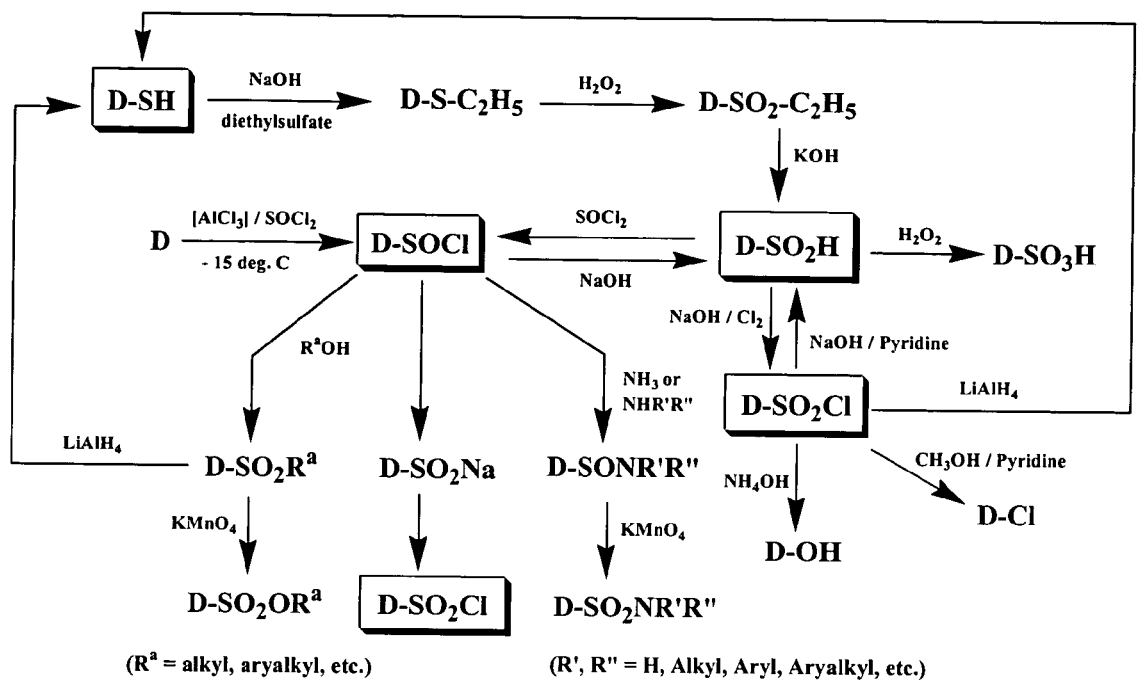
Figure 25:
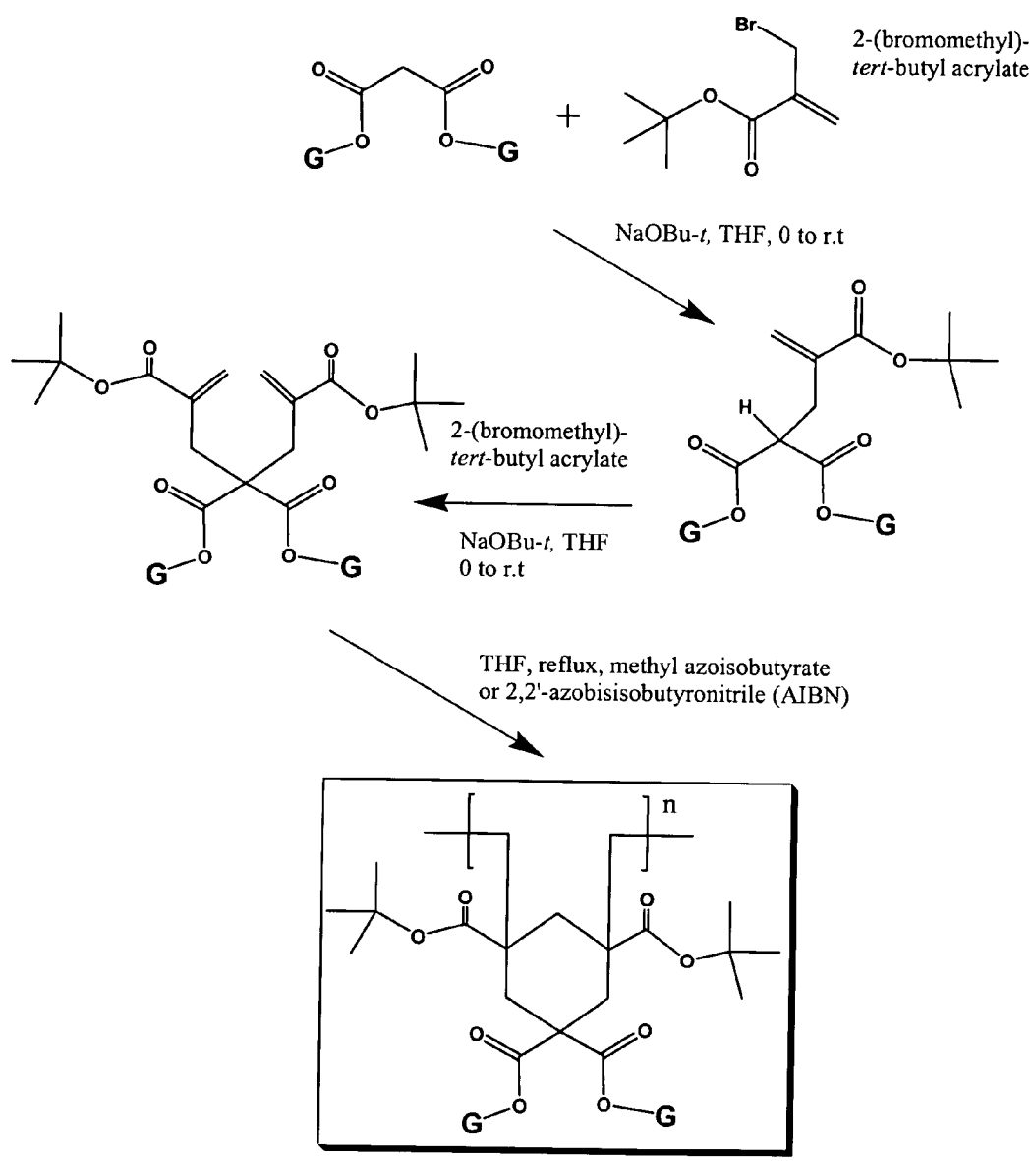

G-SOCl from G and Subsequent Reactions (FIG. 22)

40 g (0.3 mole) of AlCl$_3$ and 200 mL of SOCl$_2$ are reacted at about −15° C. for about 2 hours with 0.3 mole of a heterodiamondoid. The mixture is stirred for an additional 1 hour at this temperature. Then the clear solution is allowed to warm to room temperature, and the excess SOCl$_2$ is removed under vacuum. The residue is taken up in 300 mL of CCl$_4$ and carefully decomposed with water. The organic phase is separated out, washed with water, dried over CaCl$_2$ and concentrated in vacuum. The residue is distilled to give the product G-SOCl. Please note that G-Cl is produced as the major by-product.

0.1 mole of G-SOCl is heated under reflux for about 6 hours with 200 mL of absolute methanol. The solvent is then removed in vacuum and the residue is distilled to give the product. Further purification can be carried out by sublimation under vacuum.

0.1 mole of LiAlH$_4$ is suspended in 100 mL of absolute ether and heated under reflux for about 1 hour. Then a solution of 0.02 mole of G-SO$_2$CH$_3$ in 100 mL of absolute ether is added dropwise over a period of about 2 hours. After about additional 17 hours of stirring under reflux, the excess LiAlH$_4$ is decomposed with a saturated Na$_2$SO$_4$ solution, and the ether phase is separated out after 100 mL of concentrated hydrochloric acid has been added. The aqueous phase is washed for an additional two times with ether. The extracts are combined and dried over CaCl$_2$ and concentrated under vacuum. The residue is sublimated to give G-SH.

To 650 mL 5% sodium hydroxide solution is added about 0.25 mole of G-SOCl (crude product) at room temperature. After about 5 hours of intense stirring, the temperature is increased slowly to about 50° C., then filtration. Approximately 12% chlorination products remain as residue. The filtrate is acidified with concentrated hydrochloric acid while cooling with ice, and extracted several times with ether. The combined extracts are washed with water, dried over MgSO$_4$ and concentrated to a dry product. Recrystallization from acetonitrile gives a pure product G-SO$_2$H.

5 mmoles of G-SO$_2$H is suspended in 25 mL water while adding 1 mL 30% hydrogen peroxide. Then the mixture is heated while stirring on a water bath and an additional 3 mL 30% hydrogen peroxide are added dropwise within 30 minutes. The solution is briefly boiled, filtered and concentrated under vacuum to dryness at about 30° C. to give the heterodiamondoidyl sulfonic acid monohydrate G-SO$_3$H.H$_2$O.

0.1 mole of G-SH dissolved in 100 mL ethanol is added while stirring into a solution of 8 g (0.2 mole) of NaOH in 200 mL water and treated for about 1 hour at 50° C. with 15.4 g (0.1 mole) of diethylsulfate. After an additional 1 hour stirring under reflux, the reaction mixture is cooled down and extracted several times with ether. The combined extracts are concentrated in vacuum and the residue is distilled over CaCl$_2$ to give the product G-SC$_2$H$_5$.

0.05 mole of G-SC$_2$H$_5$ in 100 mL glacial acetic acid is heated to reflux with 17.5 g (0.15 mole) 30% hydrogen peroxide. After about 1 hour of stirring under reflux, the reaction mixture is poured onto ice and filtered. Recrystallization from ethanol/water gives the product G-SO$_2$C$_2$H$_5$.

0.02 mole of G-SO$_2$C$_2$H$_5$ and 12 g KOH are heated to 250° C. with 3–5 drops of water. Then the temperature is raised to 275° C. in the course of about 45 minutes, whereby a strong development of a gas takes place. After cooling down, the mixture is dissolved in a little water, acidified with concentrated hydrochloric acid while cooling with ice and extracted several times with ether. The distillation residue from the ether extract gives, after recrystallization from acetonitrile, a pure product of G-SO$_2$H.

0.05 mole of G-SO$_2$H is left standing over night with 100 mL freshly distilled SOCl$_2$ at room temperature. The excess SOCl$_2$ is carefully removed under vacuum, and the residue is distilled, whereby the product G-SOCl solidifies in the receiver.

0.1 mole of G-SOCl together with 200–300 mL absolute alcohol and 7.9 g (0.1 mole) pyridine is heated for 8–12 h under reflux. The excess alcohol is then removed under vacuum and the residue is mixed with ether. The ether solution is washed twice with dilute hydrochloric acid and water, dried over MgSO$_4$ and concentrated. The residue is distilled to give the corresponding ester.

45 mmoles of G-SOCl is heated with 300 mL 25% aqueous ammonia or 150 mL 40% aqueous dimethylamine for about 2 hours while stirring under reflux. Then the reaction mixture is concentrated to dryness in vacuum and the residue is extracted with ether. The distillation residue from the ether extract is recrystallized from cyclohexane to afford the corresponding amide.

Into a clear solution of 0.05 mole G-SO$_2$H and 2 g (0.05 mole) NaOH in 200 mL water is introduced a strong chlorine gas flow at approximately 5° C. temperature increase within 45 minutes. After filtration, the residue is extracted in ether. The ether solution is washed chlorine-free with NaHSO$_3$ solution, dried over MgSO$_4$ and concentrated to dryness in vacuum at room temperature. Recrystallization from ethanol gives the product G-SO$_2$Cl. Further recrystallization several times from petroleum ether can afford a pure sample for analysis.

0.01 mole G-SO$_2$Cl in 100 mL absolute ether is added dropwise within 1 hour to a suspension of 3 g LiAlH$_4$ in 100 mL absolute ether. After the addition, the reaction mixture is stirred for about 3 hours under reflux, then the excess LiAlH$_4$ is destroyed with dilute hydrochloric acid. The organic phase is separated out, dried over MgSO$_4$ and concentrated. The residue is sublimated several times to give G-SH.

10 mmoles G-SO$_2$Cl and 100 mL 10% sodium hydroxide solution are heated on a water bath for about 4 hours while adding 1 g pyridine. After cooling and filtration, the filtrate is acidified with concentrated hydrochloric acid and perforated over night with ether. The ether extract is dried over MgSO$_4$ and concentrated to yield G-SO$_2$H.

20 mmoles G-SO$_2$Cl together with 30 mL absolute methanol and 3 g pyridine is heated for about 4 hours at 50° C. while stirring vigorously. Then the reaction mixture is poured on ice and extracted with ether. The ether solution is washed with dilute hydrochloric acid, dried over MgSO$_4$ and concentrated. The residue is sublimated to give G-Cl.

10 mmoles G-SO$_2$Cl and 100 mL 25% aqueous ammonia are heated on a water bath for about 3 hours while stirring. The solution is concentrated in vacuum to dryness, and the residue is sublimated to give G-OH.

0.02 mole of the corresponding hetero diamondoidyl sulfinic acid ester or amide is treated in 150–400 mL acetone at reflux with a saturated solution of KMnO$_4$ in acetone until a violet color remains. After an additional 30 minutes of stirring under reflux, the reaction mixture is filtered from MnO$_2$ and the residue is extracted several times with acetone. The combined filtrates are then concentrated in vacuum to give the corresponding hetero diamondoidyl sulfonic acid esters or amides.

Example 47

G-G from G-Br

A monobrominated heterodiamondoid G-Br (50 mmole) is dissolved in 30 mL of xylene and heated to reflux in a three-necked flask fitted with thermometer, nitrogen inlet, stirrer, and reflux condenser, under a slow stream of nitrogen. Then a total of 1.15 g of small pieces of sodium metal is added to the stirred reaction mixture over a period of about 4 hours. After all sodium has been added, the mixture is refluxed for about an additional hour and then filtered in the hot state. On cooling to room temperature, the product G-G is crystallized from the filtrate. This G-G product can itself be di brominated and thereafter converted to dicyano, decarboxyl diamino and diacetamido derivatives as desired.

Example 48

CH$_3$OC$_6$H$_4$-G-G-C$_6$H$_4$OCH$_3$ from Br-G-G-Br

To Br-G-G-Br (11.5 mmole) is added 25 mL of anisole and the mixture is heated to reflux (about 155° C. pot temperature) for about 5 hours. After about 15 minutes refluxing, hydrogen bromide is evolved. The evolution of hydrogen bromide is ceased after about 1 hour. The reaction product is filtered hot and on cooling to room temperature, a crude product is collected which is then recrystallized from xylene to give the pure product CH$_3$OC$_6$H$_4$-G-G-C$_6$H$_4$OCH$_3$.

Example 49

HClH$_2$NCH$_2$-G-G-CH$_2$NH$_2$HCl and H$_2$NCH$_2$-G-G-CH$_2$NH$_2$ from NC-G-G-CN Powdered lithium aluminum hydride (0.6 g) is charged into a three-neck flask fitted with a thermometer, nitrogen inlet, addition funnel, and reflux condenser together with 15 mL of anhydrous THF. A solution of NC-G-G-CN (7.8 mmole) in 20 mL of anhydrous THF is added over a period of about 20 min. the reaction product, after cooling to room temperature, is poured onto ice containing dilute hydrochloric acid. Recrystallization from dilute hydrochloric acid gives the dihydrochloride product HClH$_2$NCH$_2$-G-G-CH$_2$NH$_2$HCl. The free diamine H$_2$NCH$_2$-G-G-CH$_2$NH$_2$ is obtained from the dihydrochloride by reaction with ammonia.

Design of Heterodiamondoid-Containing Polymers or Co-Polymers

Polymers such as polyamides, polyimides, polyesters, polycarbonates which are easily processed soluble, mechanically strong and thermally stable are very important materials in a wide range of industries, such as the microelectronics industry. Introduction of different pendant groups such as heterodiamondoid groups along the polymer backbone can impart greater solubility and enhanced rigidity as well as better mechanical and thermal properties of the resulting polymers. Of particular interest is introducing such heteroatom-containing cage hydrocarbons into the polymer chain because such cardo groups show significant characteristics such as high cardo/hydrogen ratio, high thermal and oxidative stability, rigidity, hydrophobicity, and transparency. They also can impart desired electrical and optical properties to the polymers.

Example 50

Polymerization of Diacrylated Heterdiamondoids

The following compositions are subjected to polymerization: diacrylated heterodiamondoid; monoacrylated heterodiamondoid; a 50:50 mixture by weight of monoacrylated heterodiamondoids and methyl methacrylate; and, a 50:50 mixture by weight of monoacrylated heterodiamondoid and diethylene glycol bis allylcarbonate. To the various compositions is added 0.1 part by weight of a photopolymerization initiator (benzophenone). The mixture is applied to a glass plate and photo-polymerized by irradiation with ultraviolet light.

Example 51

Polymerization of Diethynylated Heterodiamondoids

A sample of a diethynylated heterodiamondoid (275 mg) is sealed in a glass tube and heated to 200° C. for 14 hours and at 250° C. for 48 hours. The tube is cooled to room temperature and opened to afford a polymeric resin.

Example 52

Polyesters Derived from 2,2-Bis(4-hydroxyphenyl) Heterodiamondoids by Solution Polycondensation A 2,2-bis(4-hydroxyphenyl) heterodiamondoid (0.005 mole) is mixed with pyridine (2 mL) at room temperature for about 20 minutes. Terephthaloyl chloride (1.015 g, 0.005 mole) in nitrobenzene (20 mL) is added to the above solution at room temperature for about 5 minutes and then the mixture is heated to about 150° C. for about 10 hours. The resulting polymer solution is poured into methanol to precipitate the polymer. The polymer is washed with hot methanol, collected on a filter, and dried in vacuo at about 60° C. for about 24 hours.

Example 53

Polyamides Derived from 2,2-Bis[4-(4-aminophenoxy)phenyl]Heterodiamondoids by Solution Polycondensation A flask is charged with a mixture of a 2,2-bis[4-(4-aminophenoxy)phenyl] heterodiamondoid (0.9 mmol), terephthalic acid (0.149 g, 0.9 mmol), triphenyl phosphite (0.7 mL), pyridine (0.6 mL), N-methyl-2-pyrrolidone (NMP, 2 mL) and calcium chloride (0.25 g). It is refluxed under argon for about 3 hours. After cooling, the reaction mixture is poured into a large amount of methanol with constant stirring, producing a precipitate that is washed thoroughly with methanol and hot water, collected on a filter, and dried to afford a polyamide containing heterodiamondoid components along the polymer chain.

Example 54

Polyimides Derived from 2,2-Bis[4-(4-aminophenoxy)phenyl] Heterodiamondoids by Chemical Imidization To a stirred solution of a 2,2-bis[4-(4-aminophenoxy) phenyl] heterodiamondoid (1.2 mmol) in DMAc (7 mL) is gradually added pyromellitic dianhydride (0.262 g, 1.2 mmol). The mixture is stirred at room temperature for 2–4 hours under argon atmosphere to form the poly(amic acid). Imidization is carried out by adding DMAc and an equimolar mixture of acetic anhydride and pyridine into the abovementioned poly(amic acid) solution with stirring at room temperature for about 1 hour and then heating at about 100° C. for an additional about 3 hours. The reaction product is subsequently poured into methanol and the precipitate is filtered off, washed with methanol and hot water, and dried to afford the polyimide containing heterodiamondoid components along the polymer chain.

Example 55

Polyimides Derived from 2,2-Bis(4-aminophenyl) Heterodiamondoids by Chemical Imidization

To a solution of a 2,2-bis(4-aminophenyl) heterodiamondoid (5 mmol) in 17.9 mL of NMP, 3,3',4,4'-benzophenonetetracarboxylic dianhydride (BTDA, 98.6%, 1.61 g, 5 mmol) is added with a solid content of 15 wt %. The solution is continuously stirred at room temperature for about 24 hours. To the reaction mixture are added 1.5 mL of acetic anhydride and 2.0 mL of pyridine and then the temperature is raised to about 120° C. and kept at this temperature for about 3 hours. The resulting solution is poured into excess methanol and filtered. The precipitated polymer is washed several times with water and methanol, and then the polymer is dried at about 100° C. for around 12 hours in vacuo.

Example 56

Polyimides Derived from 2,2-Bis(4-aminophenyl) Heterodiamondoids by Solution Polymerization

To a solution of a 2,2-bis(4-aminophenyl) heterodiamondoid (5 mmol) in 19 mL of freshly distilled m-cresol, 3,3',4,4'-benzophenonetetracarboxylic dianhydride (98.6%, 1.61 g, 5 mmol) and isoquinoline (0.95 mL) as a catalyst are added at room temperature under nitrogen atmosphere. The reaction mixture is heated to about 70–80° C. over 2 hours and kept at this temperature for about 2 hours. Afterwards, the solution temperature is slowly raised to about 200° C. over 2 hours and refluxed for 6 hours. The polymerization is performed under a gentle nitrogen stream to remove the water produced during imidization. Work-up is done by pouring the resulting solution into excess methanol and filtering. The precipitated polymer is washed several times with water and methanol, and then the polymer is dried at about 100° C. for around 12 hours in vacuo.

Example 57

Linear Polyaspartimides Derived from 2,2-Bis[4-(4-aminophenoxy)phenyl] Heterodiamondoids by the Michael Addition Reaction

In a 100 mL three necked flask equipped with a magnetic stirrer, a reflux condenser, thermometer and nitrogen inlet, 0.553 g (1.25 mmol) of bis(3-ethyl-5-methyl-4-maleimidophenyl)methane (BEMM) is added to 3.5 mL of m-cresol. When all the BEMM is dissolved, 1.25 mmol of a diamine 2,2-bis[4-(4-aminophenoxy)phenyl] heterodiamondoid is added. Then 0.1 mL of glacial acetic acid, used as a catalyst, is added into the mixture so that the above diamine is completely dissolved. The reaction mixture is then immersed in an oil bath maintained at 100–110° C. for about 100 hours to polymerize. The resulting polymer is isolated by pouring the viscous reaction mixture into excess ethanol under vigorous stirring. The polymer precipitate is collected by filtration and washed thoroughly with ethanol and extracted with hot ethanol using a Soxhlet extractor and subsequently dried in a vacuum oven at 70° C. for about 24 hours.

Example 58

4-(1-Heterodiamondoidyl)-1,3-Benzenediols from Brominated Compounds and Subsequent Reactions

A suitable brominated heterodiamondoid (0.046 mole), resorcinol (5.51 g, 0.05 mole), and benzene (50 mL) are combined in a reaction flask equipped with a nitrogen inlet, a condenser fitted with a caustic scrubber, and a stirrer. This mixture is heated to reflux and for about 72 hours to allow for reaction under a constant nitrogen purge to assist in the removal of HBr formed. The reaction mixture is cooled to ambient temperature and the hetero diamondoidyl substituted resorcinol is crystallized from solution. Residual resorcinol is removed by precipitating a solution of the product in methanol into warm water followed by filtrating and washing with water. Subsequent purification to a polymerization quality monomer is accomplished by vacuum drying to remove residual water, recrystallizing from toluene, and finally subliming to afford the product which is used in the following reactions.

A mixture of a 4-(1-heterodiamondoidyl)-1,3-benzenediol (13 mmol), p-chloronitrobenzene (4.53 g, 28.8 mmol), potassium carbonate (4.3 g, 31.2 mmol) and dry N,N-dimethylformamide (DMF, 30 mL) is refluxed for about 8 hours. The mixture is then cooled and poured into a methanol-water solution (1:1 by volume). The crude product is recrystallized from glacial acetic acid.

Hydrazine monohydrade (10 mL) is added dropwise to a mixture of the above product (4-(1-heterodiamondoidyl)-1,3-bis(4-nitrophenoxy)benzene, 12.3 mmol), ethanol (25 mL), and a catalytic amount of 10% palladium on activated carbon (Pd/C, 0.05 g) at the boiling temperature. The reaction mixture is refluxed for about 24 hours, and the diamine product is precipitated during this period. The mixture is then added to a sufficient amount of ethanol to dissolve the diamine product and filtered to remove Pd/C. After cooling, the recipitated crystals are isolated by filtration and recrystallized from 1,2-dichlorobenzene to afford a pure diamine product.

A flask is charged with 1.73 mmol of a 4-(1-heterodiamondoidyl)-1,3-bis(4-aminophenoxy)benzene, 0.68 g (3.54 mmol) of trimellitic anhydride, and 5 mL of DMAc. The mixture is stirred at room temperature for about 5 hours under argon atmosphere. While continuing to maintain agitation and room temperature, 2.4 mL of acetic anhydride and 1.5 mL of pyridine are added incorporating for about 1 hour. Afterwards the mixture is heated at 100° C. for about 4 hours and then cooled and poured into methanol. The precipitate is filtered off and is purified by extraction with hot ethanol using a Soxhlet extractor and subsequently dried in a vacuum oven at 70° C. for 24 hours to afford diimide-dicarboxylic acid: 4-(1-hetero diamondoidyl)-1,3-bis(4-trimellitimidophenoxy)benzene.

A mixture of the diimide-dicarboxylic acid (4-(1-heterodiamondoidyl)-1,3-bis(4-trimellitimidophenoxy)benzene, 0.7 mmol), 0.362 g of a diamine (2,2-bis[4-(4-aminophenoxy)phenyl]hexafluoropropane, 0.7 mmol), 0.25 g of calcium chloride, 0.6 mL of triphenyl phosphite, 0.6 mL of pyridine, and 3.0 mL of NMP is heated with stirring at 100° C. for about 2 hours under argon stream. After cooling, the reaction mixture is poured into a large amount of methanol with constant stirring, producing a precipitate that is washed thoroughly with hot water and methanol, collected on a filter, and dried at 100° C. under vacuum for 24 hours to afford a pure polyamide-imide containing heterodiamondoid components in the polymer backbone.

A 4-(1-heterodiamondoidyl)-1,3-benzenediol (20.5 mmol) and 4,4'-difluorobenzophenone (4.468 g, 20.5 mmol) mixture is dissolved in 35 mL DMAc and 10 mL toluene in a reaction flask fitted with a nitrogen blanket, mechanical stirrer, and a Dean-Stark trap. To this mixture $K_2CO_3$ (2.969 g, 21.48 mmol) is added while stirring and heating to reflux. Reflux is held at around 130° C. for about 1 hour followed by the gradual removal of toluene from the reaction flask until the flask temperature reaches around 160° C. (ca. 2 hours). The reaction mixture is maintained at 160° C. for 10 hours and then cooled to ambient temperature. The polymer solution is diluted with chloroform, filtered to remove the inorganic salts, acidified, and then precipitated into methanol. Filtration and drying of the product at about 120° C. under vacuum gives the homopolymer.

Example 59

Co-Polymerization from 4-(1-Heterodiamondoidyl)-1,3-Benzenediols and 2,2-Bis(4-Hydroxyphenyl) propane by Nucleophilic Aromatic Substitution Co-polymerizations are carried out with different molar ratios of co-monomers (2,2-bis(4-hydroxyphenyl)propane and a 4-(1-heterodiamondoidyl)-1,3-benzenediol) using either DMAc or tetramethylene sulfone (sulfolane) as solvent. For instance, a 4-(1-hetero diamondoidyl)-1,3-benzenediol (10.25 mmol) and 2,2-bis(4-hydroxyphenyl)propane (10.25 mmol) and 4,4'-difluorobenzophenone (4.468 g, 20.5 mmol) can be dissolved in 35 mL DMAc and 10 mL toluene in a reaction flask fitted with a nitrogen blanket, mechanical stirrer, and a Dean-Stark trap. To this mixture $K_2CO_3$ (2.969 g, 21.48 mmol) is added while stirring and heating to reflux. Reflux is held at around 130° C. for about 1 hour followed by the gradual removal of toluene from the reaction flask until the flask temperature reaches around 160° C. (ca. 2 hours). The reaction mixture is maintained at 160° C. for 10 hours and then cooled to ambient temperature. The polymer solution is diluted with chloroform, filtered to remove the inorganic salts, acidified, and then precipitated into methanol. Filtration and drying of the product at about 120° C. under vacuum gives the copolymer. If sulfolane is used as the solvent, the co-polymers are Soxhlet extracted with methanol to remove solvent and salts from the insoluble polymer.

Example 60

Poly(3-benzyloxypropyl malate-co-ethyl heterodiamondoidyl malate (85/15) from 3-Benzyloxypropylmalolactonate and Ethyl Heterodiamondoidyl Malolactonate by Anionic Ring-Opening Co-Polymerization A flask is charged with a mixture of 3-benzyloxypropylmalolactonate (85 mol %), ethyl heterodiamondoidyl malolactonate (15 mol %) and tetraethylammonium benzoate ($10^{-3}$ eq. per mole of total moles of the co-monomers, acting as an initiator of the anionic ring-opening co-polymerization) under nitrogen. The mixture is then well stirred and warmed to 37° C. under nitrogen atmosphere and is maintained at this temperature for 15 days. After completion of the co-polymerization reaction, the co-polymers are collected and washed with small amount of water, ethanol, and dried in vacuum for about 24 hours.

Example 61

Phenyl Heterodiamondoid-Modified PEGs [Poly(ethylene glycol)s] from Alcoholate of Heterodiamondoidylphenol To a stirred solution of a poly(ethylene gylcol) (PEG, 1 mmol) in 15 mL dichloromethane, 1 mL of triethylamine is added. This solution is cooled in an ice bath under nitrogen atmosphere. Then 1 g of 4-toluenesulfonylchloride (5.2 mmol) is added. The reaction is continued at 0° C. for 2 hours and then the mixture stirred at room temperature overnight. The product is precipitated in diethyl ether. An additional recrystallization from ethanol is performed in order to remove the triethylammonium chloride formed during the reaction affording a pure PEG tosylate.

Under a nitrogen atmosphere, a heterodiamondylphenol (4 mmol) dissolved in 70 mL of freshly distilled dichloromethane is added dropwise to 0.24 g of sodium hydride suspended in 30 mL of distilled dichloromethane. The solution is stirred for 2 hours at room temperature before adding dropwise the PEG tosylate (a little excess) dissolved in 50 mL of dichloromethane. The reaction mixture is kept at 40° C. for 24 hours. The obtained polymer is precipitated in ethyl ether, recrystallized from ethanol and stored at 4° C.

Example 62

Figure 28:
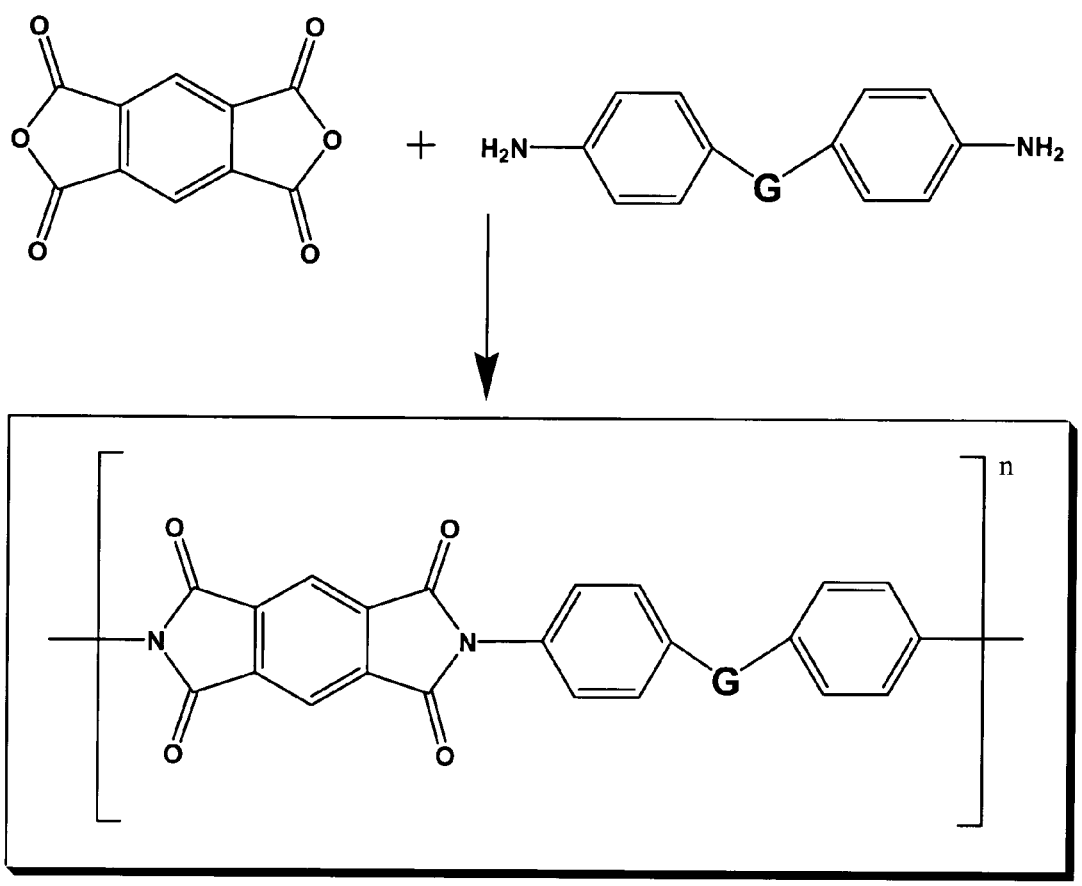

Water Soluble Poly(ethylene glycol)s (PEGs) Containing Heterodiamondoids for Potential Drug Delivery Purposes Host-guest interactions are very important processes in human biology. The water solubility of drugs is a key factor in determining their medical efficacy in living tissue. In order to enhance drug efficiency, poly(ethylene glycol)s (PEGs) can be modified by heterodiamondoid hydrocarbon compounds at their OH terminal ending(s). These hydrophobic groups may be selected based upon their potentially strong interactions with other groups in "cavities" formed in PEG polymer chains and thus can help deliver the drugs which have low solubility in water. Examples are shown in FIG. 28.

Example 63

Carbon-Rich Polymers for Nanolithography

Rapid advances in the miniaturization of microelectronic devices require the development of new imageable polymeric materials for 193 nm microlithography (The *National Technology Roadmap for Semiconductors, Semiconductor Industry Association* (*SIA*), San Jose, Calif., 1997). The design challenge for 193 nm resist materials is the trade-off between plasma-etch resistance (which requires a high carbon/hydrogen ratio in the polymer structure) and optical properties for lithographic performance.

Figure 29:
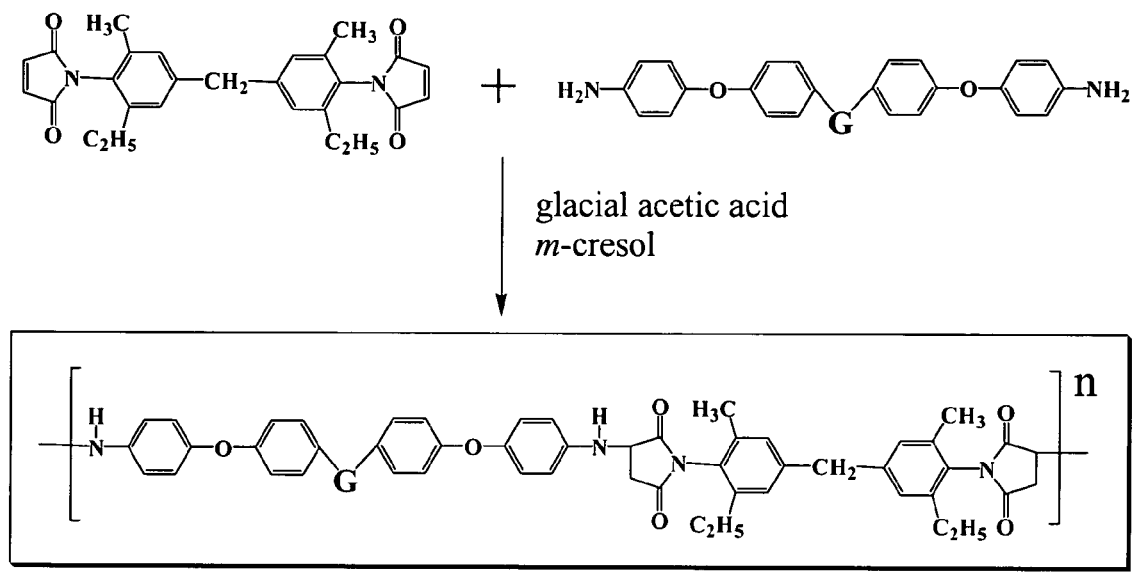
Figure 31:
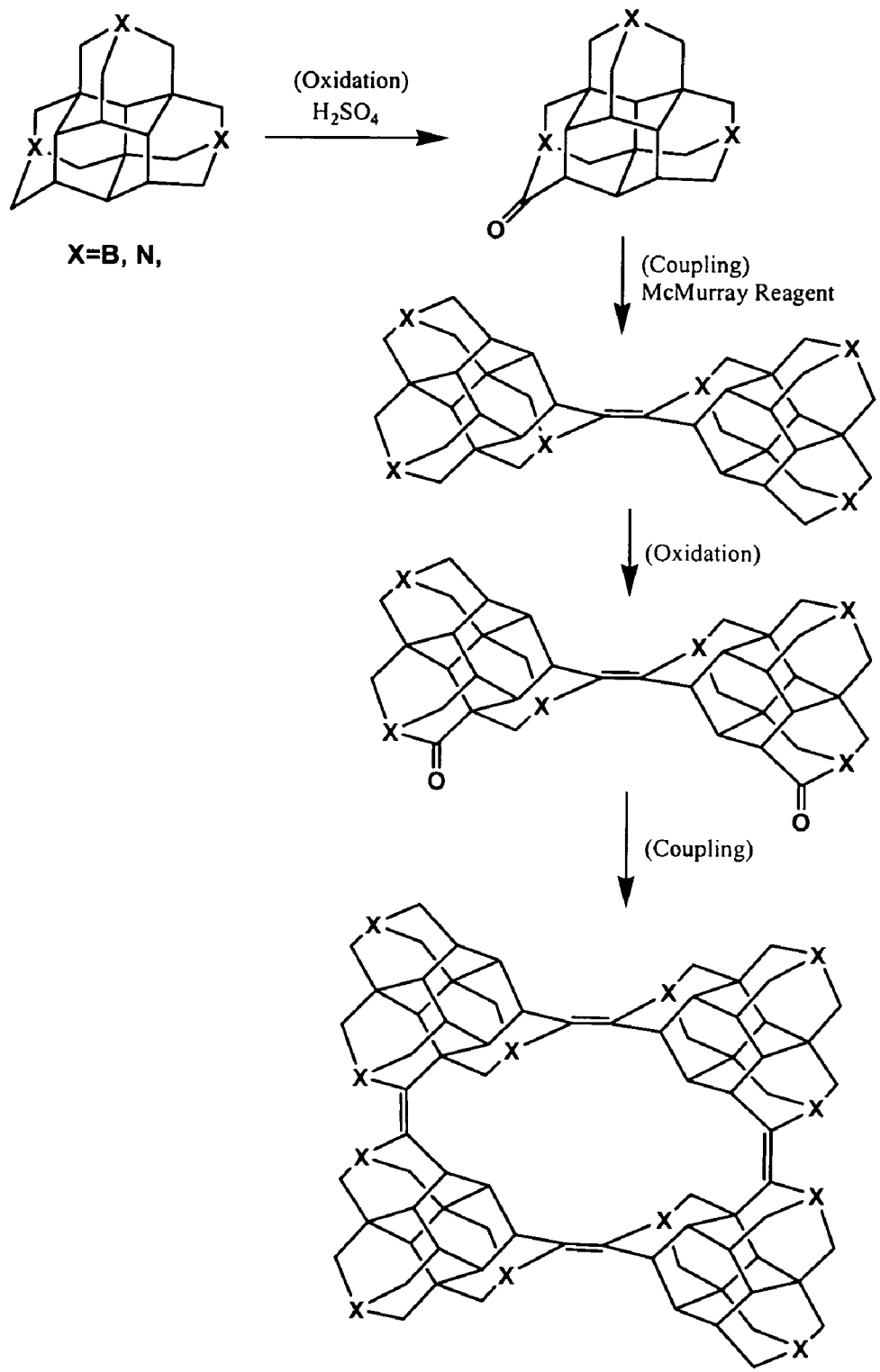
Figure 32:
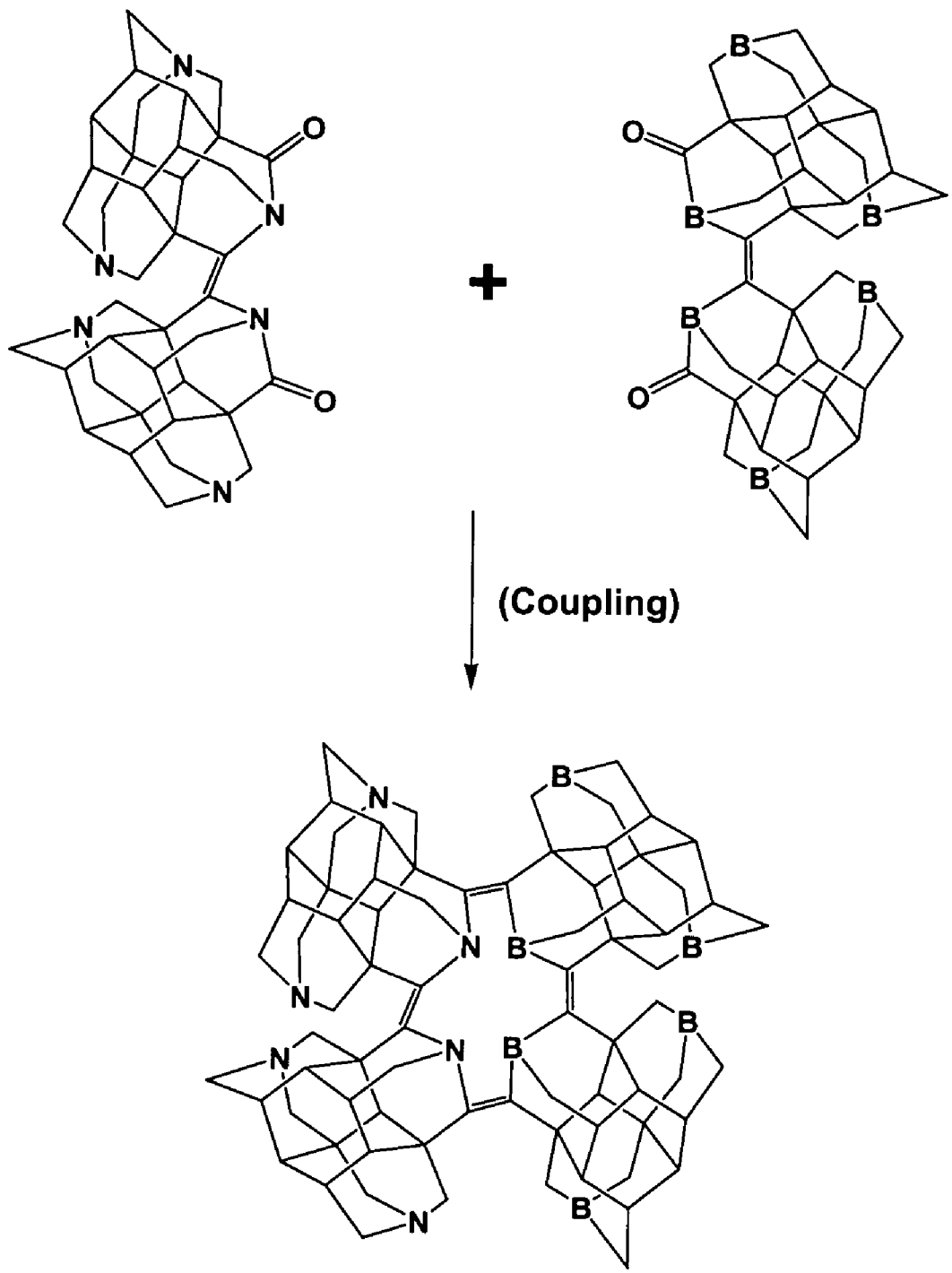
Figure 33:
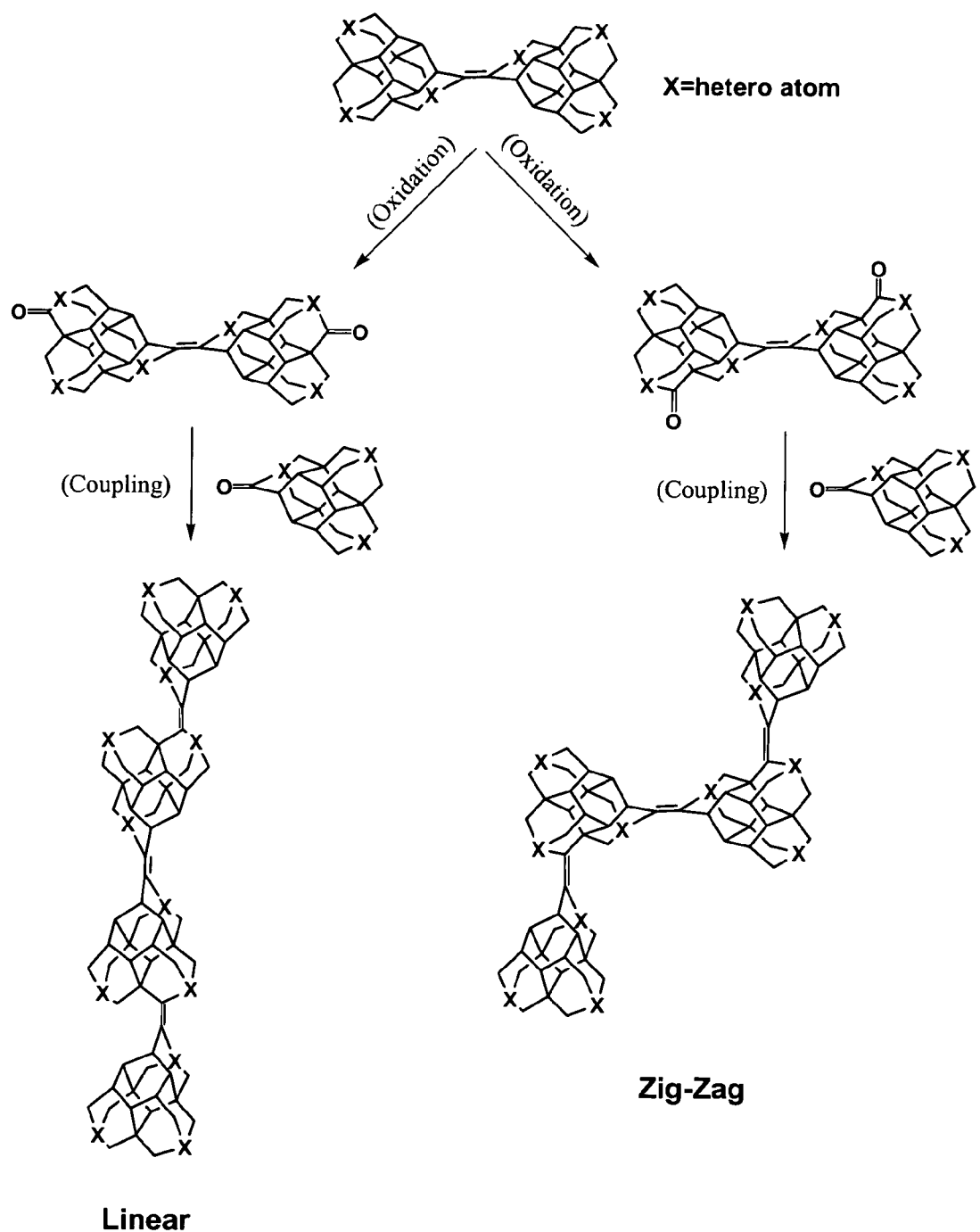
Figure 34:
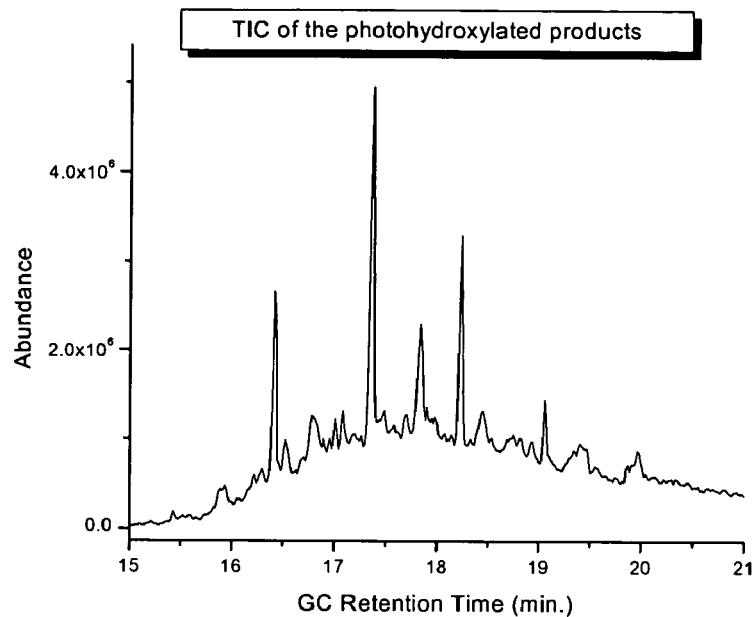
FIG. 34 shows the total ion chromatogram (TIC) of the photohydroxylated mixture of Example 2 containing hydroxylated tetramantanes including hydroxylated alkyl tetramantanes.
Figure 35:
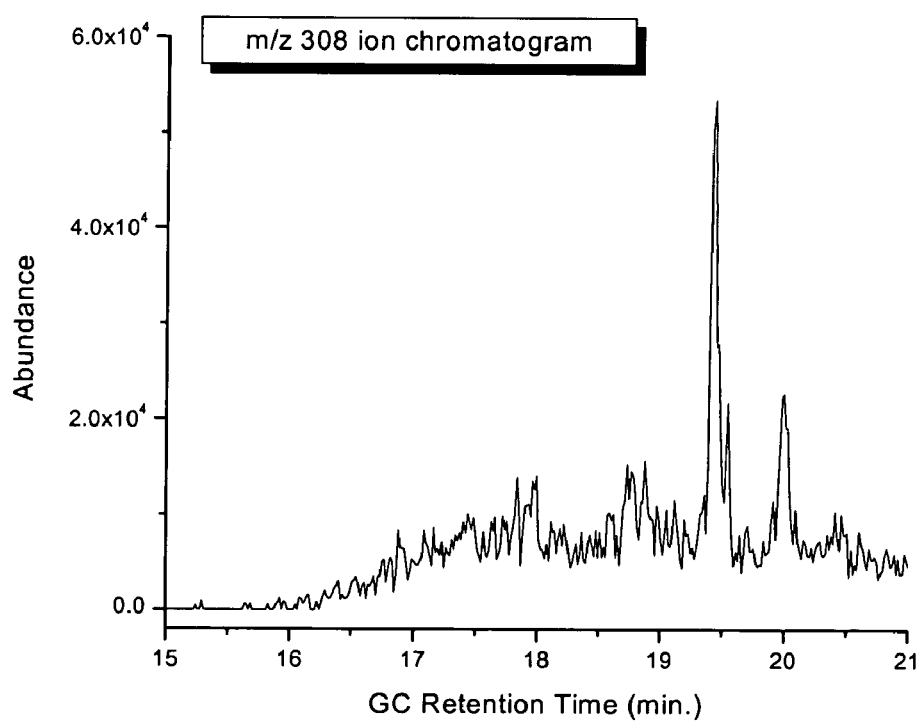
FIG. 35 is the m/z 308 ion chromatogram showing the presence of monohydroxylated tetramantanes in the TIC of the reaction mixture of Example 2.
Figure 36:
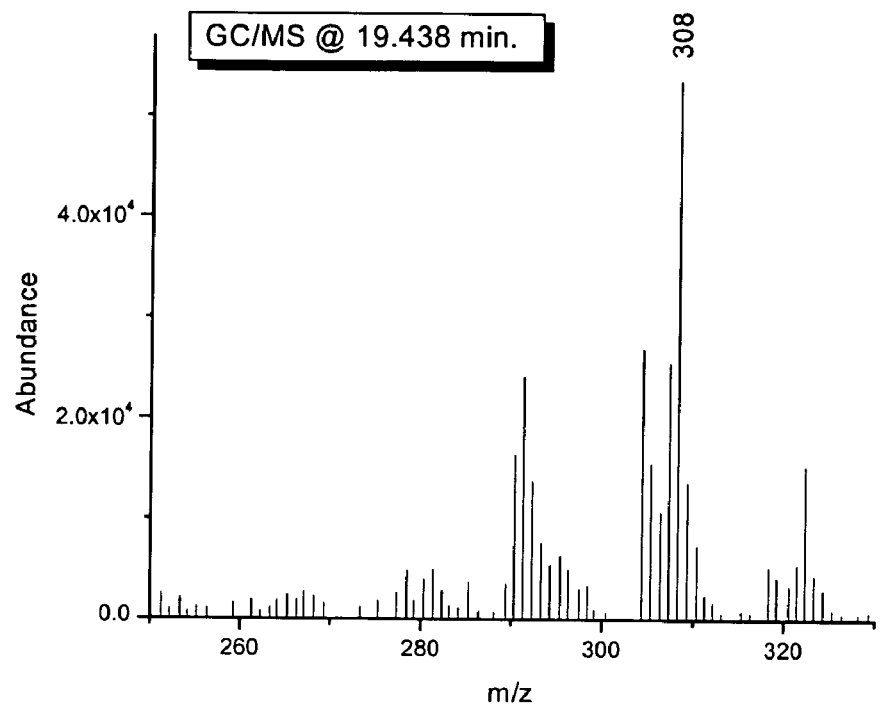
FIG. 36 is the mass spectrum of a monohydroxylated tetramantane with GC/MS retention time of 19.438 minutes from FIG. 35. The base peak in this spectrum is the m/z 308 molecular ion.
Figure 37:
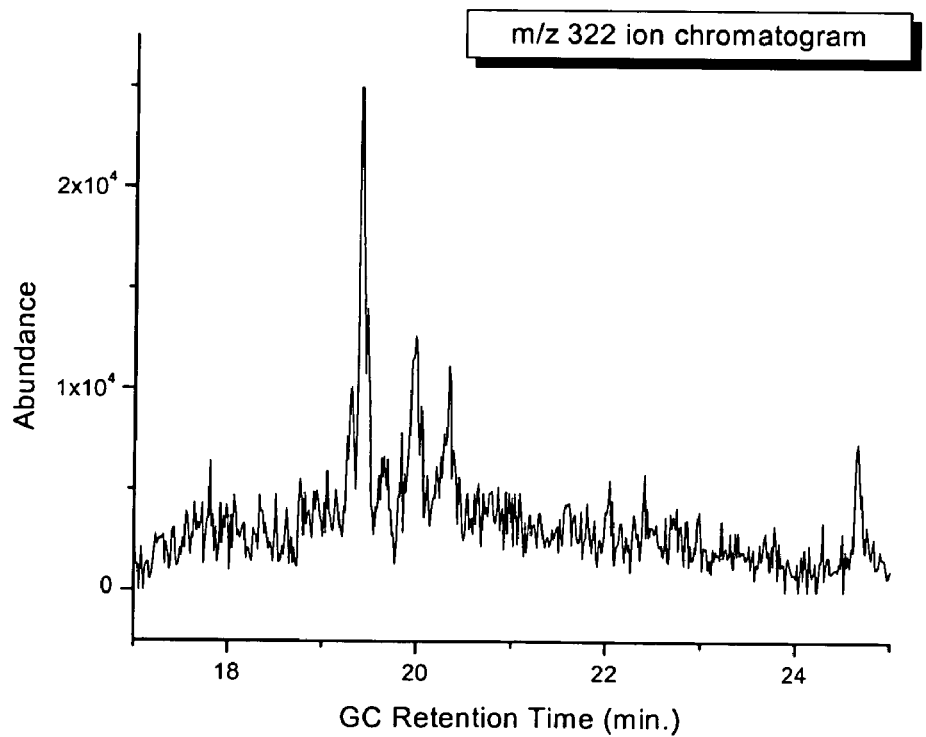
FIG. 37 is the m/z 322 ion chromatogram showing the presence of monohydroxylated methyltetramantanes in the TIC of the reaction product of Example 2.
Figure 38:
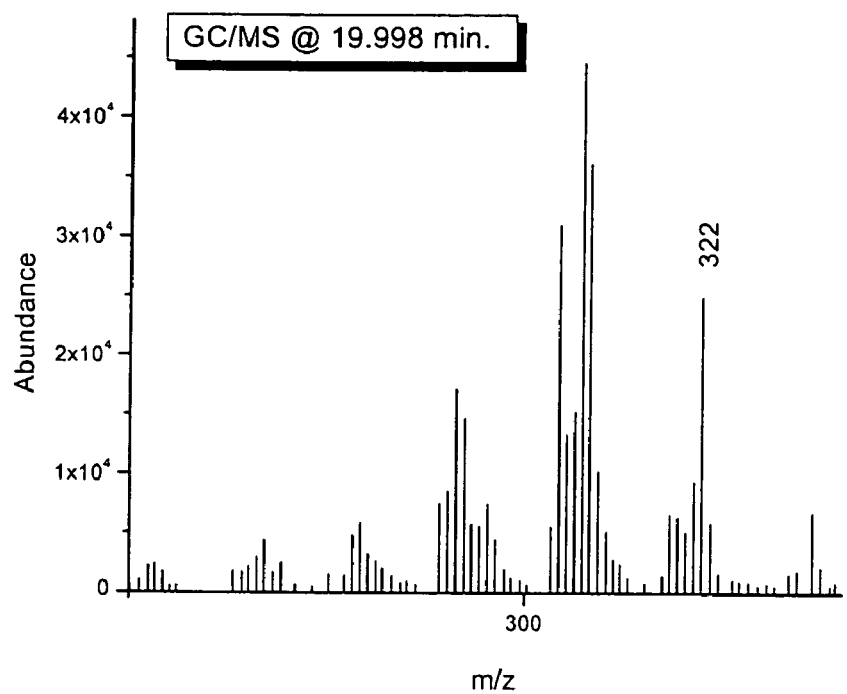
FIG. 38 is the mass spectrum of monohydroxylated methyltetramantane from FIG. 37 with GC/MS retention times of 19.998 minutes.

FIG. 29 shows the design of a carbon-rich cyclopolymer incorporating both imageable functionalities (tert-butyl esters) for chemical amplification, and high etch-resistance moieties (heterodiamondoids based on tetramantanes, pentamantanes, hexamantanes and the like). To adjust the physical properties of polymers, such as wettability and adhesion properties, a wide range of co-polymers can be prepared. This was shown to be feasible for adamantane-containing cyclopolymers and co-polymers by D. Pasini, E Low and J. M. J. Fréchet (*Advanced Materials*, 12, 347–351 (2000)), and those materials showed excellent imaging properties. In addition, since the synthetic routes involve free radical polymerization techniques, metal contamination of the underlying semiconductor substrates is not an issue, as is the case for polymers based on norbornene (*Chemical of Materials*, 10, 3319 (1998); 10, 3328 (1998)). Furthermore, adamantane-containing polymers show high glass transition temperatures ($T_g$) and high deposition temperature ($T_d$) and good film-forming properties. Polymers based on heterodiamondoids would be expected to have even better properties.

Example 64

Figure 26:
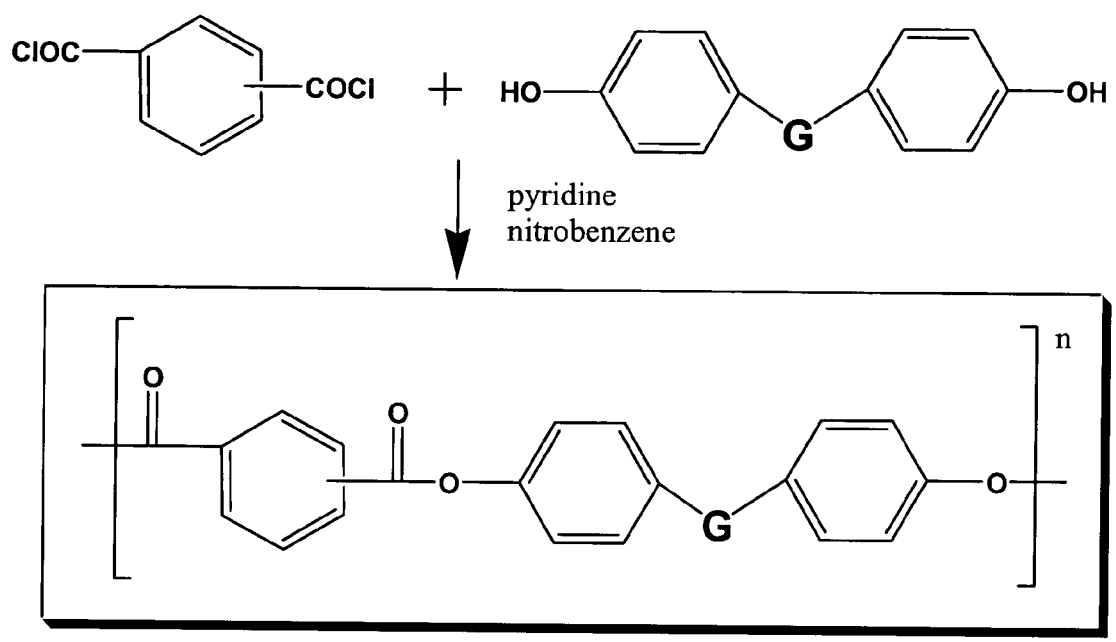

Soluble Heterodiamondoid-Containing Polyesters Based on Heterodiamondoid Bisphenol Polyarylates derived from bisphenol and iso/terephthalic acid are well accepted as highly thermally stable materials. However, polyarylates are generally difficult to process because of their limited solubility in organic solvents and their high melting temperatures or high $T_g$'s by virtue of their rigid structures. It has been reported that incorporation of bulky pendant cardo groups, such as adamantyl groups, into polymer backbones, results in enhanced thermal properties of the polymers compared with polymers containing aromatic bisphenols. As an example of this type of polymer, FIG. 26 shows the design of such polyesters.

Example 65

Soluble Heterodiamondoid Containing Polyamides Based on Heterodiamondoid Diamines Aromatic polyamides attract much interest because of their high-temperature resistance and mechanical strength. However, the applications of polyamides are limited by processing difficulties arising from their low solubility in organic solvents and their high glass transition or melting temperature. A number of successful approaches to increasing the solubility and processability of polyamides, without sacrificing their thermal stability, employ the introduction of flexible or non-symmetrical linkages into the polymer backbone or the incorporation of bulky substituents, such as pendant groups, into the polymer backbone. The inter-chain interaction of the polymers can be decreased by the introduction of bulky pendant groups, resulting in improved solubility of the polymers. Generally, the incorporation of pendant groups results in amorphous materials with increased solubility in common organic solvents.

Figure 27:
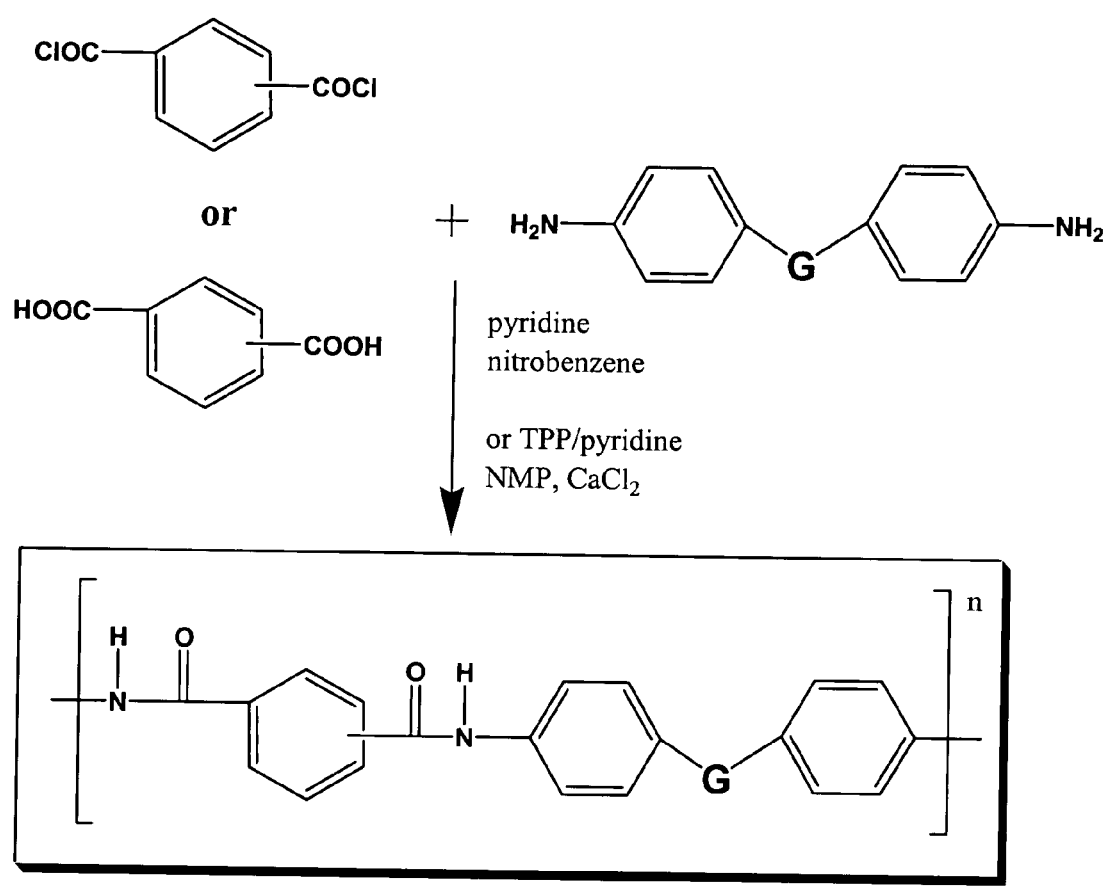

FIG. 27 presents an example of this design which incorporates heterodiamondoid groups in the polyamide backbone.

Example 66

Soluble Heterodiamondoid-Containing Polyimides Based on Heterodiamondoid Diamines The outstanding properties of aromatic polyimides, such as excellent thermo-oxidative stability and superior chemical resistance, led to the use of polyimides in many applications such as insulating materials for electronics, semipermeable membranes for gas separations, and high-temperature adhesives and coatings (J. M. Sonnett, T. P. Gannett, *Polyimides: Fundamental and Applications*, M. K. Ghosh and K. L. Mittal, Ed., Marcel Dekker, New York, 1996). However, in general, aromatic polyimides are insoluble and intractable and are, only processable under extreme conditions. To overcome these processing problems, heterodiamondoid groups can be placed in polyimide polymer backbone (FIG. 28), and in polyaspartimides (FIG. 29).

Example 67

Soluble Heterodiamondoid Containing Polyamide-imides Based on Heterodiamondoid Diamide-Dicarboxylic Acids and Diamines Aromatic polyimides are recognized as a class of high performance materials because of their remarkable thermal and oxidative stabilities and their excellent electrical and mechanical properties, even during long periods of operation. Unfortunately, strong interactions between polyimide chains and their rigid structure make them intractable. Poor thermoplastic fluidity and solubility are the major problems for wide applications of polyimides. On the other hand, polyamides have the advantage of good solubility and processability, as do polyetherimides. Therefore, polyamide-imide or polyetherimide might be the most useful materials, combining the advantages of both polyimides (such as high-temperature stability) and polyamides (such as good processability). In combination with the advantages of diamondoid hydrocarbons, we present a sample design of a polyamide-imide containing heterodiamondoid groups in the polymer chain (FIG. 30). The diamines involved in the polymerization reaction could be either heterodiamondoid diamines such as shown in FIG. 29 or other aromatic diamines.

What is claimed is:

1. A heterodiamondoid compound of the following Formula I:

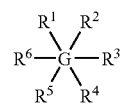

I wherein:
G is a diamondoid nucleus selected from a triamantane or higher diamondoid nucleus having at least one of its carbon atoms replaced by a heteroatom selected from the group consisting of nitrogen, phosphorus, selenium, aluminum, and arsenic; and
$R^1$, $R^2$, $R^3$, $R^4$, $R^5$, and $R^6$ are each independently hydrogen or a covalently bonded functional group, provided that the covalently bonded functional group does not comprise a heteroaryl or heterocycle moiety.

2. The heterodiamondoid compound of claim 1 wherein at least one secondary carbon in the diamondoid nucleus is replaced by a heteroatom.

3. The heterodiamondoid compound of claim 1 wherein at least one tertiary carbon in the diamondoid nucleus is replaced by a heteroatom.

4. The heterodiamondoid compound of claim 1 comprising one heteroatom.

5. The heterodiamondoid compound of claim 1 comprising more than one heteroatoms.

6. The heterodiamondoid compound of claim 1 having from two to twenty different heteroatoms.

7. The heterodiamondoid compound of claim 1 wherein the diamondoid nucleus is a triamantane nucleus.

8. The heterodiamondoid compound of claim 1 wherein the diamondoid nucleus is a higher diamondoid nucleus.

9. The heterodiamondoid compound of claim 1 wherein at least one of the heteroatoms replacing a carbon atom is an electron-donating heteroatom.

10. The heterodiamondoid compound of claim 9, wherein the electron-donating heteroatom is selected from the group consisting of nitrogen, phosphorus, and arsenic.

11. The heterodiamondoid compound of claim 9, which is an aza-diamondoid.

12. The heterodiamondoid compound of claim 9, wherein the electron-donating heteroatom is sp3-hybridized in the diamond lattice.

13. The heterodiamondoid compound of claim 1 wherein at least one of $R^1$, $R^2$, $R^3$, $R^4$, $R^5$, and $R^6$ is a covalently bonded functional group.

14. The heterodiamondoid compound of claim 7 wherein at least one of $R^1$, $R^2$, $R^3$, $R^4$, $R^5$, and $R^6$ is a covalently bonded functional group.

15. The heterodiamondoid compound of claim 8 wherein at least one of $R^1$, $R^2$, $R^3$, $R^4$, $R^5$, and $R^6$ is a covalently bonded functional group.

16. The heterodiamondoid compound of claim 13 wherein the covalently bonded functional group comprise a group selected from the group consisting of halo, thio, oxide, hydroxyl, nitro, sulfonylhalide, sulfonate, phosphine, added alkyl, alkenyl, alkynyl and aryl, with or without substitution.

17. The functionalized heterodiamondoid compound of claim 13 wherein the one or more functional groups comprise a halo.

18. The functionalized heterodiamondoid compound of claim 13 wherein the one or more functional groups comprise a hydroxide.

19. The functionalized heterodiamondoid compound of claim 13 wherein the one or more functional groups comprise an oxide.

20. The functionalized heterodiamondoid compound of claim 13 wherein the one or more functional groups comprise a nitrate.

21. The functionalized heterodiamondoid compound of claim 13 wherein the one or more functional groups comprise a group selected from the group consisting of haloalkyl; haloalkenyl; haloalkynyl; hydroxyalkyl; alkylthio; alkoxy; aminoalkyl; aminoalkoxy; cycloalkyloxy; aryloxy; —C(O)Z; —CO2Z; —R7COZ wherein R7 is alkenyl, aminoalkenyl, or haloalkenyl; —R7COOZ; —OSO3H; NH2; NHR'; NR'R"; and N+R'R"R'" wherein R', R", and R'" are independently alkyl, thio, thioalkyl, heteroalkyl, or aryl; R8NHCOR9 wherein R8 is selected from the group consisting of CH2, OCH2, NHCH2, CH2CH2, and OCH2CH2 and R9 is selected from the group consisting of alkyl, aryl, and; R10CONHR11 wherein R10 is selected from the group consisting of CH2, OCH2, NHCH2, CH2CH2, and OCH2CH2, and R11 is selected from the group consisting of alkyl, aryl, heteroaryl, aralkyl, wherein Z is hydrogen, alkyl, halo, haloalkyl, haloothio, amino, monosubstituted amino, disubstituted amino, cycloalkyl, or aryl.

22. The functionalized heterodiamondoid compound of claim 13, wherein the one or more functional groups comprise a polymerizable functional group.

23. The heterodiamondoid compound of claim 1 as a discrete molecule.

24. The heterodiamondoid compound of claim 1 as a crystal.

* * * * *